(12) United States Patent
Graupe et al.

(10) Patent No.: US 7,101,880 B2
(45) Date of Patent: Sep. 5, 2006

(54) PEPTIDIC COMPOUNDS AS CYSTEINE PROTEASE INHIBITORS

(75) Inventors: Michael Graupe, Pacifica, CA (US); John O. Link, San Francisco, CA (US)

(73) Assignee: Schering Aktiengesellschaft, Berlin (DE)

(*) Notice: Subject to any disclaimer, the term of this patent is extended or adjusted under 35 U.S.C. 154(b) by 0 days.

(21) Appl. No.: 10/603,437

(22) Filed: Jun. 24, 2003

(65) Prior Publication Data

US 2004/0127426 A1    Jul. 1, 2004

Related U.S. Application Data

(60) Provisional application No. 60/422,710, filed on Oct. 30, 2002, provisional application No. 60/422,234, filed on Oct. 30, 2002, provisional application No. 60/391,051, filed on Jun. 24, 2002.

(51) Int. Cl.
*A61K 31/535*    (2006.01)
*C07D 413/00*    (2006.01)

(52) U.S. Cl. .................. 514/232.5; 544/137
(58) Field of Classification Search ............ 544/137; 514/232.5
See application file for complete search history.

(56) References Cited

U.S. PATENT DOCUMENTS

| | | | | |
|---|---|---|---|---|
| 5,776,718 A * | 7/1998 | Palmer et al. ............ 435/23 |
| 5,925,772 A * | 7/1999 | Zimmerman et al. ....... 548/534 |
| 5,998,470 A * | 12/1999 | Halbert et al. ............ 514/482 |
| 6,015,879 A * | 1/2000 | McDonald et al. ......... 530/331 |
| 6,017,887 A * | 1/2000 | Munoz et al. ............. 514/19 |
| 6,150,416 A | 11/2000 | Kick et al. |
| 6,297,277 B1 * | 10/2001 | Zimmerman et al. ....... 514/534 |
| 6,395,897 B1 | 5/2002 | Cywin et al. |
| 6,420,364 B1 | 7/2002 | Emmanuel et al. |
| 6,544,767 B1 * | 4/2003 | Bromme et al. ............ 435/226 |
| 6,583,137 B1 * | 6/2003 | Marquis et al. .......... 514/217.05 |
| 6,608,030 B1 * | 8/2003 | Ploegh et al. .............. 514/13 |
| 6,730,671 B1 * | 5/2004 | Cywin et al. ............. 514/232.8 |

FOREIGN PATENT DOCUMENTS

| | | |
|---|---|---|
| WO | WO 00/55124 | 9/2000 |
| WO | WO 00/55144 | 9/2000 |
| WO | WO 01/19796 | 3/2001 |
| WO | WO 01/19808 | 3/2001 |
| WO | WO 01/19816 | 3/2001 |
| WO | WO 01/68645 | 9/2001 |
| WO | WO 02/20485 | 3/2002 |
| WO | WO 02/051983 | 7/2002 |
| WO | WO 02/098850 | 12/2002 |
| WO | WO 03/024923 | 3/2003 |
| WO | WO 03/029200 | 4/2003 |
| WO | WO 03/037892 | 5/2003 |

OTHER PUBLICATIONS

Yasuma, Tsuneo et al: Synthesis of Peptide Aldehyde Derivatives as Selective Inhibitors of Huma Cathepsin L and Their Inhibitory Effect on Bone Resorption Journal of Medicinal Chemistry (1988), 41(22), 4301-4308.

* cited by examiner

*Primary Examiner*—Deborah C. Lambkin
(74) *Attorney, Agent, or Firm*—Townsend and Townsend and Crew LLP

(57) ABSTRACT

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

27 Claims, No Drawings

PEPTIDIC COMPOUNDS AS CYSTEINE PROTEASE INHIBITORS

CROSS-REFERENCE

This application claims priority under 35 U.S.C. 119(e) to U.S. Provisional Applications Ser. No. 60/391,051, filed on Jun. 24, 2002 and 60/422,234 and 60/422,710, filed on Oct. 30, 2002, the disclosures of which are incorporated herein by reference in their entirety.

FIELD OF THE INVENTION

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

STATE OF THE ART

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteoarthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis. In addition, cathepsin S is implicated in: allergic disorders, including, but not limited to asthma; and allogeneic immune reponses, including, but not limited to, rejection of organ transplants or tissue grafts.

Another cysteine protease, Cathepsin F, has been found in macrophages and is possibly involved in antigen processing. It is believed that Cathepsin F in stimulated lung macrophages and possibly other antigen presenting cells could play a role in airway inflammation (see G. P. Shi et al, *J. Exp. Med.* 2000, 191,1177)

In view of the number of diseases wherein it is recognized that an increase in cysteine protease activity contributes to the pathology and/or symptomatology of the disease, molecules which inhibit the activity of this class of enzymes, in particular molecules which inhibitor cathepsins B, K, L, F, and/or S, will therefore be useful as therapeutic agents.

SUMMARY OF THE INVENTION (1) In one aspect, this invention is directed to a compound of Formula (Ia) or (Ib):

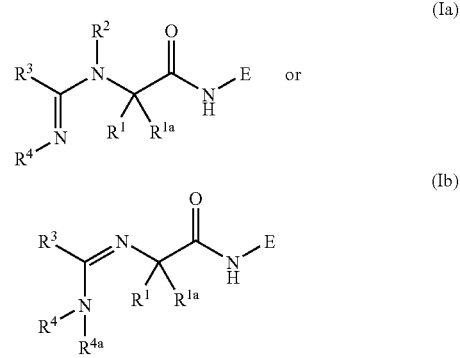

wherein:

E is:
—$C(R^5)(R^6)X^1$ where $X^1$ is —CHO, —$C(R^7)(R^8)CF_3$, —$C(R^7)(R^8)CF_2CF_2R^9$, —$C(R^7)(R^8)R^{10}$, —CH=CHS(O)$_2$ $R^{10}$, —$C(R^7)(R^8)C(R^7)(R^8)OR^{10}$, —$C(R^7)(R^8)CH_2OR^{10}$, —$C(R^7)(R^8)C(R^7)(R^8)R^{10}$, —$C(R^7)(R^8)CH_2N(R^{11})$ $SO_2R^{10}$, —$C(R^7)(R^8)CF_2C(O)NR^{10}OR^{11}$, —$C(R^7)(R^8)C(O)NR^{10}R^{11}$, —$C(R^7)(R^8)C(O)N(R^{11})(CH_2)_2OR^{11}$, or —$C(R^7)(R^8)C(O)N(R^{11})(CH_2)_2NHR^{11}$;

where:
$R^5$ is hydrogen or ($C_{1-6}$)alkyl;
$R^6$ is hydrogen, ($C_{1-6}$)alkyl, cyano, —$X^2NR^{12}R^{12a}$, —$X^2NR^{12}C(O)R^{12a}$, —$X^2NR^{12}C(O)OR^{12a}$, —$X^2NR^{12}C(O)NR^{12a}R^{12b}$, —$X^2NR^{12}C(NR^{12a})NR^{12b}R^{12c}$, —$X^2OR^{13}$, —$X^2SR^{13}$, —$X^2C(O)OR^{12}$, —$X^2C(O)R^{13}$, —$X^2OC(O)R^{13}$, —$X^2C(O)NR^{12}R^{12a}$, —$X^2S(O)_2NR^{12}R^{12a}$, —$X^2NR^{12}S(O)_2R^{13}$, —$X^2P(O)(OR^{12})OR^{12a}$, —$X^2OP(O)(OR^{12})OR^{12a}$, —$X^2S(O)R^{14}$, —$X^2S(O)_2R^{14}$, —$R^{15}$, —$X^2OR^{15}$, —$X^2SR^{15}$, —$X^2S(O)R^{15}$, —$X^2S(O)_2R^{15}$, —$X^2C(O)R^{15}$, —$X^2C(O)OR^{15}$, —$X^2OC(O)R^{15}$, —$X^2NR^{15}R^{12}$, —$X^2NR^{12}C(O)R^{15}$, —$X^2NR^{12}C(O)OR^{15}$, —$X^2C(O)NR^{15}R^{12}$, —$X^2S(O)_2NR^{15}R^{12}$, —$X^2NR^{12}S(O)_2R^{15}$, —$X^2NR^{12}C(O)NR^{15}R^{12a}$ or —$X^2NR^{12}C(NR^{12a})NR^{15}R^{12}$ where $X^2$ is ($C_{1-6}$) alkylene; $R^{12}$, $R^{12a}$, $R^{12b}$ and $R^{12c}$ at each occurrence independently is hydrogen or ($C_{1-6}$) alkyl; $R^{13}$ is hydrogen, ($C_{1-6}$)alkyl or halo-substituted($C_{1-6}$) alkyl, $R^{14}$ is ($C_{1-6}$)alkyl or halo-substituted($C_{1-6}$)alkyl; and $R^{15}$ is ($C_{3-10}$)cycloalkyl($C_{0-6}$)alkyl, hetero($C_{3-10}$)cycloalkyl ($C_{0-3}$)alkyl, ($C_{6-10}$)aryl($C_{0-6}$)alkyl, hetero($C_{5-10}$)aryl($C_{0-6}$) alkyl, ($C_{9-12}$)bicycloaryl($C_{0-6}$)alkyl or hetero($C_{8-12}$)bicycloaryl($C_{0-6}$)alkyl; or $R^5$ and $R^6$ taken together with the carbon atom to which both $R^5$ and $R^6$ are attached form ($C_{3-8}$)cycloalkylene or hetero($C_{3-8}$)cycloalkylene wherein said cycloalkylene and heterocycloalkylene may be substituted further with 1 to 2 radicals independently selected from ($C_{1-6}$)alkyl, cyano, halo, halo-substituted($C_{1-4}$)alkyl, nitro, —$X^3NR^{16}R^{16a}$, —$X^3NR^{16}C(O)R^{16a}$, —$X^3NR^{16}C(O)OR^{16a}$, —$X^3NR^{16}C(O)NR^{16a}R^{16b}$, —$X^3NR^{16}C(NR^{16a})NR^{16b}R^{16c}$, —$X^3OR^{17}$, —$X^3SR^{17}$, —$X^3C(O)OR^{16}$, —$X^3C(O)R^{17}$, —$X^3OC(O)R^{17}$, —$X^3C(O)NR^{16}R^{16a}$, —$X^3S(O)_2NR^{16}R^{16a}$, —$X^3NR^{16}S $(O)_2 R^{17}$, $-X^3P(O)(OR^{16})OR^{16a}$, $-X^3OP(O)(OR^{16})OR^{16a}$, $-X^3S(O)R^{18}$ and $-X^3S(O)_2R^{18}$ where $X^3$ is a bond or $(C_{1-6})$alkylene; $R^{16}$, $R^{16a}$, $R^{16b}$, and $R^{16c}$ at each occurrence independently is hydrogen or $(C_{1-6})$alkyl; $R^{17}$ is hydrogen, $(C_{1-6})$alkyl or halo-substituted$(C_{1-6})$alkyl, and $R^{18}$ is $(C_{1-6})$alkyl or halo-substituted$(C_{1-6})$alkyl;

$R^7$ is hydrogen or $(C_{1-4})$alkyl;

$R^8$ is hydroxy; or $R^7$ and $R^8$ together form oxo;

$R^9$ is hydrogen, halo, $(C_{1-4})$alkyl, $(C_{5-10})$aryl$(C_{0-6})$alkyl or hetero$(C_{5-10})$aryl$(C_{0-6})$-alkyl; and $R^{10}$ is $(C_{1-4})$alkyl, $(C_{6-10})$aryl$(C_{0-6})$alkyl, hetero$(C_{4-10})$aryl$(C_{0-6})$alkyl, $(C_{4-10})$cycloalkyl$(C_{0-6})$alkyl or hetero$(C_{4-10})$cycloalkyl$(C_{0-6})$alkyl; and $R^{11}$ is hydrogen or $(C_{1-6})$alkyl; or a group of formula (a):

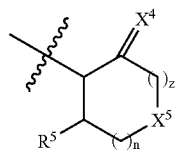

(a)

where:

n is 0, 1, or 2;

z is 0 or 1;

$X^4$ is selected from $NR^{19}$, S, or O where $R^{19}$ is hydrogen or $(C_{1-6})$alkyl; and $X^5$ is $-O-$, $-S-$, $-SO_2-$, or $-NR^{20}-$ where $R^{20}$ is selected from hydrogen, $(C_{1-6})$ alkyl, $-X^6C(O)OR^{22}$, $-X^6C(O)NR^{22}R^{22a}$, $-X^6S(O)_2NR^{22}R^{22a}$, $-X^6C(O)R^{23}$, $-X^6S(O)_2R^{24}$, $-R^{25}$, $-X^6C(O)OR^{25}$, $-X^6C(O)NR^{22}R^{25}$, $-X^6S(O)_2NR^{22}R^{25}$, $-X^6C(O)R^{25}$ and $-X^6S(O)_2R^{25}$ in which $X^6$ is a bond or $(C_{1-6})$alkylene; $R^{22}$ and $R^{22a}$ at each occurrence independently is hydrogen or $(C_{1-6})$alkyl; $R^{23}$ is hydrogen, $(C_{1-6})$alkyl or halo-substituted$(C_{1-6})$alkyl, $R^{24}$ is $(C_{1-6})$alkyl or halo-substituted$(C_{1-6})$alkyl, and $R^{25}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-12})$bicycloaryl$(C_{0-6})$alkyl or hetero$(C_{8-12})$bicycloaryl$(C_{0-6})$alkyl provided that when $R^5$ is hydrogen, then both $X^4$ and $X^5$ are not $-O-$;

$R^5$ is as defined above;

and furthermore within E any cycloalkyl, heterocycloalkyl, aryl or heteroaryl may be substituted with $R^x$ selected from $-R^{26}$, $-X^7OR^{26}$, $-X^7SR^{26}$, $-X^7S(O)R^{26}$, $-X^7S(O)_2R^{26}$, $-X^7C(O)R^{26}$, $-X^7C(O)OR^{26}$, $-X^7OC(O)R^{26}$, $-X^7NR^{26}R^{27}$, $-X^7NR^{27}C(O)R^{26}$, $-X^7NR^{27}C(O)OR^{26}$, $-X^7C(O)NR^{26}R^{27}$, $-X^7S(O)_2NR^{26}R^{27}$, $-X^7NR^{27}S(O)_2R^{26}$, $-X^7NR^{27}C(O)NR^{26}R^{27a}$ and $-X^7NR^{27}C(NR^{27a})NR^{26}R^{27b}$ and wherein E and $R^x$ may be substituted further with 1 to 5 radicals independently selected from $(C_{1-6})$alkyl, cyano, halo, halo-substituted$(C_{1-4})$alkyl, nitro, $-X^8NR^{28}R^{28a}$, $-X^8NR^{28}C(O)R^{28a}$, $-X^8NR^{28}C(O)OR^{28a}$, $-X^8NR^{28}C(O)NR^{28a}R^{28b}$, $-X^8NR^{28}C(NR^{28a})NR^{28b}R^{28c}$, $-X^8OR^{29}$, $-X^8SR^{29}$, $-X^8C(O)OR^{28}$, $-X^8C(O)R^{29}$, $-X^8OC(O)R^{29}$, $-X^8C(O)NR^{28}R^{28a}$, $-X^8S(O)_2NR^{28}R^{28a}$, $-X^8NR^{28}S(O)_2R^{29}$, $-X^8P(O)(OR^{28})OR^{28a}$, $-X^8OP(O)(OR^{28})OR^{28a}$, $-X^8S(O)R^{30}$ and $-X^8S(O)_2R^{30}$ wherein $X^7$ and $X^8$ are independently a bond or $(C_{1-6})$alkylene; $R^{26}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-12})$bicycloaryl$(C_{0-6})$alkyl or hetero$(C_{8-12})$bicycloaryl-$(C_{0-6})$alkyl, $R^{27}$, $R^{27a}$, $R^{27b}$, $R^{28}$, $R^{28a}$, $R^{28b}$ and $R^{28c}$ at each occurrence independently is hydrogen or $(C_{1-6})$alkyl, $R^{29}$ is hydrogen, $(C_{1-6})$alkyl or halo-substituted$(C_{1-6})$alkyl, and $R^{30}$ is $(C_{1-6})$alkyl or halo-substituted$(C_{1-6})$alkyl;

$R^1$ is $(C_{1-10})$alkyl or $-C(R^{31})(R^{32})X^9$ wherein $R^{31}$ and $R^{32}$ are independently hydrogen or $(C_{1-6})$alkyl and $X^9$ is selected from $-X^{10}NR^{33}R^{33a}$, $-X^{10}NR^{33}C(O)R^{33a}$, $-X^{10}NR^{33}C(O)OR^{33a}$, $-X^{10}NR^{33}C(O)NR^{33a}R^{33b}$, $-X^{10}NR^{33}C(NR^{33a})NR^{33b}R^{33c}$, $-X^{10}OR^{33}$, $-X^{10}SR^{33}$, $-X^{10}C(O)OR^{33}$, $-X^{10}C(O)R^{33}$, $-X^{10}OC(O)R^{33}$, $-X^{10}C(O)NR^{33}R^{33a}$, $-X^{10}S(O)_2NR^{33}R^{33a}$, $-X^{10}NR^{33}S(O)_2R^{33a}$, $-X^{10}P(O)(OR^{33})OR^{33a}$, $-X^{10}OP(O)(OR^{33})OR^{33a}$, $-X^{10}C(O)R^{34}$, $-X^{10}NR^{33}C(O)R^{34}$, $-X^{10}S(O)R^{34}$, $-X^{10}S(O)_2R^{34}$, $-R^{35}$, $-X^{10}OR^{35}$, $-X^{10}SR^{35}$, $-X^{10}S(O)R^{35}$, $-X^{10}S(O)_2R^{35}$, $-X^{10}C(O)R^{35}$, $-X^{10}C(O)OR^{35}$, $-X^{10}OC(O)R^{35}$, $-X^{10}NR^{33}R^{35}$, $-X^{10}NR^{33}C(O)R^{35}$, $-X^{10}NR^{33}C(O)OR^{35}$, $-X^{10}C(O)NR^{33}R^{35}$, $-X^{10}S(O)_2NR^{33}R^{35}$, $-X^{10}NR^{33}S(O)_2R^{35}$, $-X^{10}NR^{33}C(O)NR^{33a}R^{35}$ and $-X^{10}NR^{33}C(NR^{33a})NR^{33b}R^{35}$ wherein $X^{10}$ is a bond or $(C_{1-6})$alkylene; $R^{33}$, $R^{33a}$, $R^{33b}$, and $R^{33c}$ at each occurrence independently is hydrogen, $(C_{1-6})$alkyl or halo-substituted$(C_{1-6})$alkyl; $R^{34}$ is $(C_{1-6})$alkyl or halo-substituted$(C_{1-6})$alkyl; and $R^{35}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-10})$bicycloaryl$(C_{0-6})$alkyl or hetero$(C_{8-10})$bicycloaryl$(C_{0-6})$alkyl;

wherein within $R^1$ any alicyclic or aromatic ring system is unsubstituted or substituted further by 1 to 5 radicals independently selected from $(C_{1-6})$alkyl, $(C_{1-6})$alkylidene, cyano, halo, halo-substituted$(C_{1-4})$alkyl, nitro, $-X^{11}NR^{36}R^{36a}$, $-X^{11}NR^{36}C(O)R^{36a}$, $-X^{11}NR^{36}C(O)OR^{36a}$, $-X^{11}NR^{36}C(O)NR^{36a}R^{36b}$, $-X^{11}NR^{36}C(NR^{36a})NR^{36b}R^{36c}$, $-X^{11}OR^{36}$, $-X^{11}SR^{36}$, $-X^{11}C(O)OR^{36}$, $-X^{11}C(O)R^{36}$, $-X^{11}OC(O)R^{36}$, $-X^{11}C(O)NR^{36}R^{36a}$, $-X^{11}S(O)_2NR^{36}R^{36a}$, $-X^{11}NR^{36}S(O)_2R^{36a}$, $-X^{11}P(O)(OR^{36})OR^{36a}$, $-X^{11}P(O)(OR^{36})OR^{36a}$, $-X^{11}NR^{36}C(O)R^{37}$, $-X^{11}S(O)R^{37}$, $-X^{11}C(O)R^{37}$ and $-X^{11}S(O)_2R^{37}$ and/or 1 radical selected from $-R^{38}$, $-X^{12}OR^{38}$, $-X^{12}SR^{38}$, $-X^{12}S(O)R^{38}$, $-X^{12}S(O)_2R^{38}$, $-X^{12}C(O)R^{38}$, $-X^{12}C(O)OR^{38}$, $-X^{12}OC(O)R^{38}$, $-X^{12}NR^{36}R^{38}$, $-X^{12}NR^{36}C(O)R^{38}$, $-X^{12}NR^{36}C(O)OR^{38}$, $-X^{12}C(O)NR^{36}R^{38}$, $-X^{12}S(O)_2NR^{36}R^{38}$, $-X^{12}NR^{36}S(O)_2R^{38}$, $-X^{12}NR^{36}C(O)NR^{36a}R^{38}$ and $-X^{12}NR^{36}C(NR^{36a})NR^{36b}R^{38}$; and within $R^1$ any aliphatic moiety is unsubstituted or substituted further by 1 to 5 radicals independently selected from cyano, halo, nitro, $-NR^{39}R^{39a}$, $-N39C(O)R^{39a}$, $-NR^{39}C(O)OR^{39a}$, $-NR^{39}C(O)NR^{39a}R^{39b}$, $-NR^{39}C(NR^{39a})NR^{39b}R^{39c}$, $-OR^{39}$, $-SR^{39}$, $-C(O)OR^{39}$, $-C(O)R^{39}$, $-OC(O)R^{39}$, $-C(O)NR^{39}R^{39a}$, $S(O)_2NR^{39}R^{39a}$, $-NR^{39}S(O)_2R^{39a}$, $-P(O)(OR^{39})OR^{39a}$, $-OP(O)(OR^{39})OR^{39a}$, $-NR^{39}C(O)R^{40}$, $-S(O)R^{40}$ and $-S(O)_2R^{40}$; wherein $X^{11}$ and $X^{12}$ are independently a bond or $(C_{1-6})$alkylene; $R^{36}$, $R^{36a}$, $R^{36b}$, $R^{36c}$, $R^{39}$, $R^{39a}$, $R^{39b}$ and $R^{39c}$ at each occurrence independently is hydrogen, $(C_{1-6})$alkyl or halo-substituted$(C_{1-6})$alkyl; $R^{37}$ and $R^{40}$ are independently $(C_{1-6})$alkyl or halo-substituted$(C_{1-6})$alkyl; and $R^{38}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-10})$bicycloaryl$(C_{0-6})$alkyl or hetero$(C_{8-10})$bicycloaryl$(C_{0-6})$alkyl, provided that only one $(C_{9-10})$bicycloaryl$(C_{0-6})$alkyl or hetero$(C_{8-10})$bicycloaryl$(C_{0-6})$alkyl ring structure is present within $R^1$;

$R^{1a}$ is hydrogen or $(C_{1-6})$alkyl; or $R^1$ and $R^{1a}$ together with the carbon atoms to which they are attached form $(C_{3-8})$cycloalkylene or hetero$(C_{3-10})$cycloalkylene ring wherein said cycloalkylene ring is optionally substituted with one or two substitutents independently selected from $(C_{1-6})$alkyl, $(C_{1-6})$alkoxy, hydroxy, halo, hydroxyalkyl, or keto and said heterocycloalkylene ring is optionally substituted with one or two substitutents independently selected from $(C_{1-6})$alkyl, $(C_{1-6})$alkoxy, hydroxyalkyl, alkoxyalkyl, aminoalkyl, acyl, $(C_{3-10})$cycloalkyl$(C_{0-6})$ alkyl, hetero$(C_{3-10})$cycloalkyl$(C_{0-3})$alkyl, $(C_{6-10})$aryl$(C_{0-6})$ alkyl, hetero$(C_{5-10})$aryl$(C_{0-6})$alkyl wherein said aryl, heteroaryl, and heterocycloalkyl are optionally substituted with one, two, or three substitutents independently selected from $(C_{1-6})$alkyl, $(C_{1-6})$alkoxy, nitro, amino, halo, hydroxy, alkylthio, halo-substituted alkyl, halo-substituted alkoxy, acyl, —OC(O)R$^{39}$, —C(O)$^{39}$R$^{39a}$, S(O)$_2$NR$^{39}$R$^{39a}$, —S(O)$_2$R$^{38}$ or —S(O)$_2$R$^{40}$ where R$^{38}$, R$^{38}$, R$^{39}$, R$^{39a}$, and R$^{40}$ are as defined above;

R$^2$ is hydrogen, hydroxy, or $(C_{1-6})$alkyl;

R$^3$ is hydrogen, $(C_{1-6})$alkyl, $(C_{1-6})$alkoxy, aryloxy, $(C_{3-8})$ cycloalkyl, $(C_{3-8})$cycloalkyloxy, aryl, benzyl, tetrahydronaphthyl, indenyl, indanyl, $(C_{1-6})$alkylsulfonyl$(C_{1-6})$ alkyl, $(C_{3-8})$cycloalkylsulfonyl$(C_{1-6})$alkyl, arylsulfonyl $(C_{1-6})$alkyl, heterocyclic ring selected from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzisoxazolyl, quinolinyl, tetrahydroquinolinyl, isoquinolinyl, tetrahydroisoquinolinyl, quinazolinyl, tetrahydroquinazolinyl, benzoxazolyl or quinoxalinyl, —OR where R is a heterocyclic moiety selected from those herein described in this paragraph, or amino; wherein R$^3$ is optionally substituted by one, two, or three R$^a$;

each R$^a$ is independently $(C_{1-6})$alkyl, $(C_{3-8})$cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, $(C_{1-6})$alkoxy, $(C_{1-6})$ haloalkoxy, $(C_{1-6})$alkanoyl, $(C_{1-6})$alkanoyloxy, aryloxy, benzyloxy, $(C_{1-6})$alkoxycarbonyl, aryloxycarbonyl, aroyloxy, carbamoyl wherein the nitrogen atom may be independently mono or di-substituted by $(C_{1-6})$alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each R$^a$ is independently $(C_{1-6})$alkanoylamino, aroylamino, $(C_{1-6})$alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by $(C_{1-6})$alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each R$^a$ is independently $(C_{1-6})$alkoxycarbonylamino, aryloxycarbonylamino, $(C_{1-6})$-alkylcarbamoyloxy, arylcarbamoyloxy, $(C_{1-6})$alkylsulfonylamino, arylsulfonyl-amino, aminosulfonyl, $(C_{1-6})$alkylaminosulfonyl, di-$(C_{1-6})$alkylaminosulfonyl, arylaminosulfonyl, amino wherein the nitrogen atom may be independently mono or di-substituted by $(C_{1-6})$alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each R$^a$ is independently halogen, hydroxy, $(C_{1-6})$alkoxy, $(C_{1-6})$haloalkyl, $(C_{1-6})$haloalkoxy, oxo, carboxy, cyano, nitro, carboxamide, amidino or guanidino, R$^a$ is may be further optionally substituted by one, two, or three R$^b$;

each R$^b$ is independently $(C_{1-6})$alkyl optionally partially or fully halogenated wherein one or more carbon atoms are optionally replaced by O, N, S(O), S(O)$_2$ or S and wherein said alkyl is optionally independently substituted with 1–2 oxo groups, —NH$_2$, or one or more C$_{1-4}$alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, or quinoxalinyl; or each R$^b$ is independently $(C_{3-6})$cycloalkyl, aryl, aryloxy, benzyloxy, halogen, hydroxy, $(C_{1-6})$alkyl, $(C_{1-6})$alkoxy, $(C_{1-6})$haloalkyl, $(C_{1-6})$haloalkoxy, aminosulfonyl, $(C_{1-6})$ alkylaminosulfonyl, di-$(C_{1-6})$alkylaminosulfonyl, arylaminosulfonyl, oxo, carboxy, cyano, nitro, mono-C$_{1-5}$alkylamino, di-$(C_{1-5})$alkylamino, carboxamide, amidino or guanidino;

R$^4$ is hydrogen, hydroxy, nitrile, or a $(C_{1-6})$alkyl optionally partially or fully halogenated wherein one or more C atoms are optionally replaced by O, NH, S(O), S(O)$_2$ or S and wherein said alkyl chain is optionally independently substituted with 1–2 oxo groups, —NH$_2$, one or more C$_{1-4}$ alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl; or R$^3$ and R$^4$ in (Ia) or (Ib) together with the atoms to which they are attached form a heterocycloalkyl ring containing at least an —SO$_2$— group or a heterocycloalkyl ring fused to an aryl or heteroaryl ring wherein said heterocycloalkyl rings are optionally substituted on the aromatic and/or non-aromatic portion of the rings with one, two, or three R$^C$;

each R$^C$ and R$^{4a}$ is independently:

hydrogen, $(C_{1-6})$alkyl optionally interrupted by one or two N, O, S, S(O), or S(O)$_2$ and optionally substituted by 1–2 oxo, amino, hydroxy, halogen, C$_{1-4}$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl; halo, alkoxy, alkylthio, hydroxy, carboxy, aryl, aryloxy, aroyl, heteroaryl, $(C_{1-6})$alkanoyl, —C(O)OR$^d$ where (R$^d$ is hydrogen, $(C_{1-6})$ alkyl, $(C_{1-6})$alkoxyalkyl, $(C_{1-6})$haloalkyl, $(C_{3-7})$cycloalkyl, $(C_{3-7})$cycloalkyl$(C_{1-6})$alkyl, heteroaryl, heteroaryl$(C_{1-6})$ alkyl, aryl, or aryl$(C_{1-6})$alkyl), $(C_{1-6})$alkylsulfonyl, aryloxycarbonyl, benzyloxycarbonyl, $(C_{1-6})$alkanoylamino, aroylamino, C$_{1-5}$ alkylthio, arylthio, $(C_{1-6})$alkylsulfonylamino, arylsulfonylamino, $(C_{1-6})$alkylamino-sulfonyl, arylaminosulfonyl, $(C_{3-6})$cycloalkyl and benzyloxy wherein each of the aforementioned groups is optionally substituted with halogen, hydroxy, $(C_{1-6})$alkyl, $(C_{1-6})$alkoxy, $(C_{1-6})$haloalkyl, $(C_{1-6})$haloalkoxy, oxo, carboxy, nitrile, nitro or $NH_2C(O)$—;

or a pharmaceutically acceptable salts thereof provided that there are no more than 5 ring systems in a compound of Formula (Ia) or (Ib).

(2) Within group (1) above, a more preferred group of compounds is that wherein: when $R^3$ and $R^4$ together with the atoms to which they are attached form a heterocycloalkyl ring or a heterocyclic ring fused to an aryl or heteroaryl ring then the heterocycloalkyl rings contain at least an —$SO_2$— group.

(3) Within group (1) above, a more preferred group of compounds is that wherein: when $R^3$ and $R^4$ together with the atoms to which they are attached form a heterocycloalkyl ring or a heterocyclic ring fused to an aryl or heteroaryl ring then the heterocycloalkyl rings do not contain an —$SO_2$— group.

A second aspect of the invention is directed to a pharmaceutical composition comprising a therapeutically effective amount of a compound of Formula (Ia) or (Ib), individual isomer or mixture of isomers thereof, or a pharmaceutically acceptable salt thereof, in admixture with one or more suitable excipients.

A third aspect of the invention is a method for treating a disease in an animal mediated by cysteine proteases, in particular cathepsin K, S, or F, preferably S, which method comprises administering to the animal a pharmaceutical composition comprising a therapeutically effective amount of compound of Formula (Ia) or (Ib), individual isomer or mixture of isomers thereof, or a pharmaceutically acceptable salt thereof.

A fourth aspect of the invention is the processes for preparing compounds of Formula (Ia) or (Ib) and the pharmaceutically acceptable salts thereof, in admixture with one or more suitable excipients.

A fifth aspect of this invention is directed to an intermediate of formula:

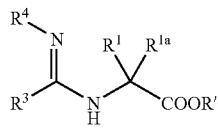

where R' is hydrogen or saturated alkyl, and $R^1$, $R^{1a}$, $R^3$ and $R^4$ are as defined in group (1) above.

DETAILED DESCRIPTION OF THE INVENTION

Definitions:

Unless otherwise stated, the following terms used in the specification and claims are defined for the purposes of this application and have the following meanings.

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by a straight or branched chain arrangement of the constituent carbon atoms and may be saturated or partially unsaturated with two or more double or triple bonds.

"Alkyl" represented by itself means a straight or branched, saturated or unsaturated, aliphatic radical containing one to ten carbon atoms, preferably one to six carbon atoms, unless otherwise indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-10})$aryl$(C_{0-3})$alkyl includes phenyl, benzyl, phenethyl, 1-phenylethyl 3-phenylpropyl, and the like). It should be understood that any combination term using an "alk" or "alkyl" prefix refers to analogs according to the above definition of "alkyl". For example, terms such as "alkoxy" "alkythio" refer to alkyl groups linked to a second group via an oxygen or sulfur atom.

"Alkanoyl" refers to an alkyl group linked to a carbonyl group (C=O).

"Alkanoyloxy" refers to an alkyl group linked to a carbonyloxy group —O(C=O).

"Alkylene", unless indicated otherwise, means a straight or branched, saturated or unsaturated, aliphatic, divalent radical having the number of carbon atoms indicated (e.g., $(C_{1-6})$alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like).

"Alkylidene" means a straight or branched saturated or unsaturated, aliphatic, divalent radical having the number of carbon atoms indicated (e.g. $(C_{1-6})$alkylidene includes methylene (=$CH_2$), ethylidene (=$CHCH_3$), isopropylidene (=$C(CH_3)_2$), propylidene (=$CHCH_2CH_3$), allylidene (=$CH^-CH=CH_2$), and the like).

"Alkylcarbamoyloxy" refers to a radical —OCONHR where R is an alkyl group e.g., methylcarbamoyloxy, ethylcarbamoyloxy, and the like.

"Alkylsulfonylamino" refers to a radical —$NHSO_2R$ where R is an alkyl group e.g., methylsulfonylamino, ethylsulfonylamino, and the like.

"Alkylsulfonylalkyl" refers to a radical -(alkylene)-$SO_2R$ where R is an alkyl group as defined above, unless otherwise stated e.g., methylsulfonylethyl, methylsulfonylmethyl, and the like.

"Amino" means the radical —$NH_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Alkanoylamino" refers to a radical —NHC(O)R where R is an alkyl group as defined above, unless otherwise stated e.g., methylcarbonylamino, ethylcarbonylamino, and the like.

"Aminosulfonyl" refers to a radical —$SO_2NH_2$.

"Alkylaminosulfonyl" or "Dialkylaminosulfonyl" refers to a radical —$SO_2NHR$ and —$SO_2NRR'$ respectively, where R and R' are independently alkyl group e.g., methylaminosulfonyl, and the like.

"Alkoxy" refers to a radical —OR where R is an alkyl group e.g., methoxy, ethoxy, and the like.

"Alkoxycarbonyl" refers to a radical —C(O)OR where R is an alkyl group e.g., methoxycarbonyl, ethoxycarbonyl, and the like.

"Alkoxycarbonylamino" refers to a radical —NHC(O)OR where R is an alkyl group e.g., methoxycarbonyl, ethoxycarbonyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Aminoalkyl" means a linear monovalent hydrocarbon radical of one to six carbon atoms or a branched monovalent hydrocarbon radical of three to six carbons substituted with at least one, preferably one or two, —NHR where R is hydrogen or —COR$^a$ where R$^a$ is alkyl, e.g., aminomethyl, methylaminoethyl, 1,3-diaminopropyl, acetylaminopropyl, and the like.

"Alkylthio" refers to a radical —SR where R is an alkyl group e.g., methylthio, ethylthio, and the like.

"Acyl" means a radical —COR where R is hydrogen, alkyl or haloalkyl as defined herein, e.g., formyl, acetyl, trifluoroacetyl, and the like.

"Amidino" means a radical —C(=NH)NH$_2$.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2.

"Aryl" means a monocyclic or fused bicyclic ring assembly containing 6 to 10 ring carbon atoms unless otherwise indicated, wherein each ring is aromatic e.g., phenyl or anthryl.

"Arylalkyl" means a radical -(alkylene)-R where R is aryl as defined above e.g., benzyl.

"Aryloxy" means a radical —OR where R is aryl as defined above.

"Aryloxycarbonyl" means the radical —C(O)OR where R is aryl as defined above e.g., phenyloxycarbonyl, and the like.

"Aryloxycarbonylamino" means the radical —NHC(O) OR where R is aryl as defined above e.g., phenyloxycarbonylamino, and the like.

"Arylcarbamoyloxy" means the radical —OC(O)NHR where R is aryl as defined above e.g., phenylcarbamoyloxy, and the like.

"Aroyl" means the radical —COR where R is aryl as defined above e.g., benzoyl.

"Aroylamino" means the radical —NHCOR where R is aryl as defined above e.g., benzoylamino.

"Aroyloxy" means the radical —OC(O)R where R is aryl as defined above.

"Arylsulfonylalkyl" refers to a radical -(alkylene)-SO$_2$R where R is an aryl group as defined above, unless otherwise stated e.g., phenylsulfonylethyl, phenylsulfonylmethyl, and the like.

"Arylsulfonylamino" refers to a radical —NHSO$_2$R where R is an aryl group as defined above, unless otherwise stated e.g., phenylsulfonylamino, and the like.

"Arylaminosulfonyl" means the radical —SO$_2$NHR where R is aryl as defined above e.g., phenylaminosulfonyl, and the like.

"Bicycloaryl" means a bicyclic ring assembly containing the number of ring carbon atoms indicated, wherein the rings are linked by a single bond or fused and at least one of the rings comprising the assembly is aromatic, and any (C$_{1-6}$) alkylidene, carbocyclic ketone, thioketone or iminoketone derivative thereof (e.g., (C$_{9-12}$)bicycloaryl includes biphenyl, cyclohexylphenyl, 1,2-dihydronaphthyl, 2,4-dioxo-1,2,3,4-tetrahydronaphthyl, indanyl, indenyl, 1,2,3,4-tetrahydronaphthyl, and the like).

"Carbamoyl" or "carboxamide" means the radical —C(O) NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carbocyclic ketone derivative" means a derivative containing the moiety —C(O)—.

"Carboxy" means the radical —C(O)OH. Unless indicated otherwise, the compounds of the invention containing carboxy moieties include protected derivatives thereof. Suitable protecting groups for carboxy moieties include benzyl, tert-butyl, and the like.

"Cycloalkyl" means a saturated or partially unsaturated, monocyclic, fused bicyclic or bridged polycyclic ring assembly containing three to eight ring carbon atoms unless otherwise indicated, and any (C$_{1-6}$)alkylidene, carbocyclic ketone, thioketone or iminoketone derivative thereof (e.g., (C$_{3-10}$)cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like).

"Cycloalkyloxy" means the radical —OR where R is cycloalkyl as defined above e.g., cyclobutyloxy, pentyloxy, hexyloxy, and the like.

"Cycloalkylene" means a divalent saturated, partially unsaturated or fully unsaturated (provided that it is not aromatic) monocyclic ring or bridged polycyclic ring assembly containing three to eight ring carbon atoms unless otherwise indicated, and any carbocyclic ketone, thioketone or iminoketone derivative thereof. For example, the instance wherein "R$^1$ and R$^2$ together with the carbon atom to which both R$^1$ and R$^2$ are attached form (C$_{3-8}$)cycloalkylene" includes, but is not limited to, the following:

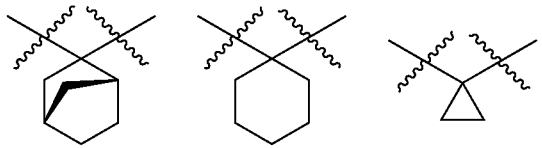

"Cycloalkylsulfonylalkyl" refers to a radical -(alkylene)-SO$_2$R where R is a cycloalkyl group as defined above, unless otherwise stated e.g., cyclopropylsulfonylethyl, cyclohexylsulfonylmethyl, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" or "halogen" means fluoro, chloro, bromo or iodo.

"Halo-substituted alkyl" or "haloalkyl" as an isolated group or part of a larger group, means "alkyl" substituted by one or more "halo" atoms, as such terms are defined in this application. Halo-substituted alkyl or haloalkyl includes monohaloalkyl, dihaloalkyl, trihaloalkyl, perhaloalkyl and the like (e.g. halo-substituted (C$_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Haloalkoxy" refers to a radical —OR where R is haloalkyl group as defined above e.g., trifluoromethoxy, 2,2,2-trifluoroethoxy, difluoromethoxy, and the like.

"Heteroatom moiety" includes —N═, —NR—, —O—, —S— or —S(O)$_2$—, wherein R is hydrogen, (C$_{1-6}$)alkyl or a protecting group.

"Heterocycloalkylene" means cycloalkylene, as defined in this application, provided that one or more of the ring member carbon atoms indicated, is replaced by heteroatom moiety selected from —N═, —NR—, —O—, —S— or —S(O)$_2$—, wherein R is hydrogen or (C$_{1-6}$)alkyl. For example, the instance wherein R$^1$ and R$^2$ together with the carbon atom to which both R$^1$ and R$^2$ are attached form hetero(C$_{3-8}$)cycloalkylene" includes, but is not limited to, the following:

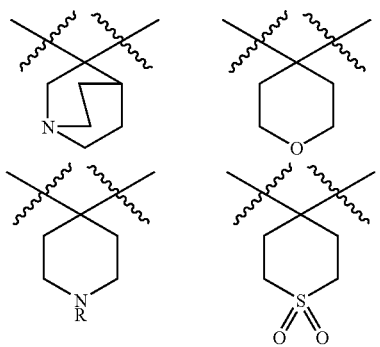

in which R is hydrogen, (C$_{1-6}$)alkyl, or a protecting group e.g., —COR where R is hydrogen, alkyl, or haloalkyl, —OC(O)R where R$^z$ is alkyl, aryl or heteroaryl, —C(O) NR$^z$R$^z$, —S(O)$_2$N R$^z$R$^z$, or —S(O)$_2$R$^z$ where R$^z$ is independently (C$_{1-6}$)alkyl, halo-substituted(C$_{1-6}$)-alkyl, (C$_{3-10}$)cycloalkyl(C$_{0-6}$)alkyl, hetero(C$_{3-10}$)cycloalkyl(C$_{0-3}$)alkyl, (C$_{6-10}$)aryl(C$_{0-6}$)alkyl, hetero(C$_{5-10}$)aryl(C$_{0-6}$)alkyl, (C$_{9-10}$) bicycloaryl(C$_{0-6}$)alkyl or hetero(C$_{8-10}$)bicycloaryl-(C$_{0-6}$) alkyl "Heteroaryl" as a group or part of a group denotes an optionally substituted aromatic monocyclic or multicyclic organic moiety of 5 to about 10 ring members in which one or more of the ring members is/are element(s) other than carbon, for example nitrogen, NR, oxygen or sulfur, wherein R is hydrogen, (C$_{1-6}$)alkyl, a protecting group or represents the free valence which serves as the point of attachment to a ring nitrogen.

"Heteroarylalkyl" means a radical -(alkylene)-R where R is heteroaryl as defined above e.g., pyridinylmethyl, furanylethyl, and the like.

"Heterobicycloaryl" means bicycloaryl, as defined in this application, provided that one or more of the ring carbon atoms indicated are replaced by a heteroatom moiety selected from —N═, —NR—, —O— or —S—, wherein R is hydrogen, (C$_{1-6}$)alkyl, a protecting group or represents the free valence which serves as the point of attachment to a ring nitrogen, and any carbocyclic ketone, thioketone or iminoketone derivative thereof. For example, optionally substituted hetero(C$_{8-10}$)bicycloaryl as used in this application includes, but is not limited to, 2-amino-4-oxo-3,4-dihydropteridin-6-yl, and the like. In general, the term heterobicycloaryl as used in this application includes, for example, benzo[1,3]dioxol-5-yl, 3,4-dihydro-2H-[1,8]naphthyridinyl, 3,4-dihydro-2H-quinolinyl, 2,4-dioxo-3,4-dihydro-2H-quinazolinyl, 1,2,3,4,5,6-hexahydro[2,2']bipyridinylyl, 3-oxo-2,3-dihydrobenzo[1,4]-oxazinyl, 5,6,7,8-tetrahydroquinolinyl, and the like.

"Heterocycloalkyl" means cycloalkyl, as defined in this application, provided that one or more of the ring carbon atoms indicated are replaced by a heteroatom moiety selected from —N═, —NR—, —O—, —S— or —S(O)$_2$—, wherein R is hydrogen, (C$_{1-6}$)alkyl, a protecting group or represents the free valence which serves as the point of attachment to a ring nitrogen, and any carbocyclic ketone, thioketone or iminoketone derivative thereof (e.g., the term hetero(C$_{5-10}$)cycloalkyl includes imidazolidinyl, morpholinyl, piperazinyl, piperidyl, pyrrolidinyl, pyrrolinyl, quinuclidinyl, and the like. A ketone derivative of piperazinyl would be 3-oxo-piperazin-1-yl). Suitable protecting groups include tert-butoxycarbonyl, benzyloxycarbonyl, benzyl, 4-methoxybenzyl, 2-nitrobenzyl, and the like. Both the unprotected and protected derivatives fall within the scope of the invention.

"Hydroxy" means the radical —OH. Unless indicated otherwise, the compounds of the invention containing hydroxy radicals include protected derivatives thereof. Suitable protecting groups for hydroxy moieties include benzyl and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Iminoketone derivative" means a derivative containing the moiety —C(NR)—, wherein R is hydrogen or (C$_{1-6}$) alkyl.

"Isomers" mean compounds of Formula (Ia) or (Ib) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "ienantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this application to describe compounds of Formula (Ia) or (Ib) are meant to be encompassed all possible stereoisomers. Thus, for example, the name N-[1-(1-benzylcarbamoyl-methanoyl)-propyl]-4-morpholin-4-yl-4-oxo-2-benzyl-sulfonylmethyl-butyramide is meant to include N-[(S)-1-(1-benzylcarbamoyl-methanoyl)-propyl]-4-morpholin-4-yl-4-oxo-2-benzylsulfonylmethyl-butyramide and N-[(R)-1-(1-benzylcarbamoyl-methanoyl)-propyl]-4-morpholin-4-yl-4-oxo-2-benzylsulfonylmethyl-butyramide and any mixture, racemic or otherwise, thereof.

Additionally, compounds of Formula (Ia) and (Ib) may exist as tautomers. Such tautomeric forms (individual tautomers or mixtures thereof) are within the scope of this invention. For example, a compound of Formula (Ia) where $R^2$ is hydrogen can tautomerize to give a compound of Formula (Ib) where $R^{4a}$ is hydrogen and vice versa as shown below.

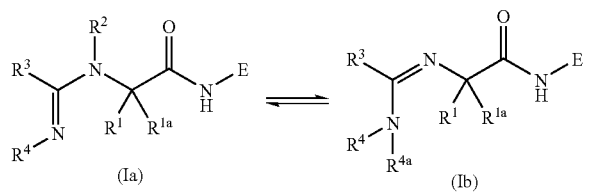

Similarly, a compound of Formula (Ib) where $R^4$ is hydrogen can tautomerize to give a compound of Formula (Ib') as shown below:

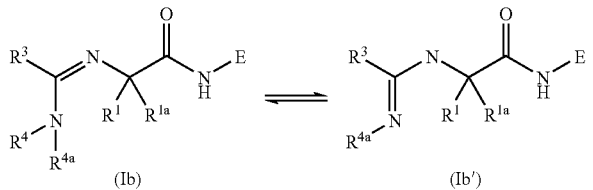

It will be recognized by a person skilled in the art that the amounts of tautomers will vary based on certain conditions such as steric interactions, electronic effects of substituents, solvent polarity, hydrogen bonding capability, temperature, pH, and the like.

"Ketone derivative or oxo" means a derivative containing the moiety —C(O)—.

"Nitro" means the radical —NO$_2$.

"Optional" or "optionally" or "may be" means that the subsequently described event or circumstance may or may not occur, and that the description includes instances where the event or circumstance occurs and instances in which it does not. For example, the phrase "wherein $R^3$, $R^4$ and $R^{21}$ may be substituted further by 1 to 5 radicals . . . " means that $R^3$, $R^4$ and/or $R^{21}$ may or may not be substituted in order to fall within the scope of the invention.

The present invention also includes N-oxide derivatives of a compound of Formula (Ia) or (Ib). N-oxide derivatives means derivatives of compounds of Formula (Ia) or (Ib) in which nitrogens are in an oxidized state (i.e., N→O) e.g., pyridine oxide, and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (Ia) or (Ib) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methylsulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (Ia) or (Ib). Prodrug means a compound that is convertible in vivo by metabolic means (e.g. by hydrolysis) to a compound of Formula (Ia) or (Ib). For example an ester of a compound of Formula (Ia) or (Ib) containing a hydroxy group may be convertible by hydrolysis in vivo to the parent molecule. Alternatively an ester of a compound of Formula (Ia) or (Ib) containing a carboxy group may be convertible by hydrolysis in vivo to the parent molecule. Suitable esters of compounds of Formula (Ia) or (Ib) containing a hydroxy group, are for example acetates, citrates, lactates, tartrates, malonates, oxalates, salicylates, propionates, succinates, fumarates, maleates, methylenebis-b-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (Ia) or (Ib) containing a carboxy group, are for example those described by Leinweber, F. J. Drug Metab. Res., 1987, 18, page 379. An especially useful class of esters of compounds of Formula (Ia) or (Ib) containing a hydroxy group, may be formed from acid moieties selected from those described by Bundgaard et al., J. Med. Chem., 1989, 32, pg. 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula (Ia) or (Ib) in which a reactive site or sites are blocked with protecting groups. Protected derivatives of compounds of Formula (Ia) or (Ib) are useful in the preparation of compounds of Formula (Ia) or (Ib) or in themselves may be active cathepsin S inhibitors. A comprehensive list of suitable protecting groups can be found in T. W. Greene, *Protecting Groups in Organic Synthesis*, 3rd edition, John Wiley & Sons, Inc. 1999.

"Ring system" as used herein means a monocyclic, bridged, or fused bicyclic ring.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

preventing the disease from occurring in an animal which may be predisposed to the disease but does not yet experience or display the pathology or symptomatology of the disease, inhibiting the disease in an animal that is experiencing or displaying the pathology or symptomatology of the diseased (i.e., arresting further development of the pathology and/or symptomatology), or ameliorating the disease in an animal that is experiencing or displaying the pathology or symptomatology of the diseased (i.e., reversing the pathology and/or symptomatology).

PREFERRED EMBODIMENTS

While the broadest definition of this invention is set forth in the Summary of the Invention in group (1), certain compounds of Formula (Ia) and (Ib) within this group and subgroups (2) and (3) are preferred. For example:

(I). A preferred group of compounds is that wherein $R^3$ is not hydrogen and when $R^{4a}$ is heteroaryl it is furanyl, thienyl, pyrrolyl, imidazolyl, pyridinyl, or pyrimidinyl.

A. Within this preferred group (I), a more preferred group of compounds is that wherein E is —$C(R^5)(R^6)X^1$ in which:

$R^5$ is hydrogen or $(C_{1-6})$alkyl, preferably hydrogen; and $R^6$ is hydrogen, —$X^2OR^{13}$ or —$R^{15}$ where $X^2$ is $(C_{1-6})$alkylene, $R^{13}$ is hydrogen, $(C_{1-6})$alkyl or halo-substituted $(C_{1-6})$alkyl and $R^{15}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-12})$bicycloaryl$(C_{0-6})$alkyl or hetero$(C_{8-12})$bicycloaryl$(C_{0-6})$alkyl wherein said aryl, heteroaryl, cycloalkyl or heterocycloalkyl may be substituted with 1 to 3 radicals independently selected from $(C_{1-6})$alkyl, cyano, halo, halo-substituted $(C_{1-4})$alkyl, nitro, —$X^8NR^{28}R^{28a}$, —$X^8NR^{28}C(O)R^{28a}$, —$X^8NR^{28}C(O)OR^{28a}$, —$X^8NR^{28}C(O)NR^{28a}R^{28b}$, —$X^8NR^{28}C(NR^{28a})NR^{28b}R^{28c}$, —$X^8OR^{29}$, —$X^8SR^{29}$, —$X^8C(O)OR^{28}$, —$X^8C(O)R^{29}$, —$X^8OC(O)R^{29}$, —$X^8C(O)NR^{28}R^{28a}$, —$X^8S(O)_2NR^{28}R^{28a}$, —$X^8NR^{28}S(O)_2R^{29}$, —$X^8P(O)(OR^{28})OR^{28a}$, —$X^8OP(O)(OR^{28})OR^{28a}$, —$X^8S(O)R^{30}$ and —$X^8S(O)_2R^{30}$ wherein $X^8$ is a bond or $(C_{1-6})$alkylene; $R^{28}$, $R^{28a}$, $R^{28b}$ and $R^{28c}$ at each occurrence independently is hydrogen or $(C_{1-6})$alkyl, $R^{29}$ is hydrogen, $(C_{1-6})$alkyl or halo-substituted $(C_{1-6})$alkyl, and $R^{30}$ is $(C_{1-6})$alkyl or halo-substituted $(C_{1-6})$alkyl; preferably ethyl; and $X^1$ is —CHO, —$C(O)R^{10}$, —$C(O)CF_3$, —$C(O)CF_2CF_2R^9$—CH=CHS(O)$_2R^{10}$, —$C(O)CF_2C(O)NR^{10}R^{11}$, —$C(O)C(O)NR^{10}R^{11}$, —$C(O)CH_2OR^{10}$, —$C(O)CH_2N(R^{11})SO_2R^{10}$, —$C(O)C(O)N(R^{11})(CH_2)_2OR^{11}$, —$C(O)C(O)N(R^{11})(CH_2)_2NHR^{11}$ or —$C(O)C(O)R^{10}$; wherein $R^{10}$ is $(C_{1-4})$ saturated alkyl, $(C_{6-10})$aryl$(C_{0-6})$ saturated alkyl, hetero$(C_{4-10})$aryl$(C_{0-6})$ saturated alkyl, $(C_{4-10})$cycloalkyl$(C_{0-6})$ saturated alkyl or hetero$(C_{4-10})$ saturated cycloalkyl$(C_{0-6})$ alkyl, $R^{11}$ is hydrogen or $(C_{1-6})$alkyl and $R^9$ is halo.

Preferably, E is —$CHR^6C(O)R^{10}$ where $R^6$ is saturated alkyl, preferably ethyl, propyl, butyl, more preferably ethyl, and $R^{10}$ is hetero$(C_{4-10})$aryl optionally substituted with $(C_{3-10})$cycloalkyl, $(C_{6-10})$aryl [optionally substituted with —$NR^{28}R^{28a}$, —$OR^{29}$, or halo substituted $(C_{1-4})$ saturated alkyl], hetero$(C_{5-10})$aryl, $(C_{1-6})$ saturated alkyl, halo-substituted $(C_{1-4})$ saturated alkyl, or —$X^8OR^{29}$ where $X^8$ is $(C_{1-6})$ saturated alkylene, $R^{28}$ and $R^{28a}$ are independently hydrogen or $(C_{1-6})$ saturated alkyl, $R^{29}$ is hydrogen, $(C_{1-6})$ saturated alkyl, or halo-substituted $(C_{1-6})$ saturated alkyl. More preferably, $R^{10}$ is benzoxazol-2-yl, oxazolo[4,5-b]pyridin-2-yl, 2-pyridin-3-yl-[1,3,4]-oxadiazol-5-yl, 2-pyridin-4-yl-[1,3,4]-oxadiazol-5-yl, 2-ethyl-[1,3,4]-oxadiazol-5-yl, 2-isopropyl-[1,3,4]-oxadiazol-5-yl, 2-tert-butyl-[1,3,4]-oxadiazol-5-yl, 2-phenyl-[1,3,4]-oxadiazol-5-yl, 2-methoxymethyl-[1,3,4]-oxadiazol-5-yl, 2-furan-2-yl-[1,3,4]-oxadiazol-5-yl, 2-thien-2-yl-[1,3,4]-oxadiazol-5-yl, 2-(4-methoxyphenyl)-[1,3,4]-oxadiazol-5-yl, 2-(2-methoxyphenyl)-[1,3,4]-oxadiazol-5-yl, 2-(3-methoxyphenyl)-[1,3,4]-oxadiazol-5-yl, 2-(2-trifluoromethylphenyl)-[1,3,4]-oxadiazol-5-yl, 2-(3-trifluoromethylphenyl)-[1,3,4]-oxadiazol-5-yl, 2-(4-trifluoromethylphenyl)-[1,3,4]-oxadiazol-5-yl, 2-(4-dimethylaminophenyl)-[1,3,4]-oxadiazol-5-yl, pyradizin-3-yl, pyrimidin-2-yl, 3-phenyl-[1,2,4]-oxadiazol-5-yl, 3-ethyl-[1,2,4]-oxadiazol-5-yl, 3-cyclopropyl-[1,2,4]-oxadiazol-5-yl, 3-thien-3-yl-[1,2,4]-oxadiazol-5-yl, 3-pyridin-4-yl-[1,2,4]-oxadiazol-5-yl, 3-pyridin-2-yl-[1,2,4]-oxadiazol-5-yl, 5-ethyl-[1,2,4]-oxadiazol-3-yl, 5-phenyl-[1,2,4]-oxadiazol-3-yl, 5-thien-3-yl-[1,2,4]-oxadiazol-3-yl, 5-trifluoromethyl-[1,2,4]-oxadiazol-3-yl, 5-pyridin-4-yl-[1,2,4]-oxadiazol-3-yl, or 5-phenyloxazol-2-yl. Even more preferably, $R^{10}$ is benzoxazol-2-yl, oxazolo[4,5-b]pyridin-2-yl, 2-pyridin-3-yloxadiazol-5-yl, 2-pyridin-4-yl-[1,3,4]-oxadiazol-5-yl, 2-ethyl-[1,3,4]-oxadiazol-5-yl, 2-phenyl-[1,3,4]-oxadiazol-5-yl, benzimidazol-2-yl, pyradizin-3-yl, pyrimidin-2-yl, 3-phenyl-[1,2,4]-oxadiazol-5-yl, or 3-ethyl-[1,2,4]-oxadiazol-5-yl, most preferably $R^{10}$ is benzoxazol-2-yl.

B. Within this preferred group (I), another more preferred group of compounds is that wherein E is —$C(R^5)(R^6)X^1$ in which $R^5$ and $R^6$ taken together with the carbon atom to which both $R^5$ and $R^6$ are attached form $(C_{3-8})$cycloalkylene or hetero$(C_{3-8})$cycloalkylene, preferably cyclopropylene, cyclopentylene, cyclohexylene, thiomorpholinyl-1-dioxide, tetrahydropyran-4-yl, tetrahydrothiopyran-4-yl, tetrahydropyran-4-yl-1-oxide, tetrahydropyran-4-yl,-1,1-dioxide, or piperidin-4-yl wherein the nitrogen atom is optionally substituted with alkyl or hydroxy. More preferably, $R^5$ and $R^6$ taken together with the carbon atom to which both $R^5$ and $R^6$ are attached form cyclohexyl, thiomorpholino dioxide, tetrahydropyran-4-yl, or piperidinyl wherein the nitrogen atom is optionally substituted with 1 to 2 radicals independently selected from $(C_{1-6})$alkyl and hydroxy and $X^1$ is —CHO, —$C(O)R^{10}$, —$C(O)CF_3$, —$C(O)CF_2CF_2R^9$—CH=CHS(O)$_2R^{10}$, —$C(O)CF_2C(O)NR^{10}R^{11}$, —$C(O)C(O)NR^{10}R^{11}$, —$C(O)C(O)OR^{10}$, —$C(O)CH_2OR^{10}$, —$C(O)CH_2N(R^{11})SO_2R^{10}$, —$C(O)C(O)N(R^{11})(CH_2)_2OR^{11}$, —$C(O)C(O)N $(R^{11})(CH_2)_2NR^1_{10}$ or —C(O)C(O)$R^{10}$. More preferably, —C(O)C(O)$NR^1R^{11}$ where $R^{11}$ is hydrogen and $R^{10}$ is benzyl.

C. Within this preferred group (I), yet another more preferred group of compounds is that wherein E is a group of formula (a):

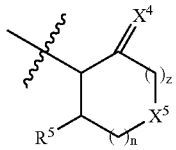

in which:

n is 0, 1, or 2, z is 0 or 1, $X^4$ is $NR^{19}$, O or S where $R^{19}$ is hydrogen or $(C_{1-6})$alkyl; $X^5$ is —O—, —S(O)$_2$—, —S— or —$NR^{20}$— where $R^{20}$ is selected from hydrogen, $(C_{1-6})$alkyl, —$X^6C(O)OR^{22}$, —$X^6C(O)R^{23}$, —$X^6S(O)_2R^{24}$, —$X^6C(O)OR^{25}$, —$X^6C(O)R^{25}$ and —$X^6S(O)_2R^{25}$ in which $X^6$ is a bond or $(C_{1-6})$alkylene; $R^{22}$ is hydrogen or $(C_{1-6})$alkyl; $R^{23}$ is hydrogen, $(C_{1-6})$alkyl or halo-substituted$(C_{1-6})$alkyl, $R^{24}$ is $(C_{1-6})$alkyl or halo-substituted$(C_{1-6})$alkyl, and $R^{25}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-12})$bicycloaryl$(C_{0-6})$alkyl or hetero$(C_{8-12})$bicycloaryl$(C_{0-6})$alkyl;

and furthermore within (a) any cycloalkyl or heterocycloalkyl may be substituted further with 1 to 5 radicals independently selected from $(C_{1-6})$alkyl, cyano, halo, halo-substituted$(C_{1-4})$alkyl, nitro, —$X^8NR^{28}R^{28a}$, —$X^8NR^{28}C(O)R^{28a}$, —$X^8NR^{28}C(O)OR^{28a}$, —$X^8NR^{28}C(O)NR^{28a}R^{28b}$, —$X^8NR^{28}C(NR^{28a})NR^{28b}R^{28c}$, —$X^8OR^{29}$, —$X^8SR^{29}$, —$X^8C(O)OR^{28}$, —$X^8C(O)R^{29}$, —$X^8OC(O)R^{29}$, —$X^8C(O)NR^{28}R^{28a}$, —$X^8S(O)NR^{28}R^{28a}$, —$X^8NR^{28}S(O)_2R^{29}$, —$X^8P(O)(OR^{28})OR^{28a}$, —$X^8OP(O)(OR^{28})OR^{28a}$, —$X^8S(O)R^{30}$ and —$X^8S(O)_2R^{30}$ wherein $X^8$ are independently a bond or $(C_{1-6})$alkylene; $R^{28}$, $R^{28a}$, $R^{28b}$ and $R^{28c}$ at each occurrence independently is hydrogen or $(C_{1-6})$alkyl, $R^{29}$ is hydrogen, $(C_{1-6})$alkyl or halo-substituted$(C_{1-6})$alkyl, and $R^{30}$ is $(C_{1-6})$alkyl or halo-substituted$(C_{1-16})$alkyl and/or $R^y$ selected from —$R^{26}$, —$OR^{26}$, —$SR^{26}$, —$S(O)R^{26}$, —$S(O)_2R^{26}$, —$C(O)R^{26}$, —$C(O)OR^{26}$, —$OC(O)R^{26}$, —$NR^{26}R^{27}$, —$N^{27}C(O)OR^{26}$, —$NR^{27}C(O)R^{26}$, —$C(O)NR^{26}R^{27}$, —$S(O)_2NR^{26}R^{27}$, —$NR^{27}S(O)_2R^{26}$, —$NR^{27}C(O)NR^{26}R^{27a}$ and $NR^{27}C(NR^{27a})NR^{26}R^{27b}$ where $R^{26}$, $R^{27}$, $R^{27a}$, and $R^{27b}$ are as defined in the Summary of the Invention.

(a) Within the above preferred and more preferred groups (I)(A–C), an even more preferred group of compounds is that wherein:

$R^1$ is —$CH_2X^9$ wherein $X^9$ is selected from —$X^{10}SR^{33}$, —$X^{10}C(O)NR^{33}R^{33a}$, —$X^{10}S(O)_2R^{34}$, —$X^{10}COR^{34}$, —$X^{10}OR^{33}$, —$R^{35}$, —$X^{10}SR^{35}$, —$X^{10}S(O)_2R^{35}$, —$X^{10}C(O)R^{35}$, or —$X^{10}C(O)NR^{33}R^{35}$ wherein $X^{10}$ is a bond or $(C_{1-6})$alkylene; $R^{33}$ and $R^{33a}$ at each occurrence independently is hydrogen, $(C_{1-6})$alkyl or halo-substituted$(C_{1-6})$alkyl; $R^{34}$ is $(C_{1-6})$alkyl or halo-substituted$(C_{1-6})$alkyl; and $R^{35}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-10})$bicycloaryl$(C_{0-6})$alkyl or hetero$(C_{8-10})$bicycloaryl$(C_{0-6})$alkyl wherein within $R^1$ any alicyclic or aromatic ring is optionally substituted with one, two, or three radicals independently selected from $(C_{1-6})$ saturated alkyl, benzyl, cyano, halo, halo-substituted$(C_{1-4})$ saturated alkyl, —$OR^{36}$, or —$R^{38}$ where $R^{36}$ is $(C_{1-6})$ saturated alkyl or halo-substituted$(C_{1-6})$ saturated alkyl and $R^{38}$ is $(C_{6-10})$ aryl and within $R^1$ any aliphatic moiety is unsubstituted or substituted further by 1 or 2 halo; and $R^{1a}$ is hydrogen.

Preferably, $R^1$ is thiophen-2-ylsulfonylmethyl, 3-chloro-2-fluorophenylmethane-sulfonylmethyl, benzenesulfonylmethyl, phenylmethanesulfonylmethyl, 2-(1,1-difluoromethoxy)phenylmethanesulfonylmethyl, 2-benzenesulfonylethyl, 2-(pyridin-2-ylsulfonyl)ethyl, 2-(pyridin-4-ylsulfonyl)ethyl, 2-phenylmethane-sulfonylethyl, oxypyridin-2-ylmethanesulfonylmethyl, prop-2-ene-1-sulfonylmethyl, 4-methoxyphenylmethanesulfonyl-methyl, p-tolylmethanesulfonymethyl, 4-chlorophenylmethanesulfonylmethyl, o-tolylmethanesulfonylmethyl, 3,5-dimethylphenylmethanesulfonylmethyl, 4-trifluoromethylphenylmethane-sulfonylmethyl, 4-trifluoromethoxyphenylmethanesulfonylmethyl, 2-bromophenylmethanesulfonylmethyl, pyridin-2-ylmethanesulfonyl-methyl, pyridin-3-ylmethanesulfonylmethyl, pyridin-4-ylmethanesulfonylmethyl, naphthalen-2-ylmethanesulfonylmethyl, 3-methylphenylmethanesulfonylmethyl, 3-trifluoromethylphenylmethanesulfonylmethyl, 3-trifluoromethoxyphenylmethanesulfonylmethyl, 4-fluoro-2-trifluoromethoxyphenylmethanesulfonylmethyl, 2-fluoro-6-trifluoromethylphenylmethanesulfonylmethyl, 3-chlorophenylmethanesulfonylmethyl, 2-fluorophenylmethanesulfonylmethyl, 2-trifluoromethylphenylmethanesulfonylmethyl, 2-cyanophenylmethanesulfonylmethyl, 4-tert-butylphenylmethanesulfonylmethyl, 2-fluoro-3-methylphenylmethanesulfonyl-methyl, 3-fluorophenylmethanesulfonylmethyl, 4-fluorophenylmethanesulfonylmethyl, 2-chlorophenylmethanesulfonylmethyl, 2,5-difluorophenylmethanesulfonylmethyl, 2,6-difluorophenylmethanesulfonylmethyl, 2,5-dichlorophenylmethanesulfonylmethyl, 3,4-dichlorophenylmethanesulfonylmethyl, 3-cyanophenylmethanesulfonylmethyl, 2-trifluoromethoxyphenylmethanesulfonylmethyl, 2,3-difluorophenylmethanesulfonylmethyl, 2,5-difluorophenylmethanesulfonylmethyl, biphenyl-2-ylmethanesulfonylmethyl, cyclohexylmethyl, 3-fluorophenyl-methanesulfonylmethyl, 3,4-difluorophenylmethanesulfonylmethyl, 2,4-difluorophenylmethanesulfonylmethyl, 2,4,6-trifluorophenylmethanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonyl-methyl, 2-chloro-5-trifluoromethylphenylmethanesulfonylmethyl, 2-methylpropane-1-sulfonyl, 2-fluoro-3-trifluoromethylphenylmethanesulfonylmethyl, 2-fluoro-4-trifluoromethylphenylmethanesulfonylmethyl, 2-fluoro-5-trifluoromethyl-phenylmethanesulfonylmethyl, 4-fluoro-3-trifluoromethylphenylmethanesulfonylmethyl, 2-methoxyphenylmethanesulfonylmethyl, 3,5-bis-trifluoromethylphenyl-methanesulfonylmethyl, 4-difluoromethoxyphenylmethanesulfonylmethyl, 2-difluoro-methoxyphenylmethanesulfonylmethyl, 3-difluoromethoxyphenylmethanesulfonylmethyl, 2,6-dichlorophenylmethanesulfonylmethyl, biphenyl-4-ylmethanesulfonylmethyl, 3,5-dimethylisoxazol-4-ylmethanesulfonylmethyl, 5-chlorothien-2-ylmethanesulfonylmethyl, 2-[4-(1,1-difluoromethoxy)benzenesulfonyl]ethyl, 2-[2-(1,1-difluoromethoxy)benzenesulfonyl]ethyl, 2-[3-(1,1-difluoromethoxy)benzenesulfonyl]ethyl, 2-(4-trifluoromethoxybenzenesulfonyl)ethyl, 2-(3-trifluoromethoxybenzenesulfonyl)ethyl, 2-(2-trifluoromethoxy-benzenesulfonyl)ethyl, (cyanomethylmethylcarbamoyl)methyl, biphenyl-3-ylmethyl, 2-oxo-2-pyrrolidin-1-ylethyl, 2-benzenesulfonylethyl, isobutylsulfanylmethyl, 2-phenylsulfanylethyl, cyclohexylmethanesulfonylmethyl, 2-cyclohexylethanesulfonyl-methyl, benzyl, naphthalen-2-yl, phenylmethanesulfanylmethyl, 2-trifluoromethylphenylmethanesulfanylmethyl, 2-phenylsulfanylethyl, cyclopropylmethanesulfonylmethyl, 5-bromothien-2-ylmethyl, 3-phenylpropyl, 2,2-difluoro-3-phenylpropyl, 3,4,5-trimethoxyphenylmethanesulfonylmethyl, 2,2-difluoro-3-thien-2-ylpropyl, cyclohexylethyl, cyclohexylmethyl, tert-butylmethyl, 1-methylcyclohexylmethyl, 1-methylcyclopentyl-methyl, 2,2-difluoro-3-phenylpropyl, 2,2-dimethyl-3-phenylpropyl, 1-benzylcyclopropylmethyl, benzyloxymethyl, —$X^{10}S(O)_2R^{34}$ and —$X^{10}S(O)_2R^{35}$ wherein $R^{13}$ is alkyl and $R^{14}$ is phenyl which phenyl is unsubstituted or substituted.

More preferably, $R^1$ is 2-cyclohexylethyl, cyclohexylmethyl, cyclopentylmethyl, 2-cyclopentylethyl, tert-butylmethyl, 1-methylcyclopropylmethyl, 1-methylcyclohexyl-methyl, 1-methylcyclopentylmethyl, 1,3-dimethylcyclopentylmethyl, morpholin-4-ylmethyl, 2,2-dimethyl-3-phenylpropyl, 1-benzylcyclopropylmethyl, 2-(1,1-difluoromethoxy)phenylmethanesulfonylmethyl, 2-methylpropylsulfonylmethyl, phenylmethanesulfonylmethyl, pyridin-2-ylmethanesulfonyl-methyl, pyridin-4-ylmethanesulfonylmethyl, cyclopropylmethanesulfonylmethyl, pyridin-3-ylmethanesulfonylmethyl, 2,6-difluorophenylmethanesulfonylmethyl, 2,2-difluoro-3-phenylpropyl, 2,2-dichloropropyl, 2,2-dichloro-3-phenylpropyl, 2-pyridin-2-ylsulfonylethyl, 2-phenylsulfonylethyl, 5-bromothien-2-ylmethyl, pyridin-4-ylmethyl, 2-chlorobenzyl, or 4-fluorobenzyl. Even more preferably, $R^1$ is 2-cyclohexylethyl, cyclohexylmethyl, tert-butylmethyl, 1-methylcyclohexylmethyl, 1-methylcyclopentylmethyl, 2,2-difluoro-3-phenylpropyl, 2,2-dimethyl-3-phenylpropyl, 1-benzylcyclopropylmethyl, —$X^{10}S(O)_2R^{34}$ or —$X^{10}S(O)_2R^{35}$, wherein $R^{34}$ is alkyl and $R^{35}$ is phenyl which phenyl is unsubstituted or substituted. Preferably, the stereochemistry at the carbon atom to which the $R^1$ group is is attached is (S) when the Prelog rule places the order of the substituent 1) N, 2)—COOH, 3) $R^1$ and 4) H; and (R) when the Prelog rule places the order of the substituent 1) N, 2) $R^1$, 3) —COOH and 4) H except when $R^1$ is pyridin-4-ylmethyl, 4-fluorobenzyl or 2-chlorobenzyl, the stereochemistry at at the carbon atom to which these groups are attached is (R).

(b) Yet another more preferred group of compounds within groups (I)(A–C) is that wherein $R^1$ is $(C_{1-10})$alkyl or —$CH_2X^9$ where $X^9$ is $R^{35}$ where $R^{35}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-10})$bicycloaryl$(C_{0-6})$alkyl or hetero$(C_{8-10})$bicycloaryl$(C_{0-6})$alkyl. More preferably $R^1$ is 2-methylpropyl, 2,4,4-trimethylpentyl, 4-methylindol-3-ylmethyl, 2-napth-1-ylpropyl, 2-phenyl-prop-2-enyl, 2-phenyl-2-methylpropyl, 2-phenylpropyl, 2-phenylbutyl wherein the phenyl group in 2-phenylprop-2-enyl, 2-phenyl-2-methylpropyl, 2-phenylpropyl, or 2-phenylbutyl is optionally substituted with one or two substituents independently selected from $(C_{1-6})$alkyl, halo, haloalkoxy, or alkoxy, and benzyl where the phenyl ring is substituted with two halo groups, more preferably methyl, chloro, fluoro, trifluoromethoxy, or methoxy. Even more preferably, 2-methylpropyl, 2,4,4-trimethylpentyl, 2-napth-1-ylpropyl, 2-phenylprop-2-enyl, 2-phenyl-2-methylpropyl, 2-phenylpropyl, 2-(2-methoxyphenyl)propyl, 4-methyl-indol-3-ylmethyl, 2-(2,5-dimethylphenyl)propyl, benzyloxymethyl, 2-(2,4-dimethyl-phenyl)propyl, 2-(2,4-dichlorophenyl)propyl, 2,6-difluorobenzyl, 2,5-difluorobenzyl, and 2,3-difluorobenzyl; most preferably 2,6-difluorobenzyl or 2S-phenylpropyl and the stereochemistry to which $R^1$ is attached is (S); and $R^{1a}$ is hydrogen.

(c) Yet another more preferred group of compounds within groups (I)(A–C) is that wherein $R^1$ is $(C_{1-10})$ saturated alkyl or —$C(R^{31})(R^{32})X^9$ wherein $R^{31}$ and $R^{32}$ are independently hydrogen or $(C_{1-6})$ saturated alkyl and $X^9$ is selected from —$X^{10}NR^{33}R^{33a}$, —$X^0OR^{33}$, —$X^{10}SR^{33}$, —$X^{10}C(O)OR^{33}$, —$X^{10}C(O)NR^{33}R^{33a}$, —$X^{10}S(O)R^{34}$, —$X^{10}SO_2R^{34}$, —$R^{35}$, —$X^{10}R^{35}$, —$X^{10}SR^{35}$, —$X^{10}S(O)R^{35}$, —$X^{10}S(O)_2R^{35}$, —$X^{10}C(O)R^{35}$, —$X^{10}C(O)NR^{33}R^{35}$ wherein $X^{10}$ is a bond or $(C_{1-6})$alkylene; $R^{33}$ and $R^{33a}$ at each occurrence independently is hydrogen, $(C_{1-6})$ saturated alkyl or halo-substituted$(C_{1-6})$ saturated alkyl; $R^{34}$ is $(C_{1-6})$ saturated alkyl; and $R^{35}$ is $(C_{3-10})$cycloalkyl$(C_{0-6})$ saturated alkyl, hetero$(C_{3-10})$cycloalkyl$(C_{0-3})$ saturated alkyl, $(C_{6-10})$aryl$(C_{0-6})$ saturated alkyl, hetero$(C_{5-10})$aryl$(C_{0-6})$ saturated alkyl, $(C_{1-0})$bicycloaryl$(C_{0-6})$ saturated alkyl or hetero$(C_{8-10})$bicycloaryl$(C_{0-6})$ saturated alkyl; wherein within $R^1$ any alicyclic or aromatic ring system is unsubstituted or substituted further by 1 to 2 radicals independently selected from $(C_{1-6})$ saturated alkyl, benzyl, cyano, halo, halo-substituted $(C_{1-4})$ saturated alkyl, nitro, —$OR^{36}$, —$C(O)OR^{36}$, and within $R^1$ any aliphatic moiety is unsubstituted or substituted further by 1 to 5 radicals independently selected from halo and wherein $R^{36}$ is hydrogen, $(C_{1-6})$ saturated alkyl, or halo substituted $(C_{1-6})$ saturated alkyl; and $R^{1a}$ is hydrogen.

Preferably, $R^1$ is 2-methylpropyl, 2,2-dimethylpropyl, 2,2-dichloroethyl, 2,2,2-trichloroethyl, 1,3-dimethylcyclopentylmethyl, 4,4-dimethylcyclohexylmethyl, 4-ethyl-4-methylcyclohexylmethyl, 4,4-diethylcyclohexylmethyl, 3,3-dimethylcyclohexylmethyl, 3,5-dimethylcyclohexylmethyl, 4-ethoxycarbonylpiperidin-4-ylmethyl, 4-methylpiperidin-4-ylmethyl, cycloheptylmethyl, cyclooctylmethyl, 3,3-dimethylbutyl, 3-methylbutyl, 2-cyclohexylethyl, 2,2,3-trimethylbutyl, 2-cyclohexyl-2-methylpropyl, 3,3-dimethylpentyl, 3-ethyl-3-methylpentyl, 2-(1-methylcyclohexyl)ethyl, tetrahydronaphthylmethyl, 2-tetrahydropyran-4-ylethyl, 2-(1-methylcyclopropyl)ethyl, 2-(1-methylcyclopropyl)-2-methylpropyl, cyclopentylmethyl, 2-cyclopentylethyl, 2-cyclopentyl-2-methylpropyl, 4-isopropyl-4-methylcyclohexylmethyl, phenylmethanesulfinylmethyl, dimethylaminomethyl, pyrrolidin-1-ylmethyl, piperidin-1-ylmethyl, morpholin-4-ylmethyl, thiomorpholin-4-ylmethyl, 1-oxo-thiomorpholin-4-ylmethyl, 1,1-dioxothiomorpholin-4-ylmethyl, tetrahydrothiopyran-4-ylmethyl, 1-oxotetrahydrothiopyran-4-ylmethyl, 1,1-dioxotetrahydrothiopyran-4-ylmethyl, 1-methylpiperazin-4-ylmethyl, benzyloxymethyl, n-butyl, ethoxymethyl, ethylthiomethyl, ethylsulfinylmethyl, ethylsulfonylmethyl, isopropylthiomethyl, isopropylmethanesulfonylmethyl, isopropyloxymethyl, 2-dimethylaminoethyl, 2-piperidin-1-ylethyl, 2-pyrrolidin-1-ylethyl, 2-methylthioethyl, 2-methylsulfinylethyl, 2-methysulfonylethyl, tert-butylthiomethyl, tert-butyloxymethyl, 2-(1,1-difluoromethoxy)benzyloxymethyl, benzyloxymethyl, benzyl, 4-methoxybenzyl, imidazol-4-ylmethyl, 4-dimethylaminobutyl, indol-3-ylmethyl, 2-dimethylamino-carbonylethyl, 2-pyrrolidin-1-ylcarbonylethyl, dimethylaminocarbonylmethyl, pyrrolidin-1-ylcarbonylmethyl, methoxycarbonylmethyl, 2-fluorophenylmethanesulfonylmethyl, 2-chlorophenylmethanesulfonylmethyl, 2-nitrophenylmethanesulfonylmethyl, 2-cyanophenylmethanesulfonylmethyl, pyridin-3-ylmethanesulfonylmethyl, pyridin-2-ylmethanesulfonylmethyl, pyridin-4-ylmethanesulfonylmethyl, 2-fluorophenylmethanethiomethyl, 2-chlorophenylmethanethiomethyl, 2-cyanophenylmethanethiomethyl, 2-nitrophenylmethanethiomethyl, cyclohexylmethanethiomethyl, cyclohexylsulfinylmethyl, cyclohexylmethanesulfonylmethyl, 3,4-dichlorobenzyl, 2-chlorobenzyl, 4-ethoxybenzyl, 4-nitrobenzyl, biphen-4-ylmethyl, naphth-1-ylmethyl, 2-methylbutyl, 1-methylpropyl, naphth-2-ylmethyl, 4-chlorobenzyl, 3-chlorobenzyl, 4-fluorobenzyl, indol-2-ylmethyl, 1-benzylimidazol-14-ylmethyl, 2-phenethyl, 4-hydroxybenzyl, 2-(4-hydroxyphenyl)ethyl, 4-ethyl-4-methylpiperidin-1-ylmethyl, 2-methylcyclohexylmethyl, 4-methoxycyclohexylmethyl, indol-1-ylmethyl, 1-methylpiperidin-2-ylmethyl, 2-biclyo[2.2.1]hep-3-tylethyl, 8-methyl-8-aza-bicyclo[3.2.1]oct-3-ylmethyl, bicyclo[3.2.1]oct-3-ylmethyl, bicyclo[3.1.1]hept-3-ylmethyl, 6,6-dimethylbicyclo[3.1.1]hept-3-ylmethyl, 6,6-dimethylbicyclo[3.1.1]hept-4-ylmethyl, 2-bicyclo[2.2.1]hept-1-ylethyl, bicyclo[2.2.1]hept-2-ylethyl, pyridin-4-ylmethyl, 2-chlorobenzyl, 4-fluorobenzyl, or 2,2-dichloro-3-phenylpropyl.

More preferably, $R^1$ is 2,2-dichloroethyl, 2,2,2-trichloroethyl, 1,4-dimethylcyclopentylmethyl, morpholin-4-ylmethyl, isopropylmethanesulfonylmethyl, cyclopentylmethyl, 2,2-difluoro-3-phenylpropyl, pyridin-4-ylmethyl, 2-chlorobenzyl, 4-fluorobenzyl, or 2,2-dichloro-3-phenylpropyl. Preferably, the stereochemistry at the carbon atom to which the $R^1$ group is is attached is (S) when the Prelog rule places the order of the substituent 1) N, 2)—COOH, 3) $R^1$ and 4) H; and (R) when the Prelog rule places the order of the substituent 1) N, 2) $R^1$, 3)—COOH and 4) H except when $R^1$ is pyridin-4-ylmethyl, 4-fluorobenzyl or 2-chlorobenzyl, the stereochemistry at at the carbon atom to which these groups are attached is (R).

(d) Yet another more preferred group of compounds within groups (I)(A–C) is that wherein $R^1$ and $R^{1a}$ together with the carbon atoms to which they are attached form $(C_{3-8})$cycloalkylene or hetero$(C_{3-10})$cycloalkylene ring wherein said cycloalkylene ring is optionally substituted with one or two substitutents independently selected from $(C_{1-6})$alkyl, $(C_{1-6})$alkoxy, hydroxy, halo, hydroxyalkyl, or keto and said heterocycloalkylene ring is optionally substituted with one or two substitutents independently selected from $(C_{1-6})$alkyl, $(C_{1-6})$alkoxy, hydroxyalkyl, alkoxyalkyl, aminoalkyl, acyl, $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl wherein said aryl, heteroaryl, and heterocycloalkyl are optionally substituted with one, two, or three substituents independently selected from $(C_{1-6})$alkyl, $(C_{1-6})$alkoxy, nitro, amino, halo, hydroxy, alkylthio, halo-substituted alkyl, halo-substituted alkoxy, or acyl. Preferably, $R^1$ and $R^{1a}$ together with the carbon atoms to which they are attached form 3,3-dimethylcyclobutyl, cyclohexyl, cyclopenyl, cyclooctyl, thiomorpholino-1,1-dioxide, or piperidin-4-yl wherein the nitrogen atom at the 1-position of the piperidinyl ring is optionally substituted with alkyl, —SO$_2$R where is $(C_{1-6})$alkyl, $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl where the rings may be optionally substituted with one, two, or three substitutents independently selected from alkyl, alkoxy, hydroxy, halo, alkylthio, or carboxy.

(1) Within the preferred, more preferred, and even more preferred groups above, a particularly preferred group of compounds is that wherein:

$R^3$ is $(C_{1-6})$alkyl, $(C_{3-7})$cycloalkyl, phenyl, benzyl, naphthyl, tetrahydronaphthyl, $(C_{1-6})$alkylsulfonyl$(C_{1-6})$alkyl, $(C_{3-7})$cycloalkylsulfonyl$(C_{1-6})$alkyl, arylsulfonyl$(C_{1-6})$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzothienyl, benzimidazolyl, benzthiazolyl, benzoisoxazolyl, benzoxazolyl or amino; wherein $R^3$ is optionally substituted by one, two, or three $R^a$;

each $R^a$ is independently $(C_{1-6})$alkyl, $(C_{3-6})$cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, $(C_{1-6})$alkoxy, $(C_{1-6})$alkanoyl, $(C_{1-6})$alkanoyloxy, aryloxy, benzyloxy, $(C_{1-6})$alkoxycarbonyl, aryloxycarbonyl, aroyloxy, carbamoyl wherein the nitrogen atom may be independently mono or di-substituted by $(C_{1-6})$alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each $R^a$ is independently $(C_{1-6})$alkanoylamino, aroylamino, $(C_{1-6})$alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by $(C_{1-6})$alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each $R^a$ is independently $(C_{1-6})$alkoxycarbonylamino, aryloxycarbonylamino, $(C_{1-6})$alkylcarbamoyloxy, arylcarbamoyloxy, $(C_{1-6})$alkylsulfonylamino, arylsulfonylamino, $(C_{1-6})$alkylaminosulfonyl, arylaminosulfonyl, amino wherein the nitrogen atom may be independently mono or di-substituted by $(C_{1-6})$alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each $R^a$ is independently halogen, hydroxy, oxo, carboxy, cyano, nitro, carboxamide, amidino or guanidino, $R^a$ may be further optionally substituted by one, two or three $R^b$;

each $R^b$ is independently $(C_{1-6})$alkyl, $(C_{1-6})$alkoxy, $(C_{1-6})$haloalkyl, $(C_{1-6})$haloalkoxy, aminosulfonyl, $(C_{1-6})$alkylaminosulfonyl, di$(C_{1-6})$alkylaminosulfonyl $(C_{3-6})$cycloalkyl, aryl, aryloxy, benzyloxy, halogen, hydroxy, oxo, carboxy, cyano, nitro, carboxamide, amidino or guanidino;

$R^2$ is hydrogen or methyl, preferably hydrogen;

$R^4$ is hydrogen, hydroxy, nitrile or a $(C_{1-6})$alkyl optionally partially or fully halogenated wherein one or more C atoms are optionally replaced by O, NH, S(O), S(O)$_2$ or S and wherein said chain is optionally independently substituted with 1–2 oxo groups, —NH$_2$, one or more $(C_{1-4})$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, benzoxazolyl or quinoxalinyl; and $R^{4a}$ is hydrogen, $(C_{1-5})$alkyl, $(C_{3-6})$cycloalkyl, aryl, $(C_{1-5})$alkoxy, aryloxy, benzyloxy, or —C(O)OR$^d$ where (R$^d$ is hydrogen, $(C_{1-6})$alkyl, $(C_{1-6})$alkoxy$(C_{1-6})$alkyl, $(C_{1-6})$haloalkyl, $(C_{3-7})$cycloalkyl, $(C_{3-7})$cycloalkyl$(C_{1-6})$alkyl, heteroaryl, heteroaryl$(C_{1-6})$alkyl, aryl, or aryl$(C_{1-6})$alkyl).

Preferably, $R^3$ is $(C_{1-5})$alkyl, $(C_{3-6})$cycloalkyl, phenyl, benzyl, naphthyl, $(C_{1-3})$alkylsulfonyl$(C_{1-3})$alkyl, $(C_{3-6})$cycloalkylsulfonyl$(C_{1-3})$alkyl, arylsulfonyl$(C_{1-3})$alkyl, pyrrolidinyl, piperidinyl, morpholinyl, thiomorpholinyl, piperazinyl, furanyl, thienyl, oxazolyl, thiazolyl, imidazolyl, pyridinyl, isoxazolyl, pyrimidinyl, pyrazinyl, pyridazinyl, indolyl, quinolinyl, benzofuranyl, benzothienyl, benzimidazolyl, benzthiazolyl, benzoxazolyl or amino; wherein $R^3$ is optionally substituted by one, two, or three substituents independently selected from $R^a$;

each $R^a$ is independently $(C_{1-3})$alkyl, cyclopropyl, cyclopentyl, cyclohexyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, benzthiazolyl, benzoxazolyl, $(C_{1-3})$alkoxy, $(C_{1-3})$alkanoyl, $(C_{1-3})$alkanoyloxy, aryloxy, benzyloxy, $(C_{1-3})$alkoxycarbonyl, aryloxycarbonyl, aroyloxy, carbamoyl wherein the nitrogen atom may be independently mono or di-substituted by $(C_{1-3})$alkyl, aryl, pyrrolidinyl, piperidinyl, morpholinyl, thiomorpholinyl, piperazinyl, thienyl, oxazolyl, thiazolyl, imidazolyl, pyridinyl, pyrimidinyl, benzimidazolyl or benzthiazolyl, or each $R^a$ is independently $(C_{1-3})$alkanoylamino, aroylamino, $(C_{1-3})$alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by $(C_{1-3})$alkyl, aryl, pyrrolidinyl, piperidinyl, morpholinyl, thiomorpholinyl or piperazinyl, or each $R^a$ is independently $(C_{1-3})$alkoxycarbonylamino, aryloxycarbonylamino, $(C_{1-3})$alkylcarbamoyloxy, arylcarbamoyloxy, $(C_{1-3})$alkylsulfonylamino, arylsulfonylamino, $(C_{1-3})$alkylamino-sulfonyl, arylaminosulfonyl, amino wherein the nitrogen atom may be independently mono or di-substituted by $(C_{1-3})$alkyl, aryl, pyrrolidinyl, piperidinyl, morpholinyl, thiomorpholinyl or piperazinyl, or each $R^a$ is independently halogen, hydroxy, oxo, carboxy, cyano, nitro, carboxamide, amidino, or guanidino, $R^a$ may be further optionally substituted by one, two or three $R^b$; each $R^b$ is independently $(C_{1-3})$alkyl, aryl, $(C_{1-3})$alkoxy, $(C_{1-3})$haloalkyl, $(C_{1-3})$haloalkoxy, aryloxy, benzyloxy, halogen, hydroxy, oxo, carboxy, cyano, nitro, carboxamide, amidino or guanidino.

Even more preferably, $R^3$ is $(C_{1-5})$alkyl, $(C_{3-6})$cycloalkyl, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzothienyl, benzimidazolyl, benzthiazolyl, benzoxazolyl or amino; wherein $R^3$ is optionally substituted by one, two or three $R^a$;

each $R^a$ is independently $(C_{1-3})$alkyl, cyclopropyl, cyclohexyl, phenyl, pyrrolidinyl, piperidinyl, morpholinyl, thiomorpholinyl, piperazinyl, thienyl, imidazolyl, $(C_{1-3})$alkoxy, $(C_{1-3})$alkanoyl, $(C_{1-3})$alkanoyloxy, aryloxy, benzyloxy, $(C_{1-3})$alkoxycarbonyl, aryloxycarbonyl, aroyloxy, carbamoyl wherein the nitrogen atom may be independently mono or di-substituted by $(C_{1-3})$alkyl, aryl, pyrrolidinyl, piperidinyl, morpholinyl, thiomorpholinyl or piperazinyl, or each $R^a$ is independently $(C_{1-3})$alkanoylamino, aroylamino, $(C_{1-3})$alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by $C(C_{1-3})$alkyl, aryl, pyrrolidinyl, piperidinyl, morpholinyl, thiomorpholinyl or piperazinyl, or each $R^a$ is independently $(C_{1-3})$alkoxycarbonylamino, aryloxycarbonylamino, $(C_{1-3})$alkylcarbamoyloxy, arylcarbamoyloxy, $(C_{1-3})$alkylsulfonylamino, arylsulfonylamino, $(C_{1-3})$alkylaminosulfonyl, arylaminosulfonyl, amino wherein the nitrogen atom may be independently mono or di-substituted by $(C_{1-3})$alkyl, aryl, pyrrolidinyl, piperidinyl, morpholinyl, thiomorpholinyl or piperazinyl, or each $R^a$ is independently halogen, hydroxy, oxo, carboxy, cyano, nitro, carboxamide, amidino or guanidino, $R^a$ may be further optionally substituted by one, two or three $R^b$;

each $R^b$ is independently methyl, ethyl, n-propyl, i-propyl, phenyl, methoxy, ethoxy, n-propoxy, i-propoxy, phenoxy, benzyloxy, fluoro, chloro, bromo, iodo, hydroxy, trifluoromethyl, trifluoromethoxy, oxo, carboxy, cyano, nitro or carboxamide.

Even more preferably, $R^3$ is cyclopropyl, cyclopentyl, cyclohexyl, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl, or amino; wherein $R^3$ is optionally substituted by one, two or three $R^a$;

each $R^a$ is independently phenyl, pyrrolidinyl, piperidinyl, morpholinyl, thiomorpholinyl, piperazinyl, pyridinyl, thienyl, or imidazolyl; $R^a$ may be further optionally substituted by one, two or three $R^b$; each $R^b$ is independently methyl, chloro, fluoro, hydroxy, methoxy, trifluoromethyl or trifluoromethoxy.

Particularly preferably, $R^3$ is a group of formula (i)–(xiii):

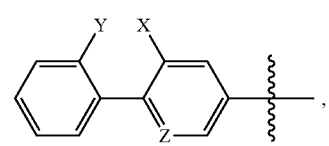

(i)

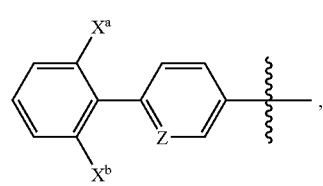

(ii)

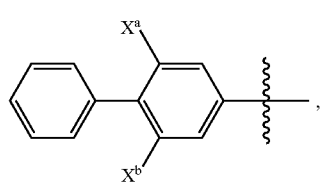

(iii)

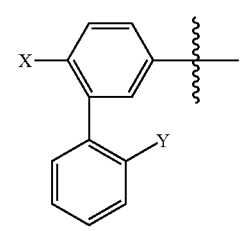

(iv)

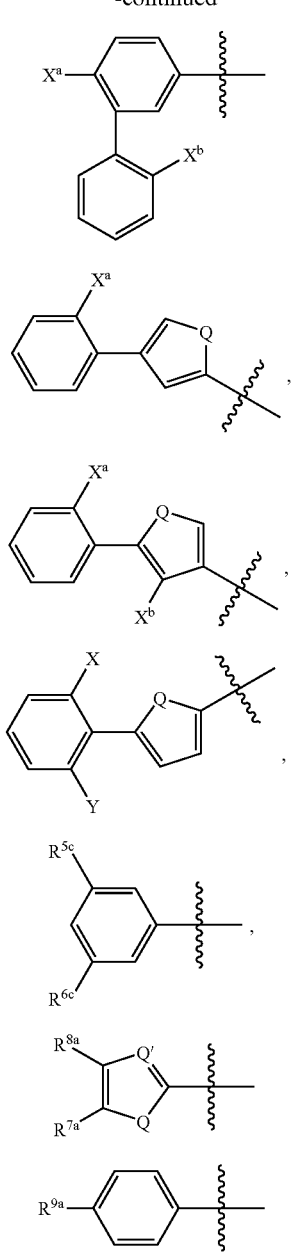

(xii) 1-(4-aminosulfonylphenyl)-5-(4-chlorophenyl)pyrazol-3-yl; or (xiii) 1-methyl-3-trifluoro-1H-thieno[2,3-c]pyrazol-4-yl;
where:

Z is —CH— or —N—;

Q is —NR— where R is hydrogen or alkyl, —O—, or —S—;

Q' is —CH— or —N—;

X and Y are independently selected from hydrogen, halo, alkyl, alkoxy, or haloalkoxy provided that one of X and Y is not hydrogen;

$X^a$ and $X^b$ are independently selected from alkyl, halo, alkoxy, or haloalkoxy;

$R^{5c}$ and $R^{6c}$ are independently selected from phenyl, 2-alkoxyphenyl, 3-alkoxyphenyl, 2-halophenyl, 2-alkylphenyl, 2-haloalkoxyphenyl, furan-2-yl, thiophen-3-yl, or pyridin-4-yl;

$R^{7a}$ and $R^{8a}$ are independently selected from phenyl, 2-alkoxyphenyl, 3-alkoxyphenyl, 2-halophenyl, 2-alkylphenyl, 2-haloalkoxyphenyl, furan-2-yl, thiophen-3-yl, or pyridin-4-yl; and $R^{9a}$ is a branched alkyl chain of 4–6 carbon atoms or trifluoroalkoxy.

Preferably, X and Y are independently selected from hydrogen, chloro, methyl, methoxy, triflurormethyl, or trifluoromethoxy, preferably hydrogen, chloro, methyl, or methoxy; and $X^a$, and $X^b$ are independently selected from methyl, chloro, fluoro, methoxy, trifluoromethyl, or trifluoromethoxy, preferably chloro, methyl, or methoxy.

More particularly, $R^3$ is 2'-chlorobiphen-4-yl, 3,2'-dichlorobiphenyl-4-yl, 2',6'-dichlorobiphen-4-yl, 2',6'-dimethylbiphen-4-yl, 2'-methylbiphen-4-yl, 2'-fluorobiphen-4-yl; 4-trifluoromethoxyphenyl, 4-(2-butyl)phenyl, 3,5-diphenylphenyl, 2,3-diphenylthiophen-5-yl, 2-(2-methylphenyl)furan-5-yl, 2-(2-methoxyphenyl)furan-5-yl, 3-methoxy-2-(2-methylphenyl)thiophen-4-yl, 3-methoxy-2-(2-methoxyphenyl)thiophen-4-yl, 2,3-di(2-methoxyphenyl)thiophen-5-yl, 3,5-di(2-methoxyphenyl)phenyl, 3,5-di(3-methoxyphenyl)phenyl, 3,5-di(thiophen-3-yl)phenyl, 3,5-di(pyridin-4-yl)phenyl, 2,3-di(2-methylphenyl)thiophen-5-yl, tert-butylphenyl, 2,3-di(furan-2-yl)thiophen-5-yl, 3,5-di(furan-2-yl)phenyl, 4-(2-methylphenyl)thiophen-2-yl, 4-(2-methoxyphenyl)thiophen-2-yl, 2'-chlorobiphen-3-yl, 2'-methyl-4-chlorobiphenyl-3-yl, 3,5-di(2-chlorophenyl)phenyl, 2,3-di(2-chlorophenyl)thiophen-5-yl, 1-(4-aminosulfonylphenyl)-5-(4-chlorophenyl)-pyrazol-3-yl, 2-(2,6-dichlorophenyl)furan-5-yl, 2,3-diphenylthiophen-5-yl, 4,5-diphenylthiazol-2-yl, 3-trifluoromethyl-1-methylthieno[2,3-c]pyrazol-5-yl, 2-(2'-chlorophenyl)pyridin-5-yl, or 2-(2',6'-dichlorophenyl)pyridin-5-yl. Even more particularly preferably, $R^3$ is 2'-chlorobiphen-4-yl.

Within the above preferred $R^3$ groups, $R^4$ is hydrogen; and $R^{4a}$ is —C(O)OR$^d$ where ($R^d$ is hydrogen, $(C_{1-6})$alkyl, $(C_{1-6})$alkoxy$(C_{1-6})$alkyl, $(C_{1-6})$haloalkyl, $(C_{3-7})$cycloalkyl, $(C_{3-7})$cycloalkyl$(C_{1-6})$alkyl, heteroaryl, heteroaryl$(C_{1-6})$alkyl, aryl, or aryl$(C_{1-6})$alkyl). Preferabably, $R^{4a}$ is ethoxycarbonyl, 2-methylpropyloxycarbonyl, 2,2,-dimethylpropyloxycarbonyl, methoxycarbonyl, cyclopentyloxycarbonyl, propyloxycarbonyl, hexyloxycarbonyl, 3-methoxybutyloxycarbonyl, 2-isobutyloxyethyloxycarbonyl, isopropyloxycarbonyl, benzyloxycarbonyl, cyclohexylmethyloxycarbonyl, pyran-4-ylmethyloxycarbonyl, tetrahydrofuran-3-yloxycarbonyl, 2-methoxyethoxycarbonyl, 3,3,3-trifluoropropyloxycarbonyl, cyclobutylmethyloxycarbonyl, 1-propenyloxycarbonyl, cyclobutoxycarbonyl, piperidin-4-ylmethoxycarbonyl, 3-pyrrolidin-1-ylpropyloxycarbonyl, 3-piperidin-1-ylpropyloxycarbonyl, 3-dimethylpropyl-oxycarbonyl, 2-dimethylaminoethyloxycarbonyl, 2-pyridin-4-ylethyloxy-carbonyl, or 2-(4-methylpiperazin-1-ylethyloxycarbonyl.

(2) Within the above preferred, more preferred, and even more preferred groups above, yet another particularly preferred group of compounds is that wherein:

$R^2$ and $R^{4a}$ are hydrogen;

$R^3$ is hydrogen, $(C_{1-6})$ saturated alkyl, phenyl, pyrrolidinyl, piperidinyl, morpholinyl, thiomorpholinyl, piperazinyl, furanyl, thienyl, pyridinyl, or amino; wherein $R^3$ is optionally substituted by one, two or three $R^a$ where each $R^a$ is independently halo or $(C_{1-6})$ saturated alkyl. Preferably, $R^3$ is methyl, trifluoromethyl, 2,2,2-trifluoroethylamino, amino, N,N-dimethylamino, morpholin-4-yl, pyrrolidin-1-yl, piperidin-1-yl, 4-methylpiperazin-1-yl, thien-2-yl, thien-3-yl, furan-2-yl, furan-3-yl, pyridin-2-yl, pyridin-3-yl, pyridin-4-yl, pyrimidin-5-yl, pyrimidin-4-yl, oxazol-4-yl, oxazol-5-yl, thiazol-4-yl, thiazol-5-yl, quinolin-6-yl, indol-5-yl, 2-methylimidazol-4-yl, phenyl, or 4-fluorophenyl; and $R^4$ is hydrogen, $(C_{1-6})$ saturated alkyl, or halogenated alkyl, preferably, hydrogen, 2,2,2-trifluoroethyl or methyl.

(3) Within the above preferred, more preferred, and even more preferred groups above, yet another particularly preferred group of compounds is that wherein:

$R^3$ and $R^4$ in (Ia) and (Ib) together with the atoms to which they are attached form a 5, 6, or 7 membered heterocycloalkyl ring containing at least an —$SO_2$— group or a 5, 6, or 7 membered heterocycloalkyl ring containing at least an —$SO_2$— group and is fused to an aryl or heteroaryl ring wherein wherein each ring is optionally independently substituted by one or two $R^c$ where each $R^c$ is independently halo, alkoxy, haloalkyl, haloalkoxy, hydroxy or alkyl.

Preferably, $R^3$ and $R^4$ in (Ia) and (Ib) together with the atoms to which they are attached form a 5 or 6 membered heterocycloalkyl ring containing at least an —$SO_2$— group or a 5 or 6 membered heterocycloalkyl ring containing at least an —$SO_2$— group and is fused to an aryl or heteroaryl ring optionally independently substituted by one or two $R^c$.

More preferably, $R^3$ and $R^4$ in (Ia) and (Ib) together with the atoms to which they are attached form a 5 or 6 membered heterocycloalkyl ring containing at least an —$SO_2$— group or a 5 or 6 membered heterocycloalkyl ring containing at least an —$SO_2$— group and is fused to a thienyl, or pyrrolyl ring optionally independently substituted by one or two $R^c$.

Even more preferably, $R^3$ and $R^4$ in (Ia) and (Ib) together with the atoms to which they are attached form a 5 or 6 membered heterocycloalkyl ring containing at least an —$SO_2$— group or a 5 or 6 membered heterocycloalkyl ring containing at least an —$SO_2$— group and is fused to a phenyl or pyridinyl ring optionally independently substituted by one or two $R^c$.

Most preferably, $R^3$ and $R^4$ in (Ia) and (Ib) together with the atoms to which they are attached form a ring of formula:

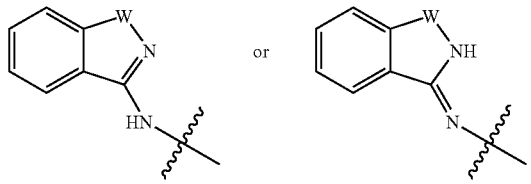

wherein W is —$S(O)_2$— wherein each ring is optionally independently substituted by one or two $R^c$ where each $R^c$ is independently chloro, fluoro, methoxy, trifluoromethyl, trifluoromethoxy, hydroxy, or methyl.

Within the above preferred and more preferred groups in (3), a particularly preferred group of compounds is that where $R^2$ is hydrogen.

(4) Within the above preferred, more preferred, and even more preferred groups above, yet another particularly preferred group of compounds is that wherein:

$R^3$ and $R^4$ in (Ia) and (Ib) together with the atoms to which they are attached form a 5, 6, or 7 membered heterocycloalkyl ring fused to an aryl or heteroaryl ring wherein said heterocyclic ring is substituted on the aromatic and/or non-aromatic portion of the rings with one, two, or three $R^c$ provided that the heterocycloalkyl ring does not contain an —$SO_2$— group;

each $R^c$ is independently $(C_{1-5})$alkyl, $(C_{3-6})$cycloalkyl, aryl, $(C_{1-5})$alkoxy, aryloxy, benzyloxy, alkoxycarbonyl, where each of the aforementioned groups is optionally substituted with halogen, $(C_{1-5})$haloalkyl, $(C_{1-5})$alkyl, $(C_{1-5})$ alkoxy, $(C_{1-5})$haloalkoxy, hydroxy, oxo, carboxy, nitrile, nitro, or —$C(O)NH_2$;

Preferably, $R^3$ and $R^4$ in (Ia) and (Ib) together with the atoms to which they are attached form a 5 or 6 membered heterocycloalkyl ring fused to an aryl or heteroaryl ring wherein said heterocyclic ring is substituted on the aromatic and/or non-aromatic portion of the rings with one, two, or three $R^c$ provided that the heterocycloalkyl ring does not contain an —$SO_2$— group.

More preferably, $R^3$ and $R^4$ in (Ia) and (Ib) together with the atoms to which they are attached form a 5 or 6 membered heterocycloalkyl ring fused to a phenyl or pyridinyl ring wherein said heterocyclic rings is substituted on the aromatic and/or phenyl or pyridinyl portion of the rings with one, two, or three $R^c$ provided that the heterocycloalkyl ring does not contain an —$SO_2$— group;

each $R^c$ is independently $(C_{1-5})$alkyl, $(C_{3-6})$cycloalkyl, phenyl, $(C_{1-5})$alkoxy, aryloxy, benzyloxy, haloalkyl, haloalkoxy, each of the aforementioned groups is optionally substituted with halogen, hydroxy, $(C_{1-3})$alkyl, $(C_{1-3})$alkoxy, $(C_{1-3})$haloalkyl, $(C_{1-3})$haloalkoxy, oxo, carboxy, nitrile, nitro, or —$C(O)NH_2$.

Most preferably, $R^3$ and $R^4$ in (Ia) and (Ib) together with the atoms to which they are attached form a ring of formula:

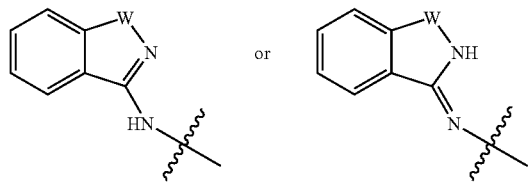

wherein W is —O—C(O)—, —CO—, or —NR—C(O)— (where R is hydrogen, $(C_{1-6})$alkyl, $(C_{1-6})$alkoxycarbonyl $(C_{1-6})$alkyl, $(C_{1-6})$alkylsulfonyl$(C_{1-6})$alkyl, $(C_{1-6})$alkylamino$(C_{1-6})$alkyl, di-$(C_{1-6})$alkylamino$(C_{1-6})$alkyl, heterocycloalkyl, heterocycloalkyl$(C_{1-6})$alkyl, heteroaryl$(C_{1-6})$ alkyl), wherein each ring is independently substituted by one or two $R^c$ each $R^c$ is independently chloro, fluoro, methoxy, trifluoromethyl, trifluoromethoxy, hydroxy, methyl, or phenyl where the phenyl ring is optionally substituted with one, two or three substituents independently selected from chloro, fluoro, methyl, methoxy, trifluoromethyl, trifluoromethoxy, or hydroxy. Preferably $R^c$ is phenyl where the phenyl ring is optionally substituted with one, two or three substituents independently selected from chloro, fluoro, methyl, methoxy, trifluoromethyl, trifluoromethoxy, or hydroxy.

Within the above preferred and more preferred groups in (4), a particularly preferred group of compounds is that where $R^2$ is hydrogen.

(5). Within the above preferred, more preferred and even more preferred groups, yet another particularly preferred group of compounds is that wherein:

$R^3$ and $R^4$ together with the atoms to which they are attached form a 5, 6, or 7 membered heterocycloalkyl ring containing at least an —$SO_2$— group; or a 5, 6, or 7 membered heterocycloalkyl ring containing at least an —SO₂— group and is fused to an aryl or heteroaryl ring; wherein said heterocyclic rings are substituted on the aromatic and/or non-aromatic portion of the rings with one, two, or three $R^c$;

each $R^c$ is independently $(C_{1-6})$alkyl, $(C_{1-6})$alkyl interrupted by one or two N, O, S, S(O), or S(O)₂ and optionally substituted by 1–2 oxo, amino, or halogen, halo, $(C_{1-5})$alkoxy, aryl, pyridinyl, $(C_{1-5})$alkoxy, alkoxycarbonyl, where said aryl and pyridinyl is optionally substituted with one or two substituents independently selected from halogen, $(C_{1-5})$haloalkyl, $(C_{1-5})$alkyl, $(C_{1-5})$alkoxy, $(C_{1-5})$haloalkoxy, or carboxy.

More preferably, $R^3$ and $R^4$ together with the atoms to which they are attached form a 5 or 6 membered heterocycloalkyl ring containing at least an —SO₂— group; or a 5 or 6 membered heterocycloalkyl ring containing at least an —SO₂— group and is fused to a phenyl or pyridinyl ring; wherein said heterocyclic rings is substituted on the aromatic and/or phenyl or pyridinyl portion of the rings with one, two, or three $R^c$;

each $R^c$ is independently $(C_{1-6})$alkyl, $(C_{1-6})$alkyl interrupted by one or two N, O, S, S(O), or S(O)₂ and optionally substituted by 1–2 oxo, amino, halogen, pyrrolidinyl, piperidinyl, piperazin-1-yl, morpholinyl, or thiomorpholinyl, halo, $(C_{1-5})$alkoxy, aryl, pyridinyl, $(C_{1-5})$alkoxy, alkoxycarbonyl, where said aryl and pyridinyl is optionally substituted with one or two substituents independently selected from halogen, $(C_{1-5})$haloalkyl, $(C_{1-5})$alkyl, $(C_{1-5})$alkoxy, $(C_{1-5})$haloalkoxy, or carboxy.

Most preferably, $R^3$ and $R^4$ together with the atoms to which they are attached form a heterocycloalkyl ring fused to a phenyl or pyridinyl ring as shown below:

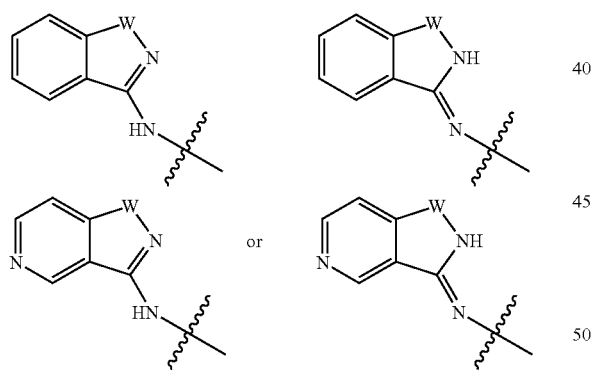

wherein W is —S(O)₂—; wherein the fused phenyl ring is substituted with one, two or three $R^c$;

where one $R^c$ is independently phenyl or pyridinyl and the other two $R^c$ are independently selected from hydrogen, chloro, fluoro, methoxy, trifluoromethyl, trifluoromethoxy, or methyl provided that at least one of them is not hydrogen and where said phenyl and pyridinyl is optionally substituted with one or two substituents independently selected from halogen, $(C_{1-5})$haloalkyl, $(C_{1-5})$alkyl, $(C_{1-5})$alkoxy, $(C_{1-5})$haloalkoxy, or carboxy.

Most preferably, $R^3$ and $R^4$ together with the atoms to which they are attached form a heterocycloalkyl ring fused to a phenyl or pyridinyl ring as shown below:

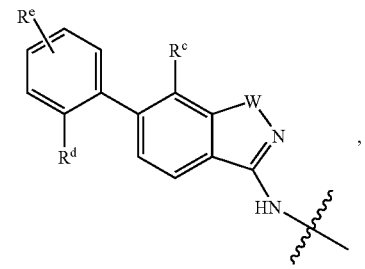

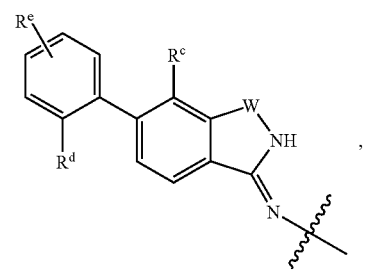

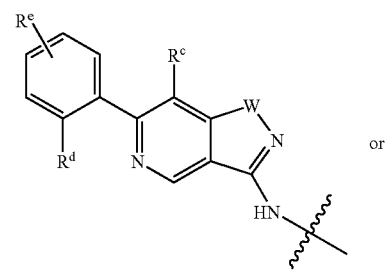

or

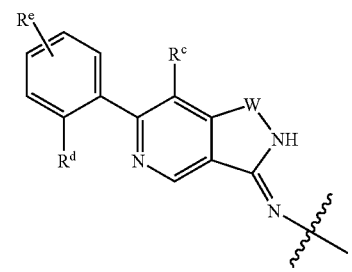

wherein W is —S(O)₂—; and
each $R^c$ and $R^d$ are independently hydrogen, chloro, fluoro, methoxy, trifluoromethyl, trifluoromethoxy, hydroxy, or methyl provided that both $R^c$ and $R^d$ are not hydrogen simultaneously; and $R^e$ is hydrogen or carboxy.

Within the above preferred and more preferred groups in (5), a particularly preferred group of compounds is that where $R^2$ is hydrogen.

(6). Within the above preferred, more preferred and even more preferred groups, yet another particularly preferred group of compounds is that wherein:

$R^3$ and $R^4$ together with the atoms to which they are attached form a 5, 6, or 7 membered heterocycloalkyl ring fused to an aryl or heteroaryl ring provided that it does not contain an —SO₂— group; wherein said heterocyclic rings are substituted on the aromatic and/or non-aromatic portion of the rings with one, two, or three $R^c$;

each $R^c$ is independently $(C_{1-6})$alkyl, $(C_{1-6})$alkyl interrupted by one or two N, O, S, S(O), or S(O)₂ and optionally substituted by 1–2 oxo, amino, or halogen, halo, (C$_{1-5}$)alkoxy, aryl, pyridinyl, (C$_{1-5}$)alkoxy, alkoxycarbonyl, where said aryl and pyridinyl is optionally substituted with one or two substituents independently selected from halogen, (C$_{1-5}$)haloalkyl, (C$_{1-5}$)alkyl, (C$_{1-5}$)alkoxy, (C$_{1-5}$)haloalkoxy, or carboxy.

More preferably, R$^3$ and R$^4$ together with the atoms to which they are attached form a 5 or 6 membered heterocycloalkyl ring fused to a phenyl or pyridinyl ring provided that it does not contain an —SO$_2$— group; wherein said heterocyclic rings is substituted on the aromatic and/or phenyl or pyridinyl portion of the rings with one, two, or three R$^c$;

each R$^c$ is independently (C$_{1-6}$)alkyl, (C$_{1-6}$)alkyl interrupted by one or two N, O, S, S(O), or S(O)$_2$ and optionally substituted by 1–2 oxo, amino, halogen, pyrrolidinyl, piperidinyl, piperazin-1-yl, morpholinyl, or thiomorpholinyl, halo, (C$_{1-5}$)alkoxy, aryl, pyridinyl, (C$_{1-5}$)alkoxy, alkoxycarbonyl, where said aryl and pyridinyl is optionally substituted with one or two substituents independently selected from halogen, (C$_{1-5}$)haloalkyl, (C$_{1-5}$)alkyl, (C$_{1-5}$)alkoxy, (C$_{1-5}$)haloalkoxy, or carboxy.

Most preferably, R$^3$ and R$^4$ together with the atoms to which they are attached form a heterocycloalkyl ring fused to a phenyl or pyridinyl ring as shown below:

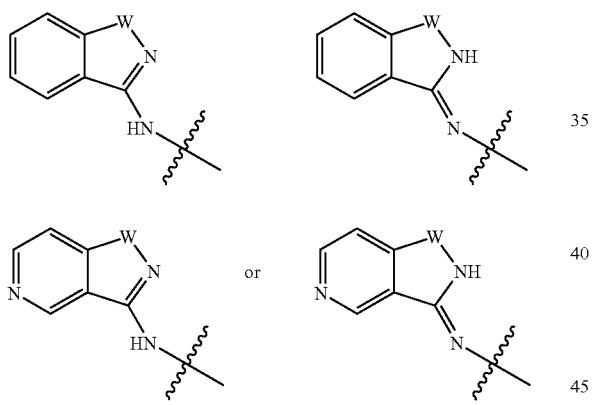

wherein W is —O—C(O)—, —CO—, or —NR—C(O)— (where R is hydrogen, (C$_{1-6}$)alkyl, (C$_{1-6}$)alkoxycarbonyl, (C$_{1-6}$)alkylsulfonyl(C$_{1-6}$)alkyl, (C$_{1-6}$)alkylamino(C$_{1-6}$)alkyl, di-(C$_{1-6}$)alkylamino(C$_{1-6}$)alkyl, morpholinylalkyl, pyrrolidinylalkyl, piperidinylalkyl, or piperazinylalkyl), wherein the fused phenyl ring is substituted with one, two or three R$^c$;

where one R$^c$ is independently phenyl or pyridinyl and the other two R$^c$ are independently selected from hydrogen, chloro, fluoro, methoxy, trifluoromethyl, trifluoromethoxy, or methyl provided that at least one of them is not hydrogen and where said phenyl and pyridinyl is optionally substituted with one or two substituents independently selected from halogen, (C$_{1-5}$)haloalkyl, (C$_{1-5}$)alkyl, (C$_{1-5}$)alkoxy, (C$_{1-5}$)haloalkoxy, or carboxy.

Most preferably, R$^3$ and R$^4$ together with the atoms to which they are attached form a heterocycloalkyl ring fused to a phenyl or pyridinyl ring as shown below:

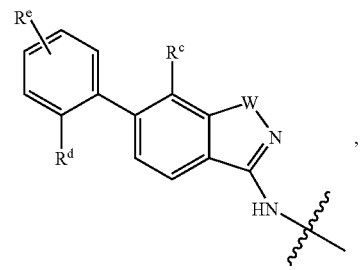

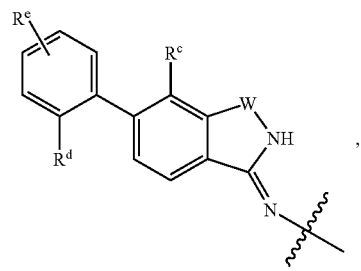

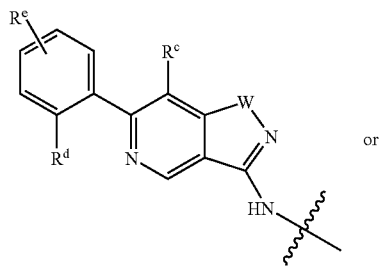

or

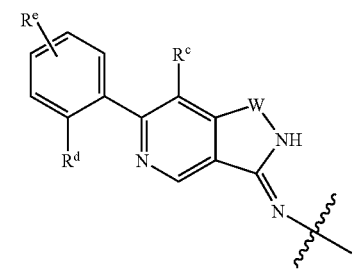

wherein W is —O—C(O)—, —CO—, or —NR—C(O)— (where R is hydrogen, methyl, (C$_{1-6}$)alkyl, (C$_{1-6}$)alkoxycarbonyl(C$_{1-6}$)alkyl, (C$_{1-6}$)alkylsulfonyl(C$_{1-6}$)alkyl, (C$_{1-6}$)alkylamino(C$_{1-6}$)alkyl, di-(C$_{1-6}$)alkylamino(C$_{1-6}$)alkyl, heterocycloalkyl, heterocycloalkyl(C$_{1-6}$)alkyl, or heteroaryl(C$_{1-6}$)alkyl); and each R$^c$ and R$^d$ are independently hydrogen, chloro, fluoro, methoxy, trifluoromethyl, trifluoromethoxy, hydroxy, or methyl provided that both R$^c$ and R$^d$ are not hydrogen simultaneously; and R$^e$ is hydrogen or carboxy.

Within the above preferred and more preferred groups in (6), a particularly preferred group of compounds is that where R$^2$ is hydrogen.

(7) Within the above preferred, more preferred and even more preferred groups, yet another particularly preferred group of compounds is that wherein R$^3$ and R$^4$ together with the atoms to which they are attached form a group selected from:

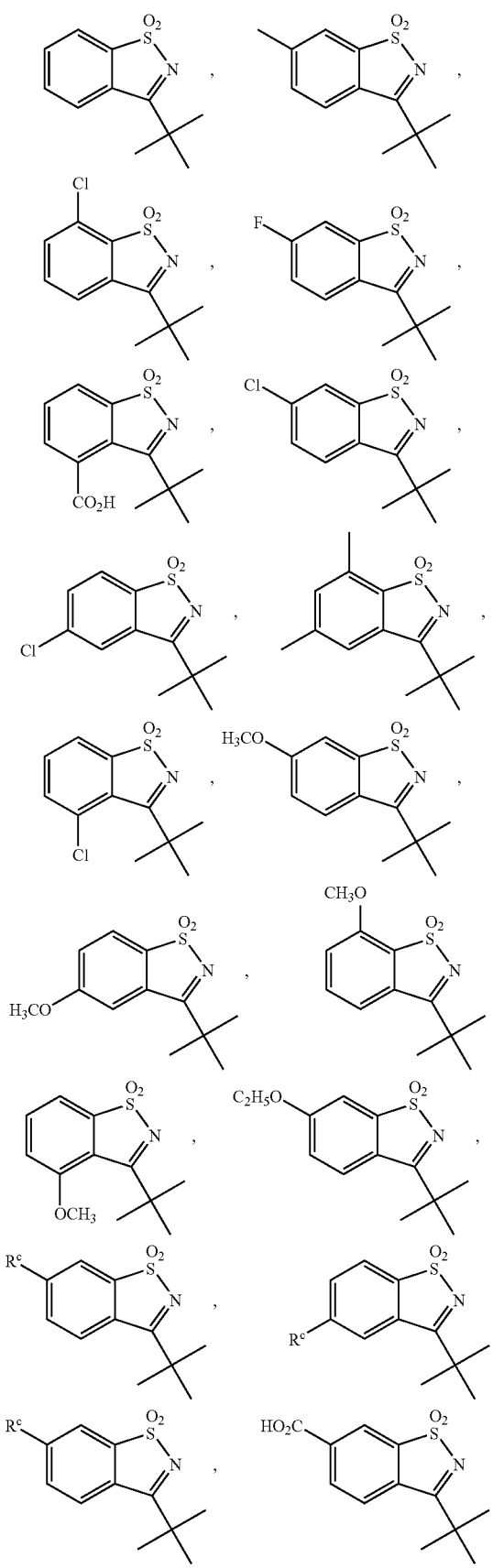
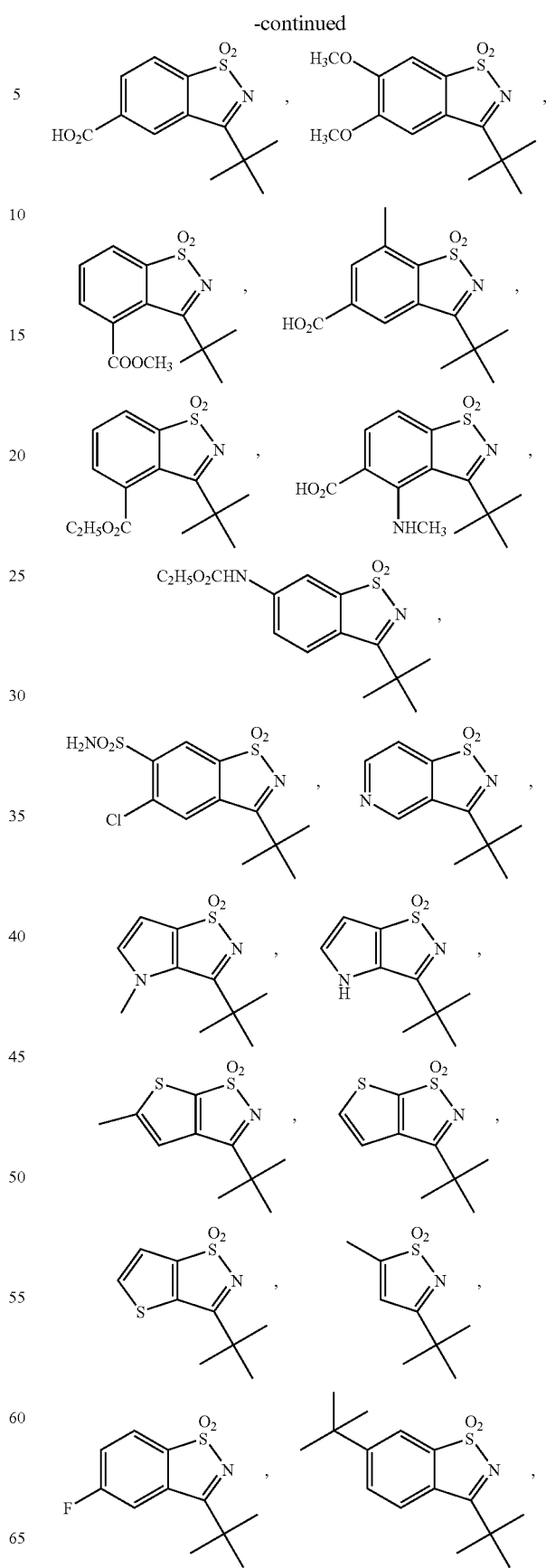

-continued
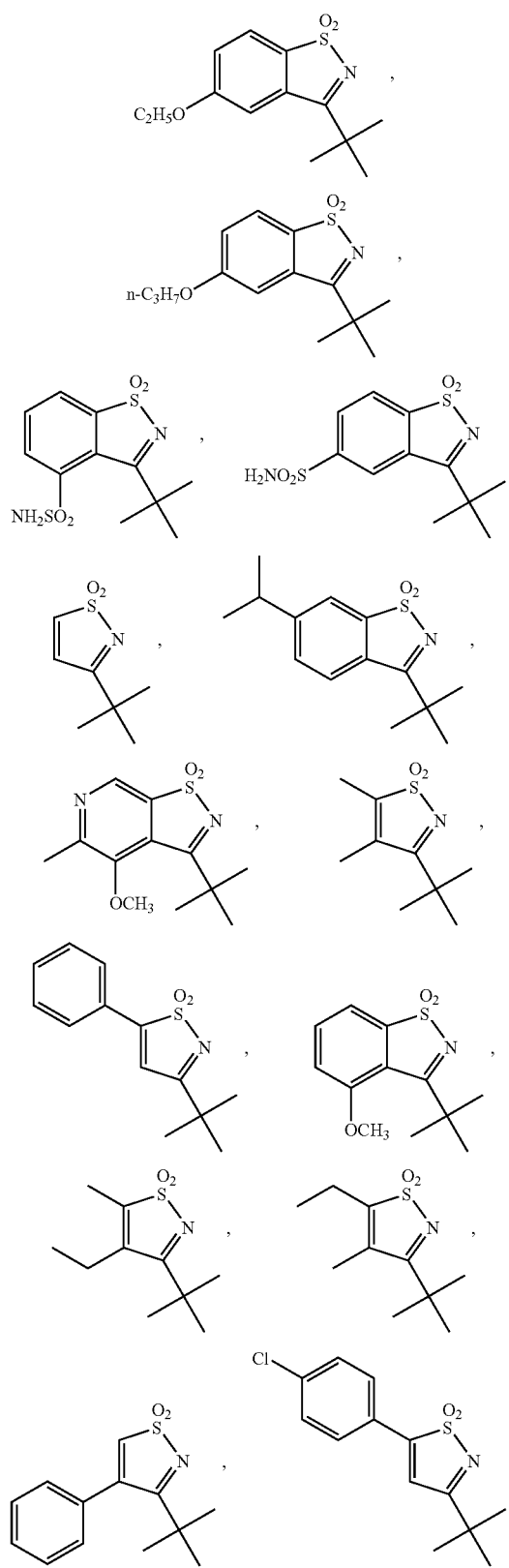
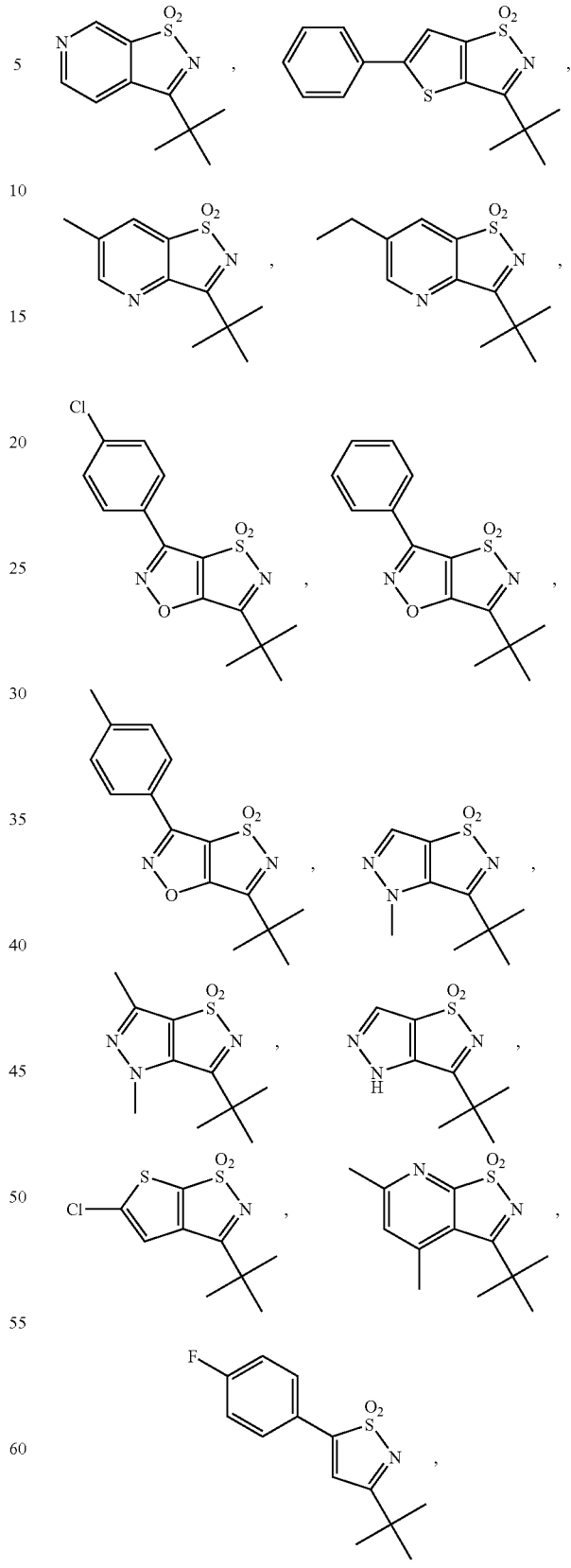

-continued

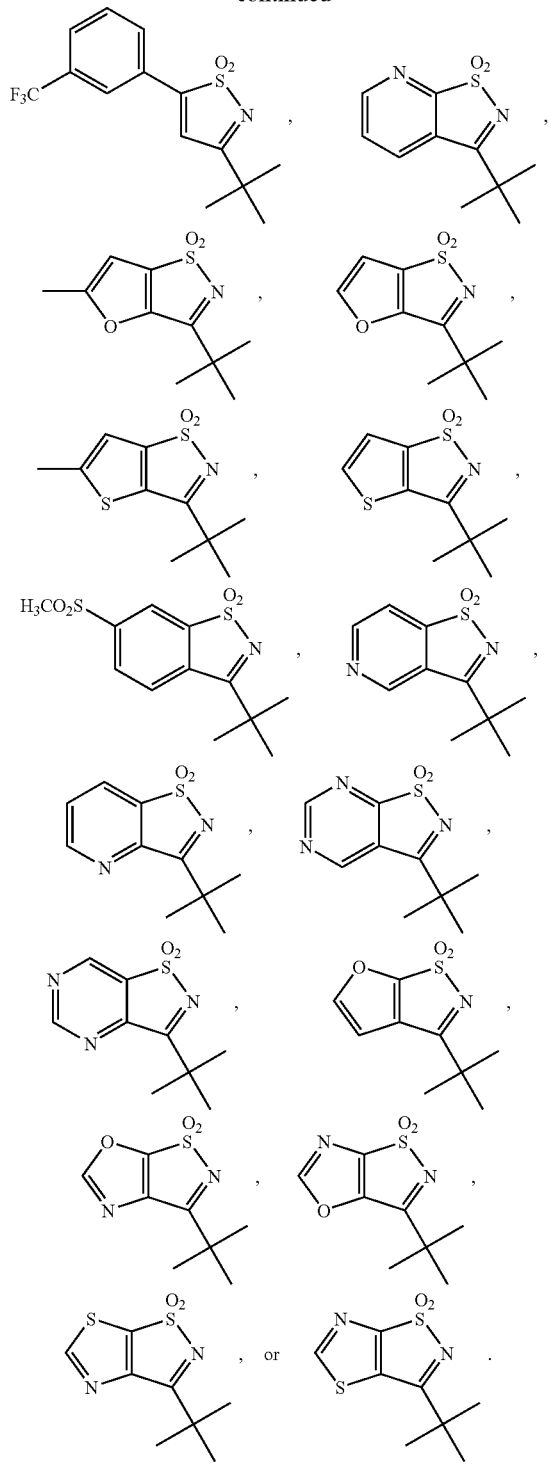

where $R^c$ is amino, methylsulfonylamino, ethylsulfonylamino, methylamino, dimethylamino, acetylamino, methoxy, ethoxy, methylaminocarbonyl, aminocarbonyl, diethylaminocarbonyl, dimethylaminocarbonyl, methylaminocarbonyl, ureido, or ethoxycarbonylamino.

Within the above preferred and more preferred groups in (7), a particularly preferred group of compounds is that where $R^2$ is hydrogen.

(8). Within the above preferred, more preferred and even more preferred groups, yet another particularly preferred group of compounds is that wherein $R^3$ and $R^4$ together with the atoms to which they are attached form a group selected from:

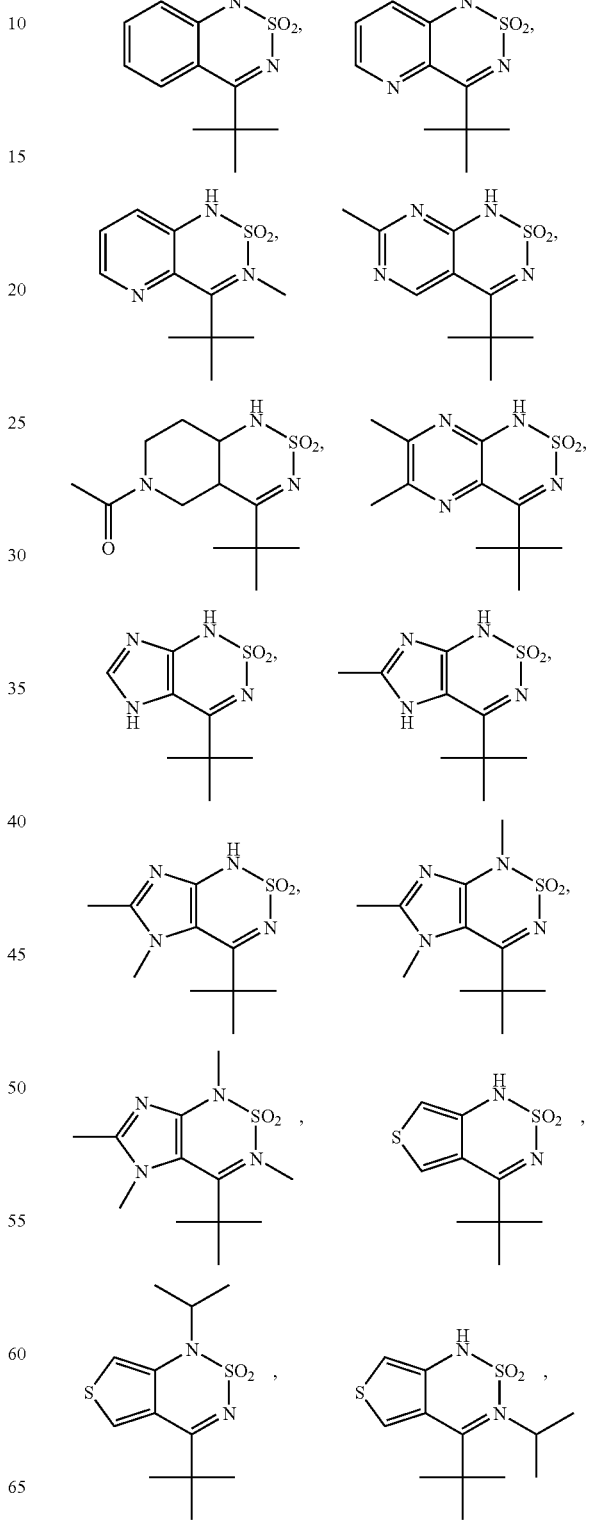

-continued
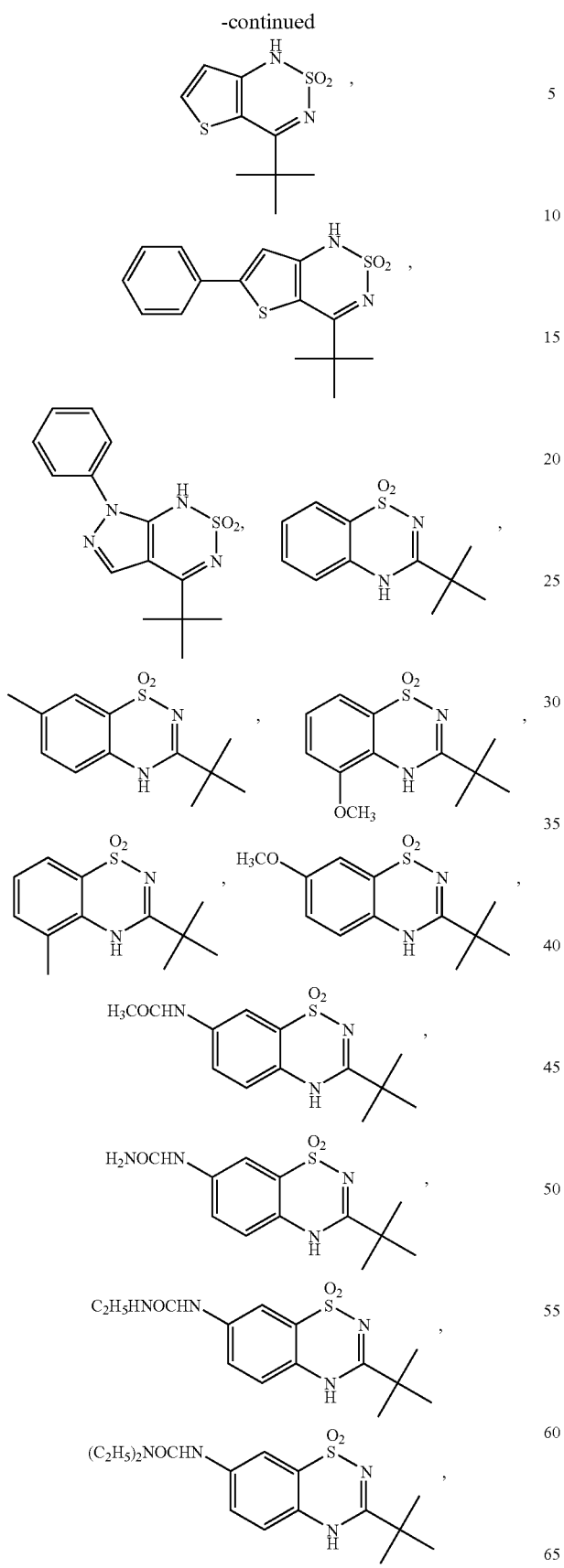
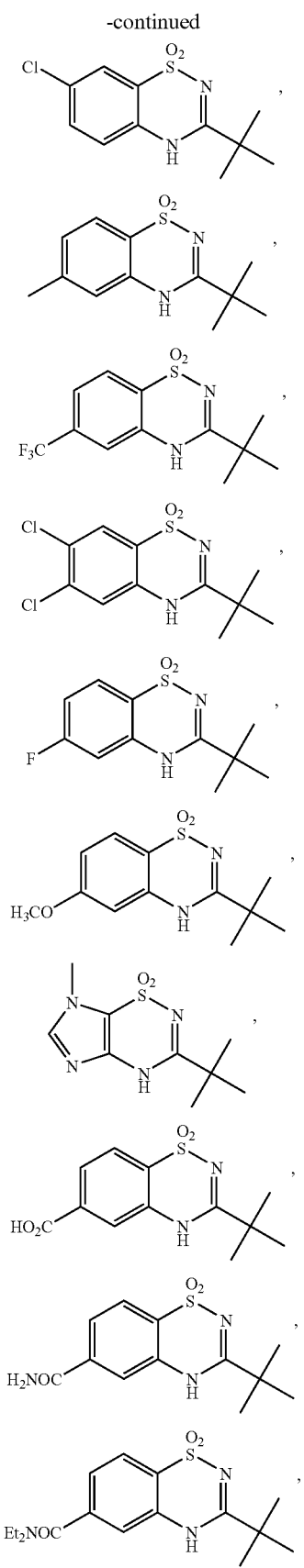

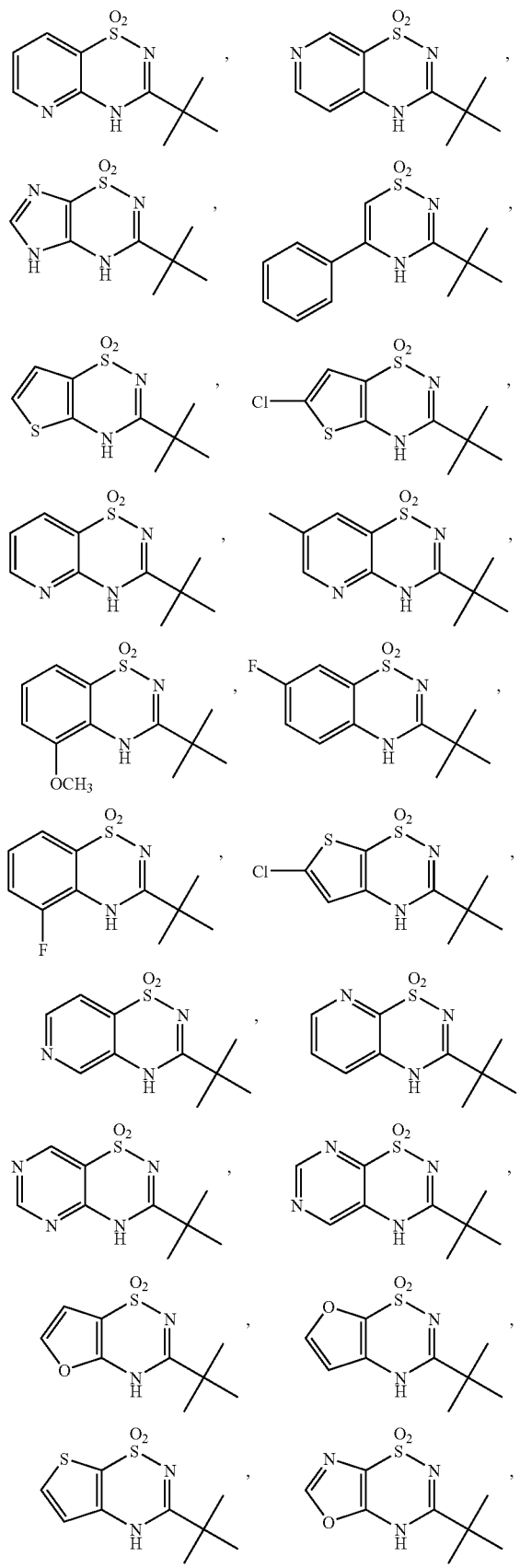

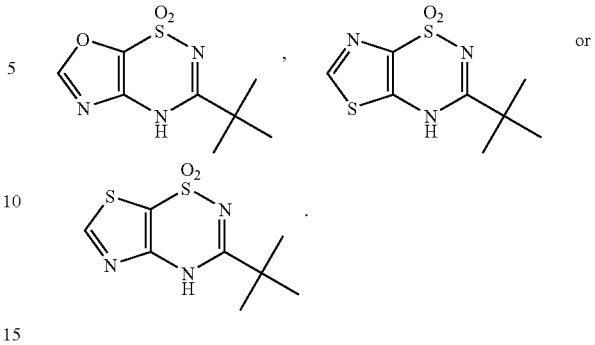

In the above groups, the hydrogen atom attached to the nitrogen can be replaced by $(C_{1-6})$ saturated alkyl, halo substituted $(C_{1-6})$ saturated alkyl, (preferably, methyl, ethyl, propyl, isopropyl, n-, iso-, or tert-butyl, or trifluoromethyl), methylsulfonylmethyl, methoxycarbonylmethyl, 2-methylsulfonylethyl, 2-methoxycarbonylethyl, 2-methylpropyl, 2,2-dimethylpropyl, 1-methylpiperidin-4-yl, 1-methylpiperidin-4-ylmethyl, 2-(1-methylpiperazin-4-yl)ethyl, 2-dimethylaminoethyl, 3-dimethylaminopropyl, 2-pyridin-4-ylethyl, 3-pyrrolidin-1-ylpropyl, 3-piperidin-1-ylpropyl, 2,2,2-trifluoroethyl, or 2-morpholin-4-ylethyl.

Within the above preferred and more preferred groups in (8), a particularly preferred group of compounds is that where $R^2$ is hydrogen.

(II). Another preferred group of compounds in groups (1–3) set forth in the Summary of the Invention is that wherein:

$R^2$, $R^3$ and $R^{4a}$ are hydrogen; and $R^4$ is —SO$_2$R where R is pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl, or quinoxalinyl, —SO$_2$-saturated alkyl, $(C_{1-6})$ saturated alkyl substituted with a heteroaryl ring defined immediately above or pyrrolidinyl, piperidinyl, morpholinyl, thiomorpholinyl, piperazinyl, or indolinyl, —SO$_2$NRR' where R and R' are independently hydrogen or $(C_{1-6})$ saturated alkyl wherein each of the aforementioned group is optionally substituted with halogen, hydroxy, $(C_{1-6})$ saturated alkyl, $(C_{1-6})$ saturated alkoxy, $(C_{1-6})$ saturated haloalkyl, $(C_{1-6})$ saturated haloalkoxy, oxo, carboxy, nitrile, nitro or —CONH$_2$—.

Within preferred group, more preferred groups of compounds are those wherein $R^1$, $R^{1a}$, and E are as defined in preferred group (I) above.

(III). Yet another preferred group of compounds within the groups (1–3) set forth in the Summary of the Invention is made up of compounds of Formula (Ib) wherein $R^4$ is hydrogen and $R^{4a}$ is $(C_{1-6})$alkyl optionally interrupted by one or two N, O, S, S(O), or S(O)$_2$ and optionally substituted by 1–2 oxo, amino, hydroxy, halogen, $C_{1-4}$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

halo, alkoxy, alkylthio, hydroxy, carboxy, aryl, aryloxy, aroyl, furanyl, thienyl, pyrrolyl, imidazolyl, pyridinyl, pyrimidinyl, $(C_{1-6})$alkanoyl, —C(O)OR$^d$ where (R$^d$ is hydrogen, $(C_{1-6})$alkyl, $(C_{1-6})$alkoxycalkyl, $(C_{1-6})$haloalkyl, $(C_{3-7})$cycloalkyl, $(C_{3-7})$cycloalkyl$(C_{1-6})$alkyl, heteroaryl, heteroaryl$(C_{1-6})$alkyl, aryl, aryl$(C_{1-6})$alkyl, or $(C_{1-6})$alkylsulfonyl), aryloxycarbonyl, benzyloxycarbonyl, $(C_{1-6})$alkanoylamino, aroylamino, $C_{1-5}$ alkylthio, arylthio, $(C_{1-6})$alkylsulfonylamino, arylsulfonylamino, $(C_{1-6})$alkylamino-sulfonyl, arylaminosulfonyl, $(C_{3-6})$cycloalkyl and benzyloxy wherein each of the aforementioned group is optionally substituted with halogen, hydroxy, $(C_{1-6})$alkyl, $(C_{1-6})$alkoxy, $(C_{1-6})$haloalkyl, $(C_{1-6})$haloalkoxy, oxo, carboxy, nitrile, nitro or $NH_2C(O)$—.

Preferably, $R^{4a}$ is hydrogen, $(C_{1-5})$alkyl, $(C_{3-6})$cycloalkyl, aryl, $(C_{1-5})$alkoxy, aryloxy, benzyloxy, or —$C(O)OR^d$ where ($R^d$ is hydrogen, $(C_{1-6})$alkyl, $(C_{1-6})$alkoxy$(C_{1-6})$alkyl, $(C_{1-6})$haloalkyl, $(C_{3-7})$cycloalkyl, $(C_{3-7})$Cycloalkyl$(C_{1-6})$alkyl, heteroaryl, heteroaryl$(C_{1-6})$alkyl, aryl, or aryl$(C_{1-6})$alkyl).

More preferably, $R^{4a}$ is hydrogen or —$C(O)OR^d$ where ($R^d$ is hydrogen, $(C_{1-6})$alkyl, $(C_{1-6})$alkoxy$(C_{1-6})$alkyl, $(C_{1-6})$haloalkyl, $(C_{3-7})$cycloalkyl, $(C_{3-7})$cycloalkyl$(C_{1-6})$alkyl, heteroaryl, heteroaryl$(C_{1-6})$alkyl, aryl, or aryl$(C_{1-6})$alkyl). Preferably, $R^{4a}$ is ethoxycarbonyl, 2-methylpropyloxycarbonyl, 2,2,-dimethylpropyloxycarbonyl, methoxycarbonyl, cyclopentyloxycarbonyl, propyloxycarbonyl, hexyloxycarbonyl, 3-methoxybutyloxycarbonyl, 2-isobutyloxyethyloxycarbonyl, isopropyloxycarbonyl, benzyloxycarbonyl, cyclohexylmethyloxycarbonyl, pyran-4-ylmethyloxycarbonyl, tetrahydrofuran-3-yloxycarbonyl, 2-methoxyethoxycarbonyl, 3,3,3-trifluoropropyloxy-carbonyl, cyclobutylmethyloxycarbonyl, 1-propenyloxycarbonyl, cyclobutoxycarbonyl, piperidin-4-ylmethoxycarbonyl, 3-pyrrolidin-1-ylpropyloxycarbonyl, 3-piperidin-1-ylpropyloxycarbonyl, 3-dimethylpropyloxycarbonyl, 2-dimethylaminoethyloxycarbonyl, 2-pyridin-4-ylethyloxycarbonyl, or 2-(4-methylpiperazin-1-yl)ethyloxycarbonyl. As stated earlier these compounds can tautomerize to give a compound of formula (Ib') where $R^2$ is hydrogen. Such tautomers are within the scope of this group.

Within this group (III), more preferred groups of compounds are those wherein E, $R^1$, $R^{1a}$, and $R^3$ are as defined for preferred group (I) above.

(IV). Another preferred group is made up of compounds of Formula (Ia) wherein $R^{1a}$, $R^2$ is hydrogen and $R^4$ is $(C_{1-6})$alkyl that is partially halogenated, —COOR, —CONRR, —CONHR, —SO$_2$R, —SO$_2$NH$_2$, —SO$_2$NHR, —SO$_2$NR$^2$ (where each R is independently alkyl, morpholinyl, or pyridinyl) or —CONH$_2$, preferably 2,2,2-trifluoroethyl. A person skilled in the art will recognize that a compound in this group can tautomerize to give a compound of Formula (Ib) where $R^{4a}$ is hydrogen. The amount of each tautomer present will depend on various conditions such as steric hinderance, pH, temperature, and the like. Accordingly, this group encompasses individual tautomeric forms of compounds of Formula (Ia) as well as mixtures thereof.

Within these preferred and more preferred groups of compounds, a more preferred group of compounds is that wherein E, $R^1$ and $R^3$ is a group defined in preferred group (I) above.

(V). Another preferred group is made up of compounds of Formula (Ia)/(Ib) is that wherein $R^{1a}$, $R^2$ and $R^{4a}$ are hydrogen;

E is —CHR$^6$C(O)R$^{10}$ where $R^6$ is ethyl, propyl, butyl, more preferably ethyl, and $R^{10}$ is hetero$(C_{4-10})$aryl optionally substituted with $(C_{3-10})$aryl, $(C_{6-10})$aryl, hetero$(C_{5-10})$aryl, —$(C_{1-6})$alkyl, halo, halo-substituted $(C_{1-4})$alkyl, NR$^{28}$R$^{28a}$, —OR$^{29}$, or —COOR$^{28}$, —COR$^{29}$ where R$^{28}$ and R$^{28a}$ are independently hydrogen or —$(C_{1-6})$alkyl, R$^{29}$ is hydrogen, —$(C_{1-6})$alkyl, or halo-substituted —$(C_{1-6})$alkyl. More preferably, $R^{10}$ is benzoxazol-2-yl, oxazolo[4,5-b] pyridin-2-yl, 2-pyridin-3-yl-[1,3,4]-oxadiazol-5-yl, 2-pyridin-4-yl-[1,3,4]-oxadiazol-5-yl, 2-ethyl-[1,3,4]-oxadiazol-5-yl, 2-isopropyl-[1,3,4]-oxadiazol-5-yl, 2-tert-butyl-[1,3,4]-oxadiazol-5-yl, 2-phenyl-[1,3,4]-oxadiazol-5-yl, 2-methoxymethyl-[1,3,4]-oxadiazol-5-yl, 2-furan-2-yl-[1,3,4]-oxadiazol-5-yl, 2-thien-2-yl-[1,3,4]-oxadiazol-5-yl, 2-(4-methoxyphenyl)-[1,3,4]-oxadiazol-5-yl, 2-(2-methoxyphenyl)-[1,3,4]-oxadiazol-5-yl, 2-(3-methoxyphenyl)-[1,3,4]-oxadiazol-5-yl, 2-(2-trifluoromethoxyphenyl)-[1,3,4]-oxadiazol-5-yl, 2-(3-trifluoromethoxyphenyl)-[1,3,4]-oxadiazol-5-yl, 2-(4-trifluoromethoxyphenyl)-[1,3,4]-oxadiazol-5-yl, 2-(4-dimethylaminophenyl)-[1,3,4]-oxadiazol-5-yl, pyradizin-3-yl, pyrimidin-2-yl, 3-phenyl-[1,2,4]-oxadiazol-5-yl, 3-ethyl-[1,2,4]-oxadiazol-5-yl, 3-cyclopropyl-[1,2,4]-oxadiazol-5-yl, 3-thien-3-yl-[1,2,4]-oxadiazol-5-yl, 3-pyridin-4-yl-[1,2,4]-oxadiazol-5-yl, 3-pyridin-2-yl-[1,2,4]-oxadiazol-5-yl, 5-ethyl-[1,2,4]-oxadiazol-3-yl, 5-phenyl-[1,2,4]-oxadiazol-3-yl, 5-thien-3-yl-[1,2,4]-oxadiazol-3-yl, 5-trifluoromethyl-[1,2,4]-oxadiazol-3-yl, 5-pyridin-4-yl-[1,2,4]-oxadiazol-3-yl, or 5-phenyloxazol-2-yl; most preferably $R^{10}$ is benzoxazol-2-yl;

$R^1$ is 2,2-dichloroethyl, 2,2,2-trichloroethyl, 1,4-dimethylcyclopentylmethyl, morpholin-4-ylmethyl, isopropylmethanesulfonylmethyl, cyclopentylmethyl, 2,2-difluoro-3-phenylpropyl, pyridin-4-ylmethyl, 2-chlorobenzyl, 4-fluorobenzyl, or 2,2-dichloro-3-phenylpropyl, 2-cyclohexylethyl, cyclohexylmethyl, cyclopentylmethyl, 2-cyclopentylethyl, tert-butylmethyl, 1-methylcyclopropylmethyl, 1-methylcyclohexyl-methyl, 1-methylcyclopentylmethyl, 1,3-dimethylcyclopentylmethyl, morpholin-4-ylmethyl, 2,2-dimethyl-3-phenylpropyl, 1-benzylcyclopropylmethyl, 2-(1,1-difluoromethoxy)phenylmethanesulfonylmethyl, 2-methylpropylsulfonylmethyl, phenylmethanesulfonylmethyl, pyridin-2-ylmethanesulfonyl-methyl, pyridin-4-yl-methanesulfonylmethyl, cyclopropylmethanesulfonylmethyl, pyridin-3-ylmethane-sulfonylmethyl, 2,6-difluorophenylmethanesulfonylmethyl, 2,2-difluoro-3-phenylpropyl, 2,2-dichloropropyl, 2,2-dichloro-3-phenylpropyl, 2-pyridin-2-ylsulfonylethyl, 2-phenylsulfonylethyl, 5-bromothien-2-ylmethyl, pyridin-4-ylmethyl, 2-chlorobenzyl, or 4-fluorobenzyl;

$R^3$ is hydrogen, (C, 6) saturated alkyl, phenyl, pyrrolidinyl, piperidinyl, morpholinyl, thiomorpholinyl, piperazinyl, furanyl, thienyl, pyridinyl, or amino; wherein $R^3$ is optionally substituted by one, two or three $R^a$ where each $R^a$ is independently halo or $(C_{1-6})$ saturated alkyl. Preferably, $R^3$ is methyl, trifluoromethyl, 2,2,2-trifluoroethylamino, amino, N,N-dimethylamino, morpholin-4-yl, pyrrolidin-1-yl, piperidin-1-yl, 4-methylpiperazin-1-yl, thien-2-yl, thien-3-yl, furan-2-yl, furan-3-yl, pyridin-2-yl, pyridin-3-yl, pyridin-4-yl, pyrimidin-5-yl, pyrimidin-4-yl, oxazol-4-yl, oxazol-5-yl, thiazol-4-yl, thiazol-5-yl, quinolin-6-yl, indol-5-yl, 2-methylimidazol-4-yl, phenyl, or 4-fluorophenyl; and $R^4$ is hydrogen, $(C_{1-6})$ saturated alkyl, halo-substituted (C, 6) saturated alkyl, or $(C_{1-6})$ saturated alkylsulfonyl, preferably, hydrogen, 2,2,2-trifluoroethyl, methyl or methylsulfonyl, most preferably trifluoroethyl.

(VI). Another preferred group is made up of compounds of Formula (Ia)/(Ib) is that wherein $R^{1a}$, $R^2$ and $R^{4a}$ are hydrogen;

E is —CHR$^6$C(O)R$^{10}$ where $R^6$ is ethyl, propyl, butyl, more preferably ethyl, and $R^{10}$ is hetero$(C_{4-10})$aryl optionally substituted with $(C_{3-10})$aryl, $(C_{6-10})$aryl, hetero$(C_{5-10})$aryl, —$(C_{1-6})$alkyl, halo, halo-substituted $(C_{1-4})$alkyl, NR$^{28}$R$^{28a}$, —OR$^{29}$, or —COR$^{28}$, —COR$^{29}$ where R$^{28}$ and R$^{28a}$ are independently hydrogen or —$(C_{1-6})$alkyl, R$^{29}$ is hydrogen, —$(C_{1-6})$alkyl, or halo-substituted —$(C_{1-6})$alkyl.

More preferably, $R^{10}$ is benzoxazol-2-yl, oxazolo[4,5-b]pyridin-2-yl, 2-pyridin-3-yl-[1,3,4]-oxadiazol-5-yl, 2-pyridin-4-yl-[1,3,4]-oxadiazol-5-yl, 2-ethyl-[1,3,4]-oxadiazol-5-yl, 2-isopropyl-[1,3,4]-oxadiazol-5-yl, 2-tert-butyl-[1,3,4]-oxadiazol-5-yl, 2-phenyl-[1,3,4]-oxadiazol-5-yl, 2-methoxymethyl-[1,3,4]-oxadiazol-5-yl, 2-furan-2-yl-[1,3,4]-oxadiazol-5-yl, 2-thien-2-yl-[1,3,4]-oxadiazol-5-yl, 2-(4-methoxyphenyl)-[1,3,4]-oxadiazol-5-yl, 2-(2-methoxyphenyl)-[1,3,4]-oxadiazol-5-yl, 2-(3-methoxyphenyl)-[1,3,4]-oxadiazol-5-yl, 2-(2-trifluoromethoxyphenyl)-[1,3,4]-oxadiazol-5-yl, 2-(3-trifluoromethoxyphenyl)-[1,3,4]-oxadiazol-5-yl, 2-(4-trifluoromethoxyphenyl)-[1,3,4]-oxadiazol-5-yl, 2-(4-dimethylaminophenyl)-[1,3,4]-oxadiazol-5-yl, pyradizin-3-yl, pyrimidin-2-yl, 3-phenyl-[1,2,4]-oxadiazol-5-yl, 3-ethyl-[1,2,4]-oxadiazol-5-yl, 3-cyclopropyl-[1,2,4]-oxadiazol-5-yl, 3-thien-3-yl-[1,2,4]-oxadiazol-5-yl, 3-pyridin-4-yl-[1,2,4]-oxadiazol-5-yl, 3-pyridin-2-yl-[1,2,4]-oxadiazol-5-yl, 5-ethyl-[1,2,4]-oxadiazol-3-yl, 5-phenyl-[1,2,4]-oxadiazol-3-yl, 5-thien-3-yl-[1,2,4]-oxadiazol-3-yl, 5-trifluoromethyl-[1,2,4]-oxadiazol-3-yl, 5-pyridin-4-yl-[1,2,4]-oxadiazol-3-yl, or 5-phenyloxazol-2-yl; most preferably $R^{10}$ is benzoxazol-2-yl;

$R^1$ is $R^1$ is 2,2-dichloroethyl, 2,2,2-trichloroethyl, 1,4-dimethylcyclopentylmethyl, morpholin-4-ylmethyl, isopropylmethanesulfonylmethyl, cyclopentylmethyl, 2,2-difluoro-3-phenylpropyl, pyridin-4-ylmethyl, 2-chlorobenzyl, 4-fluorobenzyl, or 2,2-dichloro-3-phenylpropyl, 2-cyclohexylethyl, cyclohexylmethyl, cyclopentylmethyl, 2-cyclopentylethyl, tert-butylmethyl, 1-methylcyclopropylmethyl, 1-methylcyclohexyl-methyl, 1-methylcyclopentylmethyl, 1,3-dimethylcyclopentylmethyl, morpholin-4-ylmethyl, 2,2-dimethyl-3-phenylpropyl, 1-benzylcyclopropylmethyl, 2-(1,1-difluoromethoxy)phenylmethanesulfonylmethyl, 2-methylpropylsulfonylmethyl, phenylmethanesulfonylmethyl, pyridin-2-ylmethanesulfonyl-methyl, pyridin-4-yl-methanesulfonylmethyl, cyclopropylmethanesulfonylmethyl, pyridin-3-ylmethanesulfonylmethyl, 2,6-difluorophenylmethanesulfonylmethyl, 2,2-difluoro-3-phenylpropyl, 2,2-dichloropropyl, 2,2-dichloro-3-phenylpropyl, 2-pyridin-2-ylsulfonylethyl, 2-phenylsulfonylethyl, 5-bromothien-2-ylmethyl, pyridin-4-ylmethyl, 2-chlorobenzyl, or 4-fluorobenzyl; and $R^3$ and $R^4$ together are cyclic groups shown in subgroups (I)(7) and (I)(8) above.

(VII). Another preferred group is made up of compounds of Formula (Ia)/(Ib) is that wherein $R^{1a}$, $R^2$ and $R^4$ are hydrogen;

$R^3$ is hydrogen, $(C_{1-6})$ saturated alkyl, phenyl, pyrrolidinyl, piperidinyl, morpholinyl, thiomorpholinyl, piperazinyl, furanyl, thienyl, pyridinyl, or amino; wherein $R^3$ is optionally substituted by one, two or three $R^a$ where $R^a$ is halo or $(C_{1-6})$ saturated alkyl. Preferably, $R^3$ is methyl, trifluoromethyl, 2,2,2-trifluoroethylamino, amino, N,N-dimethylamino, morpholin-4-yl, pyrrolidin-1-yl, piperidin-1-yl, 4-methylpiperazin-1-yl, thien-2-yl, thien-3-yl, furan-2-yl, furan-3-yl, pyridin-2-yl, pyridin-3-yl, pyridin-4-yl, pyrimidin-5-yl, pyrimidin-4-yl, oxazol-4-yl, oxazol-5-yl, thiazol-4-yl, thiazol-5-yl, quinolin-6-yl, indol-5-yl, 2-methylimidazol-4-yl, phenyl, or 4-fluorophenyl; and $R^{4a}$ is heteroaryl, $(C_{1-6})$ saturated alkylsulfonyl, or $(C_{1-6})$ halo-substituted saturated alkylsulfonyl.

Within this group, preferred groups are where E and $R^1$ are as defined in preferred group (I) above.

(VIII). Another preferred group of compounds in groups (1–3) set forth in the Summary of the Invention is that wherein:

$R^2$, $R^3$ and $R^4$ are hydrogen; and $R^{4a}$ is aryl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl, or quinoxalinyl optionally substituted with halogen, hydroxy, $(C_{1-6})$ saturated alkyl, $(C_{1-6})$ saturated alkoxy, $(C_{1-6})$ saturated haloalkyl, $(C_{1-6})$ saturated haloalkoxy, oxo, carboxy, nitrile, nitro or —$CONH_2$—.

Within preferred group, more preferred groups of compounds are those wherein $R^1$, $R^{1a}$, and E are as defined in preferred group (I) above.

A person skilled in the art will recognize that compounds of Formula (Ia) where $R^2$ is hydrogen can tautomerize to give a compound of Formula (Ib) where $R^4$ or $R^{4a}$ is hydrogen and compounds of Formula (Ib) where $R^4$ or $R^{4a}$ is hydrogen can tautomerize to give a compound of Formula (Ia) or (Ib') respectivelyl, where $R^2$ is hydrogen. Such tautomers are within the scope of this group. The amount of each tautomer present will depend on various conditions such as steric hinderance, pH, temperature, and the like. Accordingly, this group encompasses individual tautomeric forms of compounds of Formula (Ia) as well as mixtures thereof.

Additionally, in the preferred embodiments above, a number of different preferences have been given above, and following any one of these preferences results in a compound of this invention that is more presently preferred than a compound in which that particular preference is not followed. However, these preferences are generally independent; and following more than one of these preferences may result in a more presently preferred compound than one in which fewer of the preferences are followed.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1–17 (John Wiley and Sons, 1991); Rodd's Chemistry of Carbon Compounds, Volumes 1–5 and Supplementals (Elsevier Science Publishers, 1989); Organic Reactions, Volumes 1–40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data. Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "*Protective Groups in Organic Chemistry*" John Wiley and Sons, 1991. Compound of Formula (Ia) and (Ib) can be prepared by the procedures described in Schemes 1–4 below.

Compounds of Formula (Ia) where E is —C($R^5$)($R^6$)$X^1$ and $R^1$, $R^{1a}$, $R^2$, $R^3$, $R^4$, $R^5$, and $R^6$ are as defined in the Summary of the Invention can be prepared by proceeding as in the following Reaction Scheme 1 below.

Scheme 1

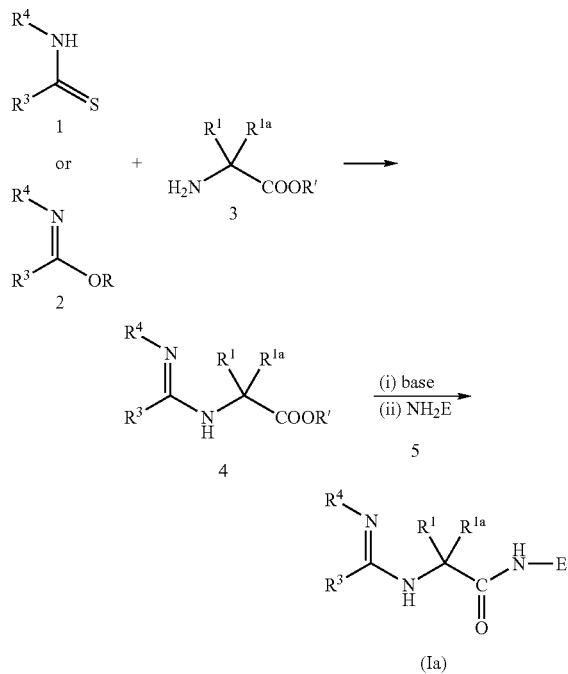

Compounds of Formula (Ia) can be prepared by reacting an amino acid derivative of formula 3 where R' is alkyl, with a thione of formula 1 to give a compound of formula 4. The reaction is carried out in the presence of a suitable coupling agent such as 2-chloro-1-methylpyridinium iodide (Yong, Y. F, et. al., *J. Org. Chem.* 1997, 62, 1540), phosgene or triphosgene (Barton, D. H., et. al., *J. Chem. Soc. Perkin Trans. I*, 1982, 2085), alkyl halides (Brand, E and Brand, F. C., *Org. Synth.*, 1955, 3, 440), or carbodiimide (Poss, M. A., et. al., *Tet. Lett.*, 1992, 40, 5933).

Alternatively, a compound of formula 4 is prepared by reacting a hydroxy compound of formula 2 with an amino acid derivative of formula 3. The reaction is carried out optionally in the presence of a base such as triethylamine. Suitable reaction conditions are known to those skilled in the art and examples of such amine additions can be found in the art e.g., Haake, M., et. al., *Synthesis*, 1991, 9, 753; Dauwe, C., et al, *Synthesis*, 1995, 2, 171, Reid, et. al., *Justus Liebigs Ann. Chem.*, 1966, 97, 696; and Dean N. D., and Papadopoulos, E. P. *J Het. Chem.*, 1982, 19, 1117.

Compounds 1, 2 and 3 are commercially available or they can be prepared by methods well known in the art. For example, N-phenyl-2,2,2-trifluorothioacetamide can be prepared by method described in *Tet. Lett.*, 2001, 42, 46, 8181–8184; N-thiazol-2-ylthioacetamide can be prepared by the procedure described in *Chem. Heterocyclo*, 1972, 848–851; and N-thiazol-2-ylphenylthiobenzamide can be prepared as described in by the procedure described in *Chem. Heterocyclo*, 1988, 337–344. Others can be prepared by methods are described in PCT Application Publication No. WO 02/20485 the disclosure of which is incorporated herein by reference in its entirety. Compounds of formula 2 are either commercially available or they can be prepared by methods known in the art. Some such methods are described in Francesconi, I., et. al., *J. Med. Chem.*, 1999, 42, 2260; Kurzer, F., et. al., *Org. Synth.* 1963, 645; and Futman, A. D., U.S. Pat. No. 3,984,410. For example, ethyl benzenesulfonyl formimidate can be prepared by methods described in Stetter, H. and Theisen, D. H. *Chem Ber.*, 1969, 102, 1641–42 and Ortiz, J. A., *Arzneim.-Forsch./Drug Res*, 1977, 47, 431–434.

Amino acids of formula 3 such as esters of alanine, cysteine, aspartic acid, glutamic acid, phenylalanine, histidine, and lysine are commercially available. Others can be prepared by methods well known in the art. Some such methods are described in PCT Applications Publication Nos. WO 00/55144, WO 01/19816, WO 02/20485, WO 03/029200, U.S. Provisional Application No. 60/422,337, U.S. Pat. Nos. 6,353,017B1, 6,492,662B1, 353,017 B1 and 6,525,036B1, the disclosures of which are incorporated herein by reference in their entirety.

Hydrolysis of the ester group in 4, followed by reaction of the resulting acid with an amine of formula 5 where E is as defined in the Summary of the Invention provides a compound of Formula (Ia). The reaction can be effected with an appropriate coupling agent (e.g., benzotriazol-1-yloxy-trispyrrolidinophosphonium hexafluorophosphate (Py-BOP®), 1-(3-dimethylaminopropyl)-3-ethylcarbodiimide hydrochloride (EDCI), O-(7-azabenzotrizol-1-yl)-1,1,3,3, tetra-methyluronium-hexafluorophosphate (HATU), O-benzotriazol-1-yl-N,N,N',N'-tetramethyl-uronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), or the like) and non-nucleophilic base (e.g., triethylamine, N-methylmorpholine, and the like, or any suitable combination thereof) at ambient temperature and requires 5 to 10 h to complete. Suitable reaction solvents include, but are not limited to, dimethylformamide, methylene chloride, and the like.

Alternatively, the free acid of compound 4 can be converted to an acid halide and then reacted with 5 to give a compound of Formula (Ia). The reacting is carried out in the presence of a base such as triethylamine, pyridine, and the like and in a suitable organic solvent such as tetrahydrofuran, dioxane, and the like. Compounds of formula 5 are either commercially available or they can be prepared by methods well known in the art. Some such methods are disclosed in working examples below. Other methods are disclosed in U.S. patent application Ser. Nos. 60/373,176, 09/525,507, and 10/035,783 the disclosures of which are incorporated herein by reference in their entirety.

A compound of Formula (Ia) can be converted to other compounds of Formula (Ia). For example, a compound of Formula (Ia) where E is —C($R^7$)($R^8$)$R^{10}$ where $R^7$ is hydrogen and $R^8$ is hydroxy can be converted to other compounds of Formula (Ia) where E is —COR$^{10}$ by oxidation of the hydroxy group. The oxidation reaction is carried out with an oxidizing agent (e.g., Dess-Martin Periodinane®, TEMPO/ bleach, or the like) in a suitable solvent (e.g., acetonitrile, dichloromethane, methanol, water, or the like, or any suitable combination thereof) at ambient temperature and requires 16 to 24 h to complete. Detailed descriptions for the synthesis of a compound of Formula (Ia) by the processes in Reaction Scheme 1 are set forth in the Example 1 below.

Alternatively, a Formula (Ia) where E is —C($R^5$)($R^6$)$X^1$ and $R^1$, $R^{1a}$, $R^2$, $R^3$, $R^4$, $R^5$, and $R^6$ are as defined in the Summary of the Invention can be prepared by proceeding as in the following Reaction Scheme 2 below.

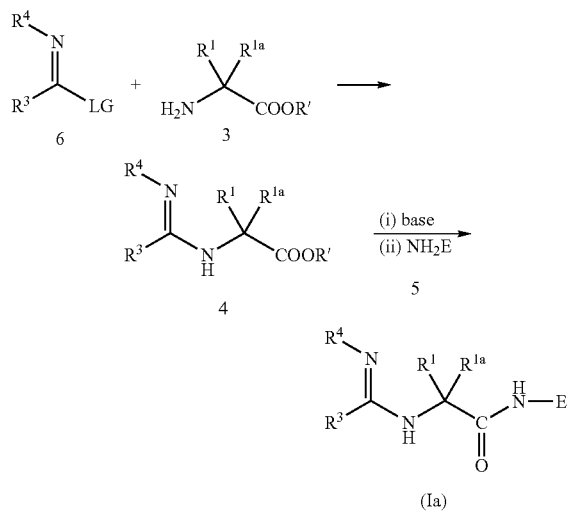

Reaction of a compound of formula 6 where LG is a leaving group such as halo with an amino compound of formula 3 provides a compound of formula 4 which is then converted to a compound of Formula (Ia) as described above. The reaction is carried out by methods well known in the art. Some such methods are described in Dunn. A. D., *Org. Prep. Proceed. Int.*, 1998, 30, 709; Lindstroem, S., et. al., *Heterocycles*, 1994, 38, 529; Katrizky, A. R., et. al., *Synthesis*, 1990, 561; Hontz, A. C., et. al., *Org. Synth.*, 1963, IV, 383; and Stephen, H., *J. Chem., Soc.*, 1957, 490.

Compounds of formula 6 are either commercially available or they can be readily prepared by methods well known in the art. For example, For example, 3-chloro-1,1-dioxobenzo[d]isothiazole is commercially available. 4-Chlorobenzo[e][1,3]oxazin-2-one can be obtained by treating benzo[e][1,3]oxazine-2,4-dione with phosphorus pentachloride in refluxing toluene. Similarly, 3-chloro-2,3-dihydrothieno[3,4-d]isothiazole 1,1-dioxide and 3-chloro-2,3-dihydrothieno[3,2-d]isothiazole can be prepared from 1,1-dioxide 1,1-dioxo-1,2-dihydro-1$\lambda^6$-thieno[3,4-d]isothiazol-3-one and 1,1-dioxo-1,2-dihydro-1$\lambda^6$-thieno[3,2-d]isothiazol-3-one respectively, as described above. 1,1-Dioxide-1,1-dioxo-1,2-dihydro-1$\lambda^6$-thieno[3,4-d]isothiazol-3-one and 1,1-dioxo-1,2-dihydro-1$\lambda^6$-thieno[3,2-d]isothiazol-3-one are described by the procedures described in *J. Org. Chem.*, 1980, 45, 617–620. Other compounds of formula 6 disclosed in preferred embodiment (I) (7) and (8) above, can be prepared from corresponding carbonyl compounds starting materials known in the art by converting them to the corresponding halo derivative as described above. For examples, the following references describe the synthesis of some of the carbonyl starting materials: *Chem. Ber.* 1962, 84, 509; Cohen, E. Klarberg, B, *JACS*, 1962, 84, 1992–2002; BASF patent, FR 2276309, DE 2430353; Edenhofer, A., Meister, W., *Helv. Chim. Acta*, 1977, 60, 521–523; Kloek, J. A.; Leschinsky, K. L., *J. Org. Chem.*, 1978, 43, 3824–3827; Goya, et al., *J. Heterocycl. Chem*, 1984, 21, 861–864; Meyer, R. B., and Skibo, E. B., *J. Med. Chem.*, 1979, 22, 944–948; Ochoa, C; and Stud, M., *J. Heterocycl. Chem.*, 1978, 15, 221–224; Edenhofer, A., and Meister, W., *Helv. Chim. Acta*, 1977, 60, 521–523; Goya, et al, *Synthesis*, 1989, 280–282; Monsanto patent, U.S. Pat. No. 4,139,700; Womhoff, H. and Ertas, M., *Synthesis*, 1985, 190–194; Raffa, *Farmaco Ed. Sci.*, 1957, 12, 41–47; Girare, Y. et al., *J. Chem. Soc. Perkin Trans.* 1, 1979, 1043–1047; Parke, W., *J. Chem. Soc.*, 1950, 1760, 1763; Raffa, *Farmaco Ed. Sci.*, 1960, 15, 716–725; Raffa, *Farmaco Ed. Sci.*, 1966, 21, 16–29; Hayman, D. F., et al, *J. Pharm. Pharmacol.*, 1962, 14, 522–533; Raffa, *Farmaco Ed. Sci.*, 1962, 17, 234–243; Blicke, F. F. and Lee, C. M., *J. Org. Chem.*, 1961, 26, 1861–1867; Kotovskaya, S. K., et al., *J. Pharm. Chem.*, 1979, 13, 4, 389–392; Ofiserov, V. 1, et al., *Chem. Heterocycl. Compd.*, 1976, 12, 924–927; Thompson, M. E., *Synthesis*, 1988, 9, 733–735; Arranz, M. E., et al., *Heterocycles*, 1977, 45, 9, 1767–1774; Neill, C. G, et al., *Tetrahedron*, 1988, 54, 44, 13645–13654; Phillips, D., et al., *Bioorg. Med. Chem.*, 2002, 10, 5, 1229–1248; Ihara Chem. Ind. Patent FR 231,4185; DE 261,6611, Becke, F. and Hagen, H., *Justus Liebigs Ann. Chem.*, 1969, 729, 146–151; Burri, K. F., *Helv. Chim. Acta.*, 1990, 73, 1, 69–80; Kwon, Soon-Kyoung and Park, Myung-Sook, *Arzneim. Forsch.*, 1996, 46, 10, 966–971; Lombardino, J. G., *J. Org. Chem.*, 1971, 36, 1843–1845; Hlasta, D. J., et al., *Tet. Lett.*, 1991, 32, 49, 7179–7182; Haworth, L., *J. Chem. Soc.*, 1924, 125, 1304; Moulton, *J. Am. Chem.*, 1891, 13, 200; Zincke, G., *Justus Liebigs Ann. Chem.*, 1922, 427, 249; Remsen, B., J. Am. Chem., 2, 1880/1881, 411; Schoop, *Chem. Ber.*, 1881, 14, 223; Weber., *Chem. Ber.*, 1892, 25, 1740; Szabo, *Bull. Soc. Chim. Fr.*, 1953, 771–773; Love. K., *J. Org. Chem.*, 1962, 27, 2177–2180; Jocobsen, *Justus Liebigs Ann. Chem.*, 1881, 206, 175; Finzi, C., *Gazz. Chim. Ital.*, 1938, 68, 132–139; Fahlberg, *Chem. Ber.*, 1887, 20, 1603; de Stevens et al., *J. Med. Pharm. Chem.*, 1959, 1, 565–573; Thomae, K., DE 2749640; Hamor, G. H., *J. Am. Pharm. Assoc. Sci. Ed.* 1960, 49, 280–283; Warren, A. and Hamor, G. H., *J. Pharm. Sci.*, 1961, 50, 625–626; Unterhalt, B. and Moghaddam, S., *Pharmazie*, 1994, 49, 2/3, 115–117; Vega. S., et al., Dur. *J. Med. Chem. Chim. Ther.*, 1988, 23, 329–334; Rohm-Hass Co., U.S. Pat. No. 3,562,283; Lewis, S. N., *J. Heterocycl. Chem.*, 1971, 8, 591–595; Gilbert, E. E., *J. Org. Chem*, 1970, 35, 850–852; Shkulev, V. A. et al., *J. Pharm. Chem.*, 1977, 11, 10, 1376–1379; Horii, Patent JP 1683, 1962; Lewis. S. N., *J. Heterocycl. Chem.*, 1971, 8, 591–595; Chekhuta, V. G. et al., *J. Org. Chem.* USSR, 1967, 3, 1763–1766; Schulze, B. and Muehlstaedt, M., *A. Chem., GE*, 1988, 28, 10, 362; Alo, B., et al., *J. Heterocycl. Chem.*, 1992, 29, 1, 61–64; Waldner, A., *Helv. Chim. Acta.*GE, 1989, 72, 1435–1443; Burri, K. F., *Helv. Chim. Acta.*, 1989, 72, 1416–1427; and Zawisza, T. and Malinka, W., *Farmaco Ed. Sci.*, 1986, 41, 9, 676–683.

Alternatively, a compound of Formula (Ia) where E is —C($R^5$)($R^6$)$X^1$ and $R^3$, $R^4$, $R^1$, $R^{1a}$, $R^5$, and $R^6$ are as defined in the Summary of the Invention can be prepared by proceeding as in the following Reaction Scheme 3 below.

Scheme 3

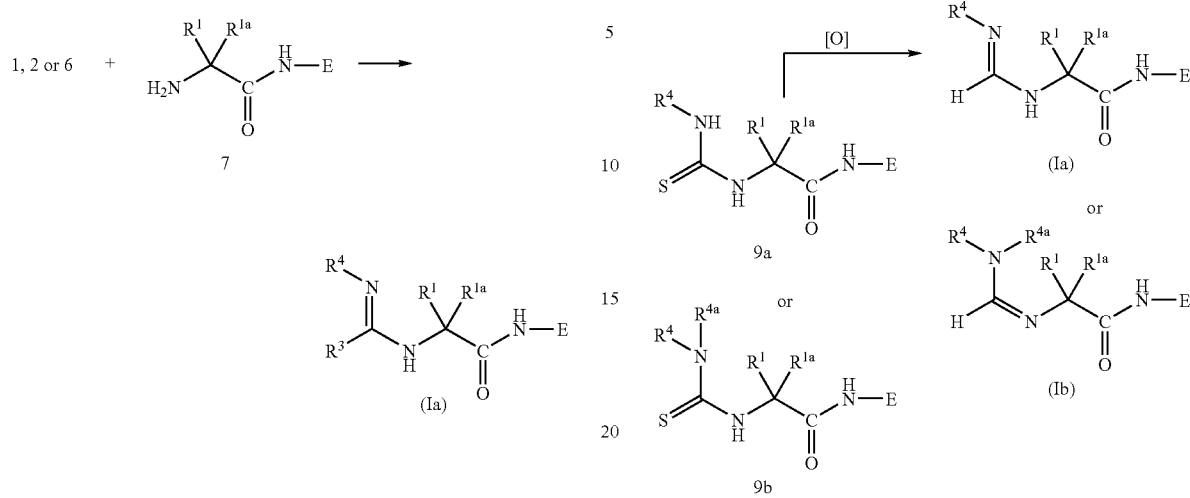

Reaction of a compound of formula 1, 2 or 6 with an amino compound of formula 7 provides a compound of Formula (Ia). The reaction is carried out under the reaction conditions described in Scheme 1 above. Compounds of formula 7 can be prepared by reacting an N-protected amino acid of formula 3 (R'=H) with a compound of formula 5 under the coupling reaction conditions described above, followed by removal of the amino protecting group. Suitable amino protecting groups include, but are not limited to, tert-butoxycarbonyl, benzyloxycarbonyl, and the like. Other methods that can be utilized for preparing compounds of Formula (Ia) and (Ib) are described in PCT Application Publication Nos. WO 02/20485 and WO 03/029200, and U.S. Pat. No. 6,420,364, the disclosures of which are incorporated herein by reference in their entirety.

Alternatively, a compound of Formula (Ia)/(Ib) where E is —C(R$^5$)(R$^6$)X$^1$ and R$^3$ hydrogen or an amino containing group and is bonded to the carbon via the nitrogen atom, R$^4$, R$^1$, R$^{1a}$, R$^5$, and R$^6$ are as defined in the Summary of the Invention can be prepared by proceeding as in the following Reaction Scheme 4 below.

Scheme 4

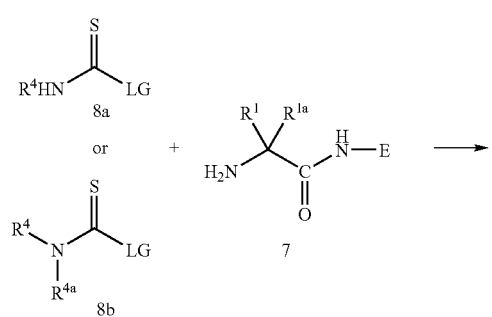

Reaction of a compound of formula 8a or 8b where LG is a suitable leaving group such as imidazol-1-yl with an acid addition salt or free base of a compound of formula 7 provides a compound of formula 9a or 9b respectively. The reaction is carried out in the presence of a base such as diisopropylamine, triethylamine, and the like (if acid addition salt of 7 is used) and in a suitable organic solvent such as methylene chloride, dioxane, and the like. Compounds of formula 8a and 8b can be readily prepared by reacting an amine of formula R$^4$NH$_2$ and R$^4$R$^{4a}$NH respectively, with thio coupling agent such as 1,1'-thiocarbonyldiimidazole, and the like.

Compound 9a or 9b is then converted to a compound of Formula (Ia) or (Ib) by reacting it with an R$^3$ group containing a reactive nitrogen atom. For example, a compound of Formula (Ia) where R$^3$ is morpholin-1-yl, piperidin-1-yl, or piperazin-1-yl can be prepared by heating a compound formula 9a with morpholine, piperidine, or piperazine respectively, in the presence of copper sulfate on silica gel and a suitable base such as triethylamine, and the like, in a microwave reactor. Suitable reaction solvents include tetrahydrofuran, and the like. Compound 9a or 9b is then converted to a compound of Formula (Ia) or (Ib) by reacting it with a basic nitrogen containing R$^3$ group such as morpholine, piperidine, and the like.

Alternatively, 9a or 9b can be reacted with an oxidizing agent such as hydrogen peroxide to give a compound of Formula (Ia) or (Ib) where R$^3$ is hydrogen.

Alternatively, a compound of Formula (Ia) where E is —C(R$^5$)(R$^6$)X$^1$, R$^3$ is an amino containing group and is bonded to the carbon via the nitrogen atom and R$^4$, R$^1$, R$^{1a}$, R$^5$, and R$^6$ are as defined in the Summary of the Invention can be prepared by proceeding as in the following Reaction Scheme 5 below.

Scheme 5

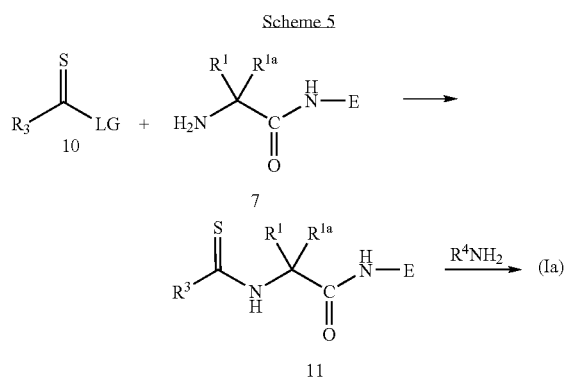

Reaction of a compound of formula 10 where $R^3$ is an amino containing group and is bonded to the carbon via the nitrogen atom with 7 under the presence of a suitable coupling agent such as 2-chloro-1-methylpyridinium iodide provides a compound of formula 11 which is then reacted with an amine of formula $R^4NH_2$ where $R^4$ is as defined in the Summary of the Invention to provide a compound of Formula (Ia). Compound 10 is prepared as described in Scheme 4 above e.g., reacting morpholine with 1,1'-thiocarbonyldiimidazole.

Additional Processes for Preparing Compounds of Formula (Ia) or (Ib):

A compound of Formula (Ia) or (Ib) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (Ia) or (Ib) can be prepared by reacting the free acid form of the compound with a pharmaceutically acceptable inorganic or organic base. Inorganic and organic acids and bases suitable for the preparation of the pharmaceutically acceptable salts of compounds of Formula (Ia) or (Ib) are set forth in the definitions section of this application. Alternatively, the salt forms of the compounds of Formula (Ia) or (Ib) can be prepared using salts of the starting materials or intermediates.

The free acid or free base forms of the compounds of Formula (Ia) or (Ib) can be prepared from the corresponding base addition salt or acid addition salt form. For example, a compound of Formula (Ia) or (Ib) in an acid addition salt form can be converted to the corresponding free base by treating with a suitable base (e.g., ammonium hydroxide solution, sodium hydroxide, and the like). A compound of Formula (Ia) or (Ib) in a base addition salt form can be converted to the corresponding free acid by treating with a suitable acid (e.g., hydrochloric acid, etc).

The N-oxides of compounds of Formula (Ia) or (Ib) can be prepared by methods known to those of ordinary skill in the art. For example, N-oxides can be prepared by treating an unoxidized form of the compound of Formula (Ia) or (Ib) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (Ia) or (Ib) can be prepared from the N-oxide of an appropriate starting material.

Compounds of Formula (Ia) or (Ib) in unoxidized form can be prepared from N-oxides of compounds of Formula (Ia) or (Ib) by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula (Ia) or (Ib) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (Ia) or (Ib) with a suitable carbamylating agent (e.g., 1,1-acyloxy-alkylcarbonochloridate, para-nitrophenyl carbonate, or the like).

Protected derivatives of the compounds of Formula (Ia) or (Ib) can be made by means known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula (Ia) or (Ib) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (Ia) or (Ib), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

Pharmacology and Utility

The compounds of the invention are selective inhibitors of cysteine proteases, in particular, cathepsin S, K, and/or F, and accordingly are useful for treating diseases in which cysteine protease activity contributes to the pathology and/or symptomatology of the disease. For example, the compounds of the invention are useful in treating autoimmune disorders, including, but not limited to, juvenile onset diabetes, multiple sclerosis, psoriasis, pemphigus vulgaris, Graves' disease, myasthenia gravis, systemic lupus erythemotasus, rheumatoid arthritis and Hashimoto's thyroiditis, allergic disorders, including, but not limited to, asthma, allogeneic immune responses, including, but not limited to, organ transplants or tissue grafts and endometriosis.

Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Biological Examples 1–5, infra.

Administration and Pharmaceutical Compositions

In general, compounds of Formula (Ia) or (Ib) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (Ia) or (Ib) may range from about 10 micrograms per kilogram body weight (g/kg) per day to about 20 milligram per kilogram body weight (mg/kg) per day, typically from about 100 μg/kg/day to about 10 mg/kg/day. Therefore, a therapeutically effective amount for a 80 kg human patient may range from about 1 mg/day to about 1.6 g/day, typically from about 1 mg/day to about 100 mg/day. In general, one of ordinary skill in the art, acting in reliance upon personal knowledge and the disclosure of this application, will be able to ascertain a therapeutically effective amount of a compound of Formula (Ia) or (Ib) for treating a given disease.

The compounds of Formula (Ia) or (Ib) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (Ia) or (Ib) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (Ia) or (Ib) in the composition may vary widely depending upon the type of formulation, size of a unit dosage, kind of excipients and other factors known to those of skill in the art of pharmaceutical sciences. In general, a composition of a compound of Formula (Ia) or (Ib) for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (Ia) or (Ib) are described in Example 1 below.

EXAMPLES

The present invention is further exemplified, but not limited by, the following examples that illustrate the preparation of compounds of Formula (Ia) or (Ib) (Examples) and intermediates (References) according to the invention.

General Procedures

Reference A

Synthesis of 2(RS)-benzyloxycarbonylamino-4(RS)-(2-methoxyphenyl)pentanoic acid

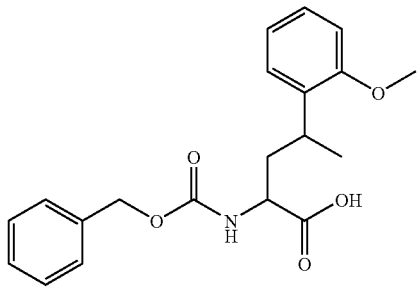

To d,l-2-methoxy-α-methylbenzyl alcohol (0.5 g, 3.29 mmol) was added 48% aq. HBr (2 mL) and the reaction mixture was stirred rapidly for 1.5 h. The reaction mixture was diluted with hexane (30 mL), washed with water, dried with MgSO$_4$, filtered, and evaporated under vacuum. The crude d,l-2-methoxy-α-methylbenzyl bromide was added to a solution of tributyltin hydride (0.67 mL, 2.49 mmol), Z-dehydroalanine methyl ester (0.25 g, 1.06 mmol), and 2,2'-azobisisobutyronitrile (15 mg, 0.09 mmol) in benzene (5 mL). The reaction mixture was heated at 80° C. under a nitrogen atmosphere for 5 h. Benzene was removed under vacuum and the residue was dissolved in methanol (20 mL). 2N KOH (5 mL) was added and the mixture was rapidly stirred at room temperature over night. Methanol was removed under vacuum and the residue was diluted with water (20 mL). The aqueous solution was washed with ether to remove the tin by products. The aqueous layer was acidified with 6 N HCl (aq.) and the product was extracted with ethyl acetate. The combined organic layers were washed with brine, dried with MgSO$_4$, filtered, and evaporated under vacuum to give 2-benzyloxycarbonylamino-4-(2-methoxyphenyl)pentanoic acid (190 mg, 0.53 mmol) as a mixture of diastereomers in sufficiently pure form to be used without further purification. MS: (M$^+$+H) 358, (M$^+$–H) 356.

Following the procedure described above, and utilizing appropriate starting materials the following amino acids were prepared:

2-benzyloxy-carbonylamino-4-(2-methoxyphenyl)hexanoic acid;
2-benzyloxy-carbonylamino-4-(4-fluorophenyl)pentanoic acid;
2-benzyloxy-carbonylamino-4-(4-chlorophenyl)pentanoic acid;
2-benzyloxy-carbonylamino-4-(4-methoxyphenyl)pentanoic acid;
2-benzyloxy-carbonylamino-4-(2-trifluoromethylphenyl)pentanoic acid;
2-benzyloxy-carbonylamino-4-(3-trifluoromethylphenyl)pentanoic acid;
2-benzyloxy-carbonylamino-4-(napth-1-yl)pentanoic acid;
2-benzyloxy-carbonylamino-4-(2,6-dimethylphenyl)pentanoic acid;
2-benzyloxy-carbonylamino-4-(2,4-difluorophenyl)pentanoic acid;
2-benzyloxy-carbonylamino-4-(2,4-dimethylphenyl)pentanoic acid;
2-benzyloxy-carbonylamino-4-(2,5-dimethylphenyl)pentanoic acid; and
2-benzyloxy-carbonylamino-4-(2,4-dichlorophenyl)pentanoic acid.

The benzyloxycarbonyl group can be removed as described in Reference C below to give the corresponding free amino acid.

Reference B

Synthesis of 2(S)-2,6-difluorophenylalanine

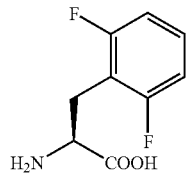

Step 1

N-(Benzyloxycarbonyl)-α-phosphonoglycine trimethyl ester (Aldrich No. 37,635-3; 6.7 g, 20 mmol) and 1,8-diazabicyclo[5,4,0]undec-7-ene (Aldrich No. 13, 900-9; 3.3 mL, 22 mmol) were dissolved in methylene chloride (11 mL) and stirred at room temperature for 15 min., and then cooled to <−30° C. A solution of 2,6-difluorobenzaldehyde (1.9 mL, 20 mmol) in methylene chloride (25 mL) was added to the reaction mixture dropwise over 20 min. The reaction mixture was stirred for another 20 min., and then allowed to warm up to room temperature for 30 min. The reaction mixture was then poured into ethyl ether (300 mL) and washed with 1 N HCl, brine and dried over $MgSO_4$. Rotary evaporation gave 2-benzyloxycarbonylamino-3-(2,6-difluorophenyl)acrylic acid methyl ester. This crude product was purified by chromatography on a Medium Pressure Liquid Column (MPLC) eluting with 20% ethyl acetate/80% hexane to give pure product (5 g, 72% yield, liquid).

Step 2

A mixture of 2-benzyloxycarbonylamino-3-(2,6-difluorophenyl)acrylic acid methyl ester (14.4 mmol), and catalyst, (+)-1,2-bis-[(2S,5S)2,5-diethylphopholano]benzene (cyclooctadiene)rhodium (1) trifluoromethanesulfonate (Strem. Chemical No. 45-0151; 104 mg, 0.14 mmol) was dissolved in ethanol (150 mL). Hydrogenation was performed at 50 psi $H_2$ at room temperature over 2 days. The solvent was then removed by rotary evaporation to give 2(S)-benzyloxycarbonylamino-3-(2,6-difluorophenyl)propionic acid methyl ester.

Step 3

2(S)-Benzyloxycarbonylamino-3-(2,6-difluorophenyl) propionic acid methyl ester (5 g, 14.4 mmol) was dissolved in methanol (60 mL) and cooled on ice. 1 N NaOH (22 mL, 22 mmol) was added dropwise over 15 min. The reaction mixture was removed from cooling and continue stirring at room temperature for 4 h. The solvent was then removed by rotary evaporation. The residue was treated with water (100 mL) and then with 1 N HCl to adjust the pH to 4. The product was extracted with ethyl acetate (300 mL, 200 mL). Evaporation of the solvent and crystallization of the residue from methylene chloride/hexane gave 2(S)-benzyloxycarbonylamino-3-(2,6-difluorophenyl)propionic acid (4.6 g, 13.7 mmol, 94% yield).

Step 4

2(S)-Benzyloxycarbonylamino-3-(2,6-difluorophenyl)-propionic acid was hydrogenated at 50 psi in ethanol (25 mL) in the presence of 5% palladium on activated carbon (600 mg) for 24 h. The catalyst was removed by filtration through celite and the solvent evaporated to give a residue which was crystalized from ethyl ether to give 2(S)-2,6-difluorophenylalanine-(2.2 g, 11 mmol, 80% yield). $^1$H NMR (DMSO-$d_6$): δ 7.28 (m, 1H), 7.0 (t, J=7.6 Hz, 2H), 2.77 (m, 2H). MS: 202.2 (M+1), 199.7(M−1).

Reference C

Synthesis of 2(RS)-amino-4(RS)-6,6-trimethylheptanoic acid

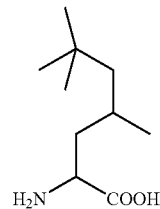

Step 1

To a mixture of the 3,5,5-trimethylhexanal (17.4 mL, 0.10 mol), ammonium chloride (53.5 g, 0.205 mol) and diethyl ether (113 mL) was added sodium cyanide (7.35 g, 0.15 mol) in water (38 mL). The reaction mixture was allowed to stir vigorously for 16 h. The layers were separated. The aqueous layer was extracted with diethyl ether. The combined organic layer was then extracted with 1 N HCl. Saturated sodium bicarbonate was then added until 1-cyano-3,5,5-trimethyl-hexylamine was completely precipitated. Vacuum filtration and washing with 5 mL ice cold water followed by lyophilization gave 1-cyano-3,5,5-trimethylhexylamine (5.805 g, 0.034 mol, 34.5%) as a white solid.

Step 2

1-Cyano-3,5,5-trimethylhexylamine (1.02 g, 5.0 mmol) was treated with 6 N HCl (10 mL) and heated at reflux for 30 h. The reaction mixture was allowed to cool to room temperature. Water (50 mL) was added, and the mixture was washed with diethyl ether. The aqueous layer was basified to pH 8.5 with 2 M KOH. A white precipitate formed which was collected by vacuum filtration and lyophilized to give 2(RS)-amino-4(RS),6,6-trimethyl-heptanoic acid (364 mg).

Reference D

Synthesis of 2(RS)-amino-4-methyl-4-phenylpentanoic acid

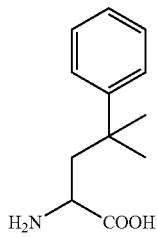

Step 1

4-Methyl-4-phenyl-1-pentene was prepared by reacting 2-phenyl-2-propanol with 3-(trimethylsilyl)propene by the method of Cella, *J. Org. Chem.*, 1982, 47, 2125–2130.

Step 2

4-Methyl-4-phenyl-1-pentene was ozonolyzed at −78° C. in dichloromethane followed by dimethyl sulfide quenching to give crude product which was purified by silica gel chromatography to give 3-methyl-3-phenylbutanal which was then converted to the title compound by proceeding as described in Reference D above.

Reference E

Synthesis of 2(S)-amino-4-phenylpent-4-enoic acid

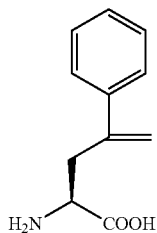

Step 1

Methyl triphenylphosphonium bromide (1.12 g, 3.14 mmol, 2.0 equiv.) was dissolved in THF (15 mL) and cooled to 0° C. Sodium bis(trimethylsilyl)amide (3.14 mL) was added and the reaction mixture was stirred for 30 min. 2(S)-Benzyloxycarbonyl-amino-3-benzoylpropionic acid ethyl ester (0.54 g, 1.57 mmol, 1.0 equiv. prepared by procedures outlined in Lin, W., et. al., *Synthesis* 2001, No. 7, 1007–1009 was dissolved in THF (5 mL) and added to the reaction. After warming to room temperature, the reaction mixture was quenched with saturated ammonium chloride and partitioned between water and EtOAc. After concentration of the organic phase, purification was carried out with flash chromatography to provide 2-benzyl-oxycarbony-lamino-4-phenyl-pent-4-enoic acid ethyl ester. Removal of the benzyloxycarbonyl group as described above, provided the title compound.

Reference F

Synthesis of 2(RS)-benzyloxycarbonylamino-4-ethylhexanoic acid

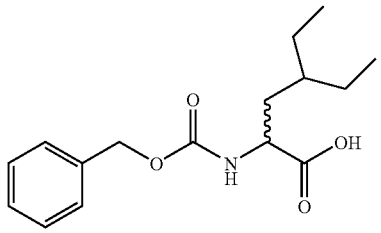

Step 1

A mixture of 2-benzyloxycarbonylaminomalonic acid diethyl ester (Bladon, C. M. *J. Chem. Soc. Perkin Trans.* 1990, 1, 1151–1158) (1.237 g), iodo-2-ethylbutane (1.272 g) and lithium hydroxide (0.287 g) in N-methylpyrrolidone (8 mL) was stirred for 2 days at room temperature and then diluted with ice water. The aqueous solution was extracted with ether and the product purified by chromatography on silica gel to give 2-benzyloxycarbonylamino-2-(2-ethylbutyl)malonic acid diethyl ester (0.520 g).

Step 2

A solution of 2-benzyloxycarbonylamino-2-(2-ethylbutyl)malonic acid diethyl ester (0.520 g) in ethanol (5 mL) was treated with sodium hydroxide (2.91 mL, 1 N) and then stirred at room temperature for 8 h. The reaction mixture was diluted with water and acidified with HCl and the product was then extracted with ethyl acetate to give 2-benzyloxycarbonylamino-2-(2-ethylbutyl)malonic acid monoethyl ester (0.461 g).

Step 3

2-Benzyloxycarbonylamino-2-(2-ethylbutyl)malonic acid monoethyl ester was heated at 75° C. in ethanol (5 mL) with sodium hydroxide (5 mL, 1 N) for 3 h and 2-benzyloxycarbonyl-amino-2-(2-ethylbutyl)malonic acid was isolated by extraction of the acidified reaction mixture. 2-Benzyloxycarbonylamino-2-(2-ethylbutyl)malonic acid was heated at 103° C. for 1 h and the resulting residue was purified by column chromatography on silica gel to give 2(RS)-benzyloxycarbonylamino-4-ethylhexanoic acid (0.220 g).

Reference G

Synthesis of 2(S)-benzyloxycarbonylamino-3-pyrazol-1-ylpropionic acid

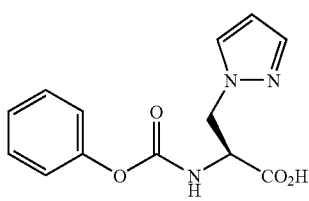

The title compound was prepared by treating (S)-benzyloxycarbonylserine-β-lactone with pyrazole in acetonitrile at 60° C. for 16 h (see *J. Am. Chem. Soc.*, 1985, 107, 7105–7109).

Following the procedure described above, but substituting pyrazole with 1,2,4-triazole and 1,2,3-triazole provided 2(S)-benzyloxycarbonylamino-3-[1,2,4]-triazol-1-ylpropionic acid and 2(8)-benzyloxycarbonylamino-3-[1,2,3]-triazol-1-ylpropionic acid respectively.

Reference H

Synthesis of 2(S)-(tert-butoxycarbonyl)amino-1-(oxazolo[4,5-b]pyridin-2-yl)butan-1-ol

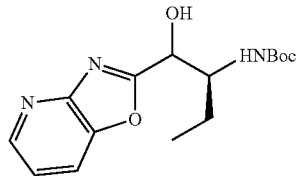

Step 1

A mixture of 2-amino-3-hydroxypyridine (11 g, 100 mmol), triethylorthoformate (80 mL) and p-toluenesulfonic acid (61 mg) was heated at 140° C. for 8 h. Excess triethylorthoformate was removed under vacuum and oxazolo[4,5-b]pyridine was crystalized from ethyl acetate (9 g).

Step 2

In a clean roundbottom flask equipped with stir bar was placed oxazolo[4,5-b]pyridine (600 mg, 5 mmol) in THF (30 mL) and the reaction mixture was cooled to 0° C. under $N_2$ atomosphere. Isopropylmagnesium chloride (2 M in THF, 2.5 mL, 5 mmol) was added. After stirring for 1 h at 0° C., (S)-2-(tert-butoxycarbonyl)aminobutyraldehyde (573 mg, 3 mmol) in THF (20 mL) was added. The ice bath was removed and the reaction mixture was allowed to warm to room temperature. After 2 h, the reaction mixture was quenched with saturated ammonium chloride solution and concentrated to dryness. The residue was extracted with EtOAc, then washed with brine, dried with anhyd. $MgSO_4$, filtered and concentrated. The crude product was purified by chromatograph to yield 383 mg of the desired compound.

$H^1$ NMR (DMSO-$d_6$): δ 8.42 (m, 1H), 8.18 (m, 1H), 7.3(m, 1H), 6.8–6.6 (dd, d, 1H, OH, diastereomer), 6.3–6.02 (d, d, 1H, NH, diastereomer), 4.82–4.5 (m,m, 1H, diastereomer), 1.8–1.3 (m, 2H), 1.2–1.05 (s,s, 9H, diastereomer), 0.89 (m, 3H). MS: 306.2 (M−1), 308.6 (M+1).

Reference I

Synthesis of 2(S)-(tert-butoxycarbonyl)amino-3-thiazol-2-ylpropionic acid

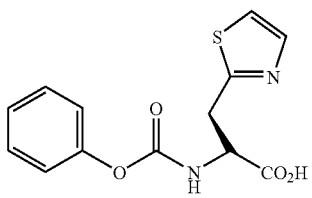

To 2-tert-butoxycarbonylamino-3-thiazol-2-yl-propionic acid methyl ester (500 mg, 1.75 mmol) in a mixture of acetonitrile (6 mL) and 0.2 M aqueous $NaHCO_3$ (12 mL) was added Alcalase (2.4 L, 0.08 mL), and the solution was stirred vigorously at room temperature for about 2.5 h. The reaction mixture was then evaporated at 30° C. to remove acetonitrile, and the aqueous residue was washed with ether. The aqueous phase was acidified with 6 N HCl to pH 3 and the solution was extracted with ethyl acetate. The combined organic layers were then dried and evaporated to yield 2(S)-tert-butoxycarbonyl-amino-3-thiazol-2-yl-propionic acid (204 mg).

Reference J

Synthesis of (S)-4-amino-2,2-difluoro-3-hydroxyhexanoic acid dimethylamide

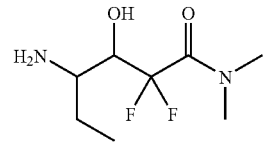

Activated zinc dust (2.16 g, 33 mmol) was suspended in dry THF (2 mL). A mixture of ethyl bromodifluoro acetate (6.5 g, 32 mmol) and (1S)-(1-formylpropyl)carbamic acid tert-butyl ester (2 g, 10.7 mmol), in THF (10 mL), was added over 20 min while the reaction mixture was sonicated. After complete addition, sonication was continued for a further 30 min. The reaction mixture was then diluted with ethyl acetate (200 mL) and washed with 1N aqueous $KHSO_4$, brine, dried with magnesium sulfate and evaporated. The crude product was dissolved in ethanol (15 mL) and a solution of dimethylamine (40% in water; 2 mL) was added. After stirring for 16 h at ambient temperature, the solvents were evaporated and the product was purified by flash chromatography on silica gel (hexane/ethyl acetate ratio of 3:1) to yield 200 mg 4(S)-Boc-amino-2,2-difluoro-3-hydroxy-hexanoic acid dimethylamide of colorless oil which was dissolved in a mixture of TFA/dichloromethane (1:1; 6 mL), stirred for 1 h and evaporated to dryness. The product, (S)-4-amino-2,2-difluoro-3-hydroxyhexanoic acid dimethylamide, was obtained as the TFA salt and used without further purification.

Reference K

Synthesis of (S)-3-amino-2-hydroxy-pentanoic acid benzylamide

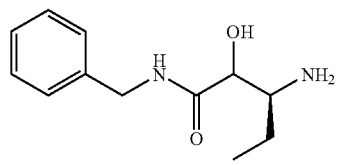

Step 1

(1S)-(2-Cyano-1-ethyl-2-hydroxyethyl)carbamic acid tert-butyl ester (10 g, 46.7 mmol) was dissolved in 1,4-dioxane (100 mL). Anisole (5 mL) was added and then concentrated HCl (100 mL). The reaction mixture was heated under reflux for 24 h. The reaction mixture was evaporated to dryness under vacuum and re-dissolved in 100 mL water. The solution was washed with ether and then neutralized with saturated aqueous NaHCO₃. Di-tert-butyl dicarbonate (10 g, 46 mmol) was added with 1,4-dioxane (200 mL), and the reaction mixture was stirred at ambient temperature for 24 h. The dioxane was removed under vacuum and the remaining aqueous solution was washed with ether. The solution was acidified with 1N HCl and extracted with ethyl acetate. The combined organic layers were washed with brine, dried with magnesium sulfate and evaporated to yield 3-tert-Butoxycarbonylamino-2-hydroxy-pentanoic acid (4.5 g) as yellowish oil.

Step 2

3-tert-Butoxycarbonylamino-2-hydroxy-pentanoic acid (300 mg, 1.2 9 mmol) was combined with EDC (400 mg, 2.1 mmol) and HOBt (400 mg, 2.6 mmol). A solution of benzylamine (0.22 mL) and 4-methylmorpholine (0.5 mL) in dichloromethane (4 mL) was added in one portion. The reaction mixture was stirred at ambient temperature for 2 h. After dilution with ethyl acetate (150 mL), the solution was washed with 1 N aqueous HCl, water, saturated aqueous NaHCO₃ solution and brine. The resultant mixture was dried with magnesium sulfate and evaporated under vacuum to yield (S)-3-amino-2-hydroxy-pentanoic acid benzylamide (380 mg) as a white solid.

Step 3

(S)-3-Amino-2-hydroxy-pentanoic acid benzylamide was dissolved in a mixture of TFA/dichloromethane (1:1; 6 mL), stirred for 1 h and evaporated to dryness. (S)-3-amino-2-hydroxy-pentanoic acid benzylamide was obtained as the TFA salt and used without further purification.

Reference L

Synthesis of (S)-2-amino-1-(3-phenyl-[1,2,4]oxadiazol-5-yl)-butan-1-ol

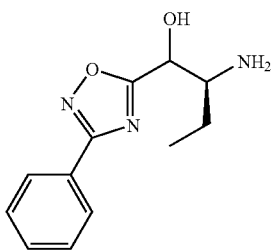

3-tert-Butoxycarbonylamino-2-hydroxy-pentanoic acid (500 mg, 2.14 mmol) was combined with EDC (600 mg, 3.14 mmol), HOBt (600 mg, 3.92 mmol), and N-hydroxybenzamidine (292 mg, 2.14 mmol). Dichloromethane (10 mL) was added and then 4-methylmorpholine (1 mL). The reaction mixture was stirred at ambient temperature for 16 h. After dilution with ethyl acetate (200 mL), the solution was washed with water (30 mL), saturated aqueous NaHCO₃ solution and brine, dried with MgSO₄ and evaporated under vacuum. The crude product was dissolved in pyridine (10 mL) and heated at 80° C. for 15 h. The pyridine was evaporated under vacuum and the residue was purified by flash chromatography on silica gel (eluent: ethyl acetate) to yield (290 mg, 0.83 mmol) of (S)-2-tert-butoxycarbonylamino-1-(3-phenyl-[1,2,4]oxadiazol-5-yl)-butan-1-ol. (S)-2-tert-Butoxycarbonylamino-1-(3-phenyl-[1,2,4]oxadiazol-5-yl)-butan-1-ol (145 mg, 0.41 mmol) was dissolved in CH₂Cl₂ (4 mL) and TFA (4 mL) was added. After stirring for 1 h, the reaction mixture was evaporated to dryness to yield (S)-2-amino-1-(3-phenyl-[1,2,4]oxadiazol-5-yl)-butan-1-ol.

Reference M

Synthesis of (S)-2-amino-1-(2-phenyl-[1,3]dithian-2-yl)-hexan-1-ol

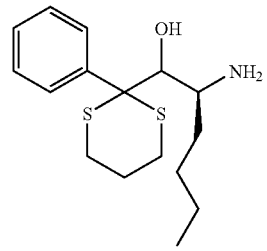

Step 1

2-Phenyl-1,3-dithiane (Aldrich) (3.79 g; 19.3 mmol) was mixed with dry distilled THF (20 mL) under a nitrogen atmosphere. The solution was cooled to −60° C. and n-butyl lithium (1.6M in pentane, 1.56 mmol, 9.74 mL) was added slowly by syringe. The reaction mixture was warmed to −20° C. and held at that temperature for 30 min., and then held at −10° C. for 15 min. The yellow solution was cooled to −78° C. and (1-formyl-pentyl)-carbamic acid tert-butyl ester (1.6 g, 1.4 mmol, in 5 mL THF) was added rapidly (over 20 seconds) and 60 seconds later a mixture of 2 mL acetic acid and 5 mL THF was added rapidly. After warming to 23° C. the solution was concentrated at reduced pressure. Excess 2-phenyl-1,3-dithiane was removed by its crystallization away from the desired product using a minimum of ethyl acetate in hexane. The mother liquors were concentrated and chromatographed using a hexane-ethyl acetate gradient to afford {1-[hydroxy-(2-phenyl-[1,3]dithian-2-yl)-methyl]-pentyl}-carbamic acid tert-butyl ester. (1.7 g, 56% yield).

Step 2

To {1-[hydroxy-(2-phenyl-[1,3]dithian-2-yl)-methyl]-pentyl}-carbamic acid tert-butyl ester (608 mg, 1.47 mmol) in dioxane (2.7 mL) at 10° C. was added hydrochloric acid (2.7 mL, 4 M in dioxane). The solution was warmed to 23° C. After 3 h, the solution was diluted with toluene (5 mL) and concentrated under reduced pressure. The gummy solid was washed with diethyl ether resulting in the hydrochloride salt of 2-amino-1-(2-phenyl-[1,3]dithian-2-yl)-hexan-1-ol, 414 mg, 82% as a free flowing solid after removal of excess ether under reduced pressure.

Reference N

Synthesis of 3-amino-4-hydroxypyrrolidine-1-carboxylic acid tert-butyl ester

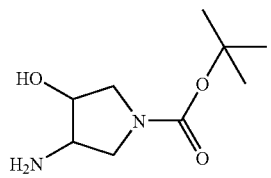

6-Oxa-3-aza-bicyclo[3.1.0]hexane-3-carboxylic acid tert-butyl ester (12.1 g, 65.3 mmol) was dissolved in a 8:1 methanol/water mixture (108 mL). Ammonium chloride (15 g) and sodium azide (21.4 g, 329 mmol) was added and the reaction mixture was heated at 60° C. overnight. After dilution with ether (500 mL), the reaction mixture was washed with saturated aqueous NaHCO₃ (200 mL) and brine (200 mL), dried with MgSO₄ and evaporated under vacuum. The crude product was dissolved in methanol (200 mL). 10% Palladium on activated carbon (1.5 g) was added and the reaction mixture was stirred at ambient temperature under a hydrogen atmosphere until TLC analysis showed the disappearance of the starting material. The reaction mixture was filtered through a pad of Celite and evaporated to dryness under vacuum. The product was purified by flash chromatography on silica gel using 5% methanol in ethyl acetate to 20% methanol, 3% triethylamine in ethyl acetate to give 4.3 g of 3-amino-4-hydroxy-pyrrolidine-1-carboxylic acid tert-butyl ester as yellowish solid.

Reference O

Synthesis of 2-amino-2-methyl-1-oxazolo[4,5-b]pyridin-2-yl-propan-1-ol

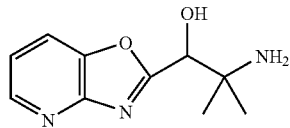

Step 1

2-Amino-2-methyl-1-propanol (17.8 g, 200 mmol) was dissolved in a mixture of water and dioxane (100 mL) and cooled to 0° C. NaOH (8 g, 200 mmol) and di-t-butyl-dicarbonate (52.4 g, 240 mmol) were added and the reaction was allowed to warm to room temperature with stirring for 2 h. After removing the dioxane, the residue was extracted with EtOAc, washed with brine, dried with anhydrous MgSO₄, filtered and concentrated to yield 35 g of 2-Boc-amino-2-methyl-1-propanol.

Step 2

A solution of oxalyl chloride (15.24 g, 120 mmol) in 200 mL of MeCl₂ was stirred and cooled to −60° C. followed by the drop wise addition of dimethylsulfoxide (19.7 g, 252 mmol) in 60 mL of MeCl₂. After 10 min, a solution of 2-Boc-amino-2-methyl-1-propanol (18.9 g, 100 mmol) in MeCl₂ (60 mL) was added drop wise at −70° C. The reaction mixture was allowed to warm to −40° C. for 10 min followed by cooling to −70° C. before the addition of a solution of triethylamine (28.28 g, 280 mmol) in MeCl₂ (60 mL). The reaction mixture was allowed to warm to room temperature over a two-hour period and 40 mL of saturated sodium dihydrogen phosphate was added. The organic layer was washed with brine and dried over MgSO₄. The solvent was removed to yield 17.3 g of 2-Boc-amino-2-methylpropionaldehyde.

Step 3

A mixture of 2-amino-3-hydroxypyridine (11 g, 100 mmol), triethylorthoformate (80 mL) and p-toluenesulfonic acid (61 mg) was heated at 140° C. for 8 h. Excess triethylorthoformate was removed under vacuum. The product was crystallized from ethyl acetate to yield 9 g of 1-oxazolo[4,5-b]pyridine.

Step 4

To a stirred solution of the 1-oxazolo[4,5-b]pyridine (2.4 g, 20 mmol) in THF (100 mL) was added n-BuLi (1.6 M solution in 12.5 mL of hexane) drop wise under N₂ at −78° C. After 1 h, MgBr.Et₂O (5.16 g, 20 mmol) was added and the reaction mixture was allowed to warm to −45° C. for 1 h before being treated with 2-Boc-amino-2-methylpropionaldehyde (2.24 g, 12 mmol) in THF (20 mL). The reaction mixture was stirred for 1 h, quenched with saturated NH₄Cl, and extracted with ethyl acetate. The organic layer was washed with brine, dried with MgSO₄ and concentrated. The residue was purified by silica gel column chromatography to yield 2-Boc-amino-2-methyl-1-oxazolo[4,5-b]pyridin-2-yl-1-propanol (1.18 g).

Step 5

2-Boc-amino-2-methyl-1-oxazolo[4,5-b]pyridin-2-yl-1-propanol (156 mg, 0.508 mmol) and MeCl₂ (5 mL) were mixed and TFA (0.5 mL) was added at room temperature. After stirring for 1 h, the solvent and excess TFA were removed under vacuum to produce 2-amino-2-methyl-1-oxazolo[4,5-b]pyridin-2-yl-propan-1-ol. TFA salt (165 mg).

Reference P

Synthesis of (S)-2-amino-1-(5-methoxymethyl-[1,3,4]oxadiazol-2-yl)-butan-1-ol

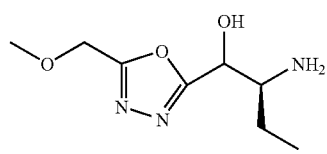

Step 1

(S)-(+)-2-amino-1-butanol (50 g, 561 mmol) in a mixture of water and dioxane (200 mL of water and :200 mL) dioxane was cooled to 0° C. and mixed with NaOH (26.9 g, 673 mmol) and di-tert-butyl-dicarbonate (146.96 g, 673 mmol). After the addition, the reaction was allowed to warm to room temperature. The reaction mixture was stirred for 2 h. After removing the dioxane, the residue was extracted with EtOAc, then washed with brine and dried with anhydrous MgSO₄, filtered and concentrated. Without further purification, the crude (S)-2-Boc-amino-1-butanol (120 g) was used for next step reaction.

Step 2

A solution of oxalyl chloride (40.39 g, 265 mmol) in MeCl₂ (700 mL) was stirred and cooled to −60° C. Dimethylsulfoxide (51.7 g, 663 mmol) in MeCl₂ (100 mL) was added dropwise. After 10 min., a solution of (S)-2-Boc-amino-1-butanol (50 g, 265 mmol) in MeCl₂ (100 mL) was added dropwise at −70° C. The reaction mixture was allowed to warm to 40° C. for 10 min. and then cooled to −70° C. again. A solution of triethylamine (74.9 g, 742 mmol) in MeCl₂ (100 mL) was added. The reaction mixture was allowed to warm to room temperature over 2 h. Saturated sodium dihydrogen phosphate (100 mL) was added, and then the organic layer was washed with brine and dried over MgSO₄. The solvent was removed to yield 45 g of (S)-2-Boc-amino-butyraldehyde(1-formyl-propyl)-carbamic acid tert-butyl ester.

Step 3

A mixture of methyl methoxyacetate (52 g, 500 mmol), hydrazine hydrate (30 mL) was heated to reflux for 8 h. Excess hydrazine and water were removed under vacuum. The residue was extracted with n-butanol, dried with Na₂SO₄. Excess n-butanol was removed to yield 45 g of hydrazide.

Step 4

A mixture of above hydrazide (45 g), triethylorthoformate (146 mL) and p-toluenesulfonic acid (61 mg) was heated at 140° C. for 8 h. Excess triethylorthoformate was removed under vacuum. The product was purified by silica gel column chromatography to yield 4.6 g of 2-methoxymethyl-1,3,4-oxadiazole.

Step 5

To a stirred solution of 2-methoxymethyl-1,3,4-oxadiazole (4.6 g, 40 mmol) in THF (100 mL) was added n-BuLi (1.6 M solution in 25.2 mL of hexane) dropwise under $N_2$ at −78° C. After 1 h, $MgBr.Et_2O$ (10.4 g, 40.3 mmol) was added and the reaction mixture was allowed to warm to −45° C. for 1 h before being treated with (S)-2-Boc-amino-propanylaldehyde butyraldehyde (5.28 g, 28.25 mmol) in THF (20 mL). The reaction mixture was stirred for 1 h, quenched with saturated $NH_4Cl$, and extracted with ethyl acetate. The organic layer was washed with brine, dried with $MgSO_4$ and concentrated. The residue was purified by silica gel column chromatography to yield (S)-2-Boc-amino-1-(5-methoxymethyl-[1,3,4]-oxadiazole-2-yl)-1-propanol butanol (500 mg).

Step 6

2-Boc-amino-1-(5-methoxymethyl-[1,3,4]-oxadiazole-2-yl)-1-propanol butanol (500 mg, 1.66 mmol), and $MeCl_2$ (5 mL) were mixed and TFA (0.5 mL) was added at room temperature. After stirring for 1 h, the solvent and excess TFA were removed under vacuum to produce (S)-2-amino-1-(5-methoxymethyl-[1,3,4]oxadiazol-2-yl)-butan-1-ol. TFA salt (340 mg).

Reference Q

Synthesis of (S)-2-amino-1-(5-phenyl-[1,3,4]oxadiazol-2-yl)-1-butan-1-ol

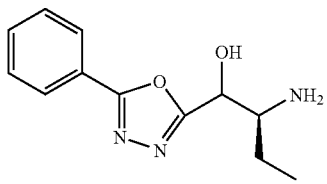

Step 1

A mixture of the benzoic hydrazide (22.5 g, 165 mmol), triethylorthoformate (150 mL) and p-toluenesulfonic acid (300 mg) was heated at 120° C. for 12 h. Excess triethylorthoformate was removed under vacuum and the residue was purified by silica gel column chromatography to produce 2-phenyl-[1,3,4]-oxadiazole (14.5 g).

Step 2

To a stirred solution of the 2-phenyl-[1,3,4]oxadiazole (10 g, 68.5 mmol) in THF (100 mL) was added n-BuLi (1.6 M solution in 42.8 mL of hexane) dropwise under $N_2$ at −78° C. After 1 h, $MgBr.Et_2O$ (17.69 g, 68.5 mmol) was added and the reaction mixture was allowed to warm to −45° C. for 1 h before being treated with (S)-2-Boc-aminobutyra-aldehyde (7.8 g, 41 mmol) in THF (20 mL). The reaction mixture was stirred for 1 h, quenched with saturated $NH_4Cl$, and extracted with ethyl acetate. The organic layer was washed with brine, dried with $MgSO_4$ and concentrated. The residue was purified by silica gel column chromatography to yield 2-((S)-2-Boc-amino-1-hydroxybutyl)-5-phenyl-[1,3,4]-oxadiazole (9.7 g).

Step 3

2-((S)-2-Boc-amino-1-hydroxybutyl)-5-phenyl-[1,3,4]-oxadiazole (505 mg, 1.5 mmol) and $MeCl_2$ (5 mL) were mixed and TFA (1 mL) was added at room temperature. After stirring for 1 h, the solvent and excess TFA were removed under vacuum to produce 530 mg of (S)-2-amino-1-(5-phenyl-[1,3,4]oxadiazol-2-yl)-1-butanol TFA salt.

Reference R

Synthesis of (S)-2-amino-1-oxazolo[4,5-b]pyridin-2-yl-butan-1-ol

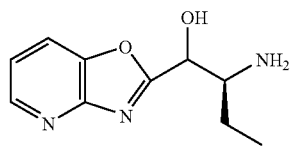

Step 1

A mixture of 2-amino-3-hydroxypyridine (25 g, 227 mmol), triethylorthoformate (75 mL) and p-toluenesulfonic acid (61 mg) was heated at 140° C. for 8 h. Excess triethylorthoformate was removed under vacuum. The product was crystallized from ethyl acetate to yield 22.5 g of oxazolo[4,5-b]pyridine.

Step 2

To a stirred solution of the oxazolo[4,5-b]pyridine (12 g, 100 mmol) in THF (300 mL) was added n-BuLi (1.6 M solution in 62.5 mL of hexane) drop wise under $N_2$ at −78° C. After 1 h, $MgBr.Et_2O$ (25.8 g, 100 mmol) was added and the reaction mixture was allowed to warm to −45° C. for 1 h before being treated with (S)-2-Boc-amino-butylaldehyde (11.46 g, 60 mmol) in THF (50 mL). The reaction mixture was stirred for 1 h, quenched with saturated $NH_4Cl$, and extracted with ethyl acetate. The organic layer was washed with brine, dried with $MgSO_4$ and concentrated. The residue was purified by silica gel column chromatography to yield (S)-2-Boc-amino-1-(oxazolo[4,5-b]pyridin-2-yl)-1-butanol (14.1 g).

Step 3

(S)-2-Boc-amino-1-(oxazolo[4,5-b]pyridin-2-yl)-1-butanol (311 mg, 1 mmol) and $MeCl_2$ (5 mL) were mixed and TFA (1 mL) was added at room temperature. After stirring for 1 h, the solvent and excess TFA were removed under vacuum to produce 355 mg of (5)-2-amino-1-oxazolo[4,5-b]pyridin-2-yl-butan-1-ol. TFA salt.

Reference S

Synthesis of (S)-2-amino-1-(5-pyridin-4-yl-[1,3,4]oxadiazol-2-yl)-butan-1-olne

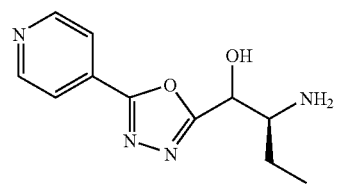

Step 1

A mixture of the isonicotinic hydrazide (13.7 g, 100 mmol), triethylorthoformate (60 mL) and p-toluenesulfonic acid (30 mg) was heated at 130° C. for 12 h. Excess triethylorthoformate was removed under vacuum. The crude was crystallized from ethyl acetate to give 14.8 g of 5-pyridin-4-yl-[1,3,4]oxadiazole.

Step 2

To a stirred solution of the 5-pyridin-4-yl-[1,3,4]oxadiazole (11.5 g, 78.2 mmol) in THF (300 mL) was added HMPA (5 ML) and n-BuLi (1.6 M solution in 48.9 mL of hexane) dropwise under $N_2$ at −78° C. After 1 h, $MgBr.Et_2O$ (20.2 g, 78.2 mmol) was added and the reaction mixture was allowed to warm to −45° C. for 1 h before being treated with 2-Boc-amino-butyraldehyde (9.7 g, 50.8 mmol) in THF (50 mL). The reaction mixture was stirred for 1 h, quenched with saturated $NH_4Cl$, and extracted with ethyl acetate. The organic layer was washed with brine, dried with $MgSO_4$ and concentrated. The residue was purified with silica gel column chromatography to yield (S)-2-Boc-amino-1-(5-pyridin-4-yl-[1,3,4]oxadiazol-2-yl)-butan-1-ol (3.5 g).

Step 3

(S)-2-Boc-amino-1-(5-pyridin-4-yl-[1,3,4]oxadiazol-2-yl)-butan-1-ol (334 mg, 1 mmol) and $MeCl_2$ (5 mL) were mixed and TFA (0.5 mL) was added at room temperature. After stirring for 1 h, the solvent and excess TFA were removed under vacuum to produce 350 mg of 2-amino-1-(5-pyridin-4-yl-[1,3,4]oxadiazol-2-yl)-butan-1-ol. TFA salt.

Reference T

Synthesis of (S)-2-amino-1-(5-pyridin-3-yl-[1,3,4]oxadiazol-2-yl)-butan-1-ol

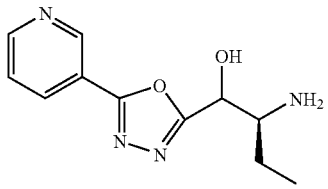

Step 1

To a stirred solution of the 3-[1,3,4]oxadiazol-2-yl-pyridine (5 g, 34 mmol) in THF (100 mL) was added HMPA (5 mL) and n-BuLi (1.6 M solution in hexane, 21.25 mL) drop wise under $N_2$ at −78° C. After 1 h, $MgBr.Et_2O$ (8.77 g, 34 mmol) was added and the reaction mixture was allowed to warm to −45° C. for 1 h before being treated with (S)-2-Boc-amino-butyraldehyde (4.22 g, 22.1 mmol) in THF (20 mL). The reaction mixture was stirred for 1 h, quenched with saturated $NH_4Cl$, and extracted with ethyl acetate. The organic layer was washed with brine, dried with $MgSO_4$ and concentrated. The residue was purified with silica gel column chromatography to yield (S)-2-Boc-amino-1-(5-pyridin-3-yl-[1,3,4]oxadiazol-2-yl)-butan-1-ol (1.5 g).

Step 2

(S)-2-Boc-amino-1-(5-pyridin-3-yl-[1,3,4]oxadiazol-2-yl)-butan-1-ol (167 mg, 0.5 mmol) and $MeCl_2$ (5 mL) were mixed and TFA (0.5 mL) was added at room temperature. After stirring for 1 h, the solvent and excess TFA were removed under vacuum to produce 180 mg of (S)-2-amino-1-(5-pyridin-3-yl-[1,3,4]oxadiazol-2-yl)-butan-1-ol. TFA salt.

Reference U

Synthesis of (S)-2-amino-1-benzoxazol-2-ylbutan-1-ol hydrochloride

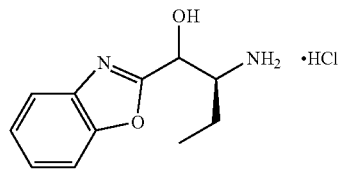

Step 1

To a solution of benzoxazole (28.6 g, 240 mmol) in toluene (150 mL) was added during ca 20 min., at about −4° C. a 2 M solution of isopropyl-magnesium chloride in THF (120 mL, 240 mmol). The red-brown mixture was stored at ca −4° C. and used as needed.

Step 2

To a solution of (S)-2-Boc-aminobutanol (50 g; 264 mmol) in dichloromethane (500 mL) and water (350 mL) were added at 20° C. TEMPO (0.01 eq), sodium bromide (1 eq) and sodium hydrogencarbonate (3 eq). The reaction mixture was stirred at 0° C. and diluted bleach (1.3 eq, 450 mL) was added over 40 min. The reaction mixture was stirred for 30 min. at 0° C. and then quenched with aq. thiosulfate. After decantation and extractions (dichloromethane), the organic phase was washed with brine, dried and concentrated in vacuo to dryness, giving (S)-2-(tert-butoxycarbonyl)-aminobutyraldehyde as a low-melting solid (38.1 g; yield: 77%).

Step 3

A solution of (S)-2-(tert-butoxycarbonyl)amino-butyraldehyde (30 g, 160 mmol) in toluene (150 mL) was added over 30 min. at −5° C. to a solution of Grignard reagent of benzoxazole (prepared as described in Step 1 above). The reaction mixture was stirred for 0.5 h at 0° C., then 2.5 h at RT. Quenching with 5% aq. acetic acid, washings with 5% aq. sodium carbonate, then brine and concentration to dryness gave crude (S)-2-(tert-butoxycarbonyl)-amino-1-benzoxazol-2-yl-butan-1-ol. The residue was diluted with toluene, and silica gel was added. The slurry was filtered. Elution by toluene removed the non-polar impurities. Then an 8/2 mixture of toluene and ethyl acetate desorbed the (S)-2-(tert-butoxycarbonyl) amino-1-benzoxazol-2-ylbutan-1-ol.

Step 4

To a solution of (S)-2-(tert-butoxycarbonyl)amino-1-benzoxazol-2-yl-propan-1-ol (26.3 g, 86 mmol) in isopropanol (118 mL) at 20–25° C. was added trimethylchlorosilane (1.4 eq). The solution was stirred for 5 h at 50° C. Concentration of the reaction mixture to 52 mL followed by addition of isopropyl ether (210 mL), filtration and drying under vacuum afforded (S)-2-amino-1-benzoxazol-2-ylbutan-1-ol hydrochloride salt as a grey solid (16.4 g; yield=79%; mixture of diastereomers).

Reference V

Synthesis of thiophene-2-carbothioic acid(2,2,2-trifluoroethyl)amide

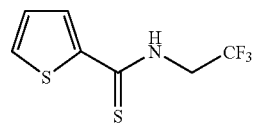

Step 1

Thiophene-2-carboxylic acid was coupled to trifluoroethyl amine using HBTU utilizing a procedure described in Example 1, Step 2 below except substituting HOBt with HBTU to give thiophene-2-carboxylic acid (2,2,2-trifluoroethyl)amide.

Step 2

To thiophene-2-carboxylic acid(2,2,2-trifluoroethyl)amide (2.8 g, 13.28 mmol, 1.0 equiv.) in toluene (100 mL) was added Lawesson's reagent (2.71 g, 6.69 mmol, 0.5 equiv.) The solution was stirred at 100° C. for 3 h. The solvent was removed in vacuo and the resulting residue was purified by flash chromatography (5% EtOAc/hexanes as eluent) to afford the title compound (1.4 g) as a yellow solid. MS=225.9 (M+1).

Proceeding as described above, but substituting thiophene-2-carboxylic acid with commercially available starting materials, the following compounds were prepared:

Phenyl-2-carbothioic acid (2,2,2-trifluoroethyl)amide; MS=220 (M+1)

4-Fluorophenylcarbothioic acid (2,2,2-trifluoroethyl)amide; MS=238 (M+1)

Pyridine-4-carbothioic acid (2,2,2-trifluoroethyl)amide; MS=222 (M+1)

Furan-2-carbothioic acid (2,2,2-trifluoroethyl)amide; MS=210 (M+1)

Thiophene-3-carbothioic acid (2,2,2-trifluoroethyl)amide; MS=226 (M+1)

Furan-3-carbothioic acid (2,2,2-trifluoroethyl)amide; MS=210 (M+1)

2,2,2-Trifluorothioacetamide; MS=127.9 (M−1)

N-Methyl-2,2-2-trifluorothioacetamide; MS=141.8 (M−1)

N-(2,2,2-trifluoroethyl)-2,2,2-trifluorothioacetamide; MS=208.8 (M−1)

N-Thiazol-2-yl-2,2,2-trifluorothioacetamide; MS=210.8 (M−1)

Tetrahydropyran-4-carbothioic acid (2,2,2-trifluoroethyl)-amide; MS=225.8 (M−1); and N-Thiazol-2-yl-thioisonicotinamide; MS=220 (M−1).

Reference W

Synthesis of 1,1-dioxo-1,2-dihydro-1λ$^6$-thieno[2,3-d]isothiazol-3-one

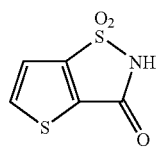

Step 1

Methyl 4-(chlorosulfonyl)thiophene-3-carboxylate (5 g, 20.75 mmol) was dissolved in methylene chloride (50 mL), the solution was cooled to 0° C., and ammonia gas (1.1 g, 64.7 mmol) was introduced during 20 min. After a further 2 h of stirring, the reaction mixture was washed to neutrality with 10% aqueous hydrochloric acid and then with brine. After concentration os the solvent, crude methyl 4-sulfamoylthiophene-3-carboxylate was obtained which was recrystallized from ethanol to yield 2.7 g of methyl 4-sulfamoylthiophene-3-carboxylate. MS: 220 (M−1), 221.9 (M+1), 243.8 (M+Na).

Step 2

A mixture of methyl 4-sulfamoylthiophene-3-carboxylate (2.7 g, 12.2 mmol), methanol (12 mL), and a 25% methanolic solution of sodium methylate (3.6 mL) was refluxed for 48 h. The reaction mixture was cooled to room temperature and acidified with concentrated hydrochloride acid, and the precipitated product was collected and washed with water. Recrystallized from water, yielded 400 mg of the title compound. MS: 187.8 (M−1), 189.5 (M+1). $^1$H NMR (DMSO-d$_6$): 8.34 (d, J=4.4 Hz, 1H), 7.705 (d, J=4.8 Hz, 1H).

Reference X

Synthesis of 2(S)-amino-N-[1 (S)-(benzoxazol-2-ylhydroxymethyl)propyl]-3-(1-methylcyclopentyl) propionamide

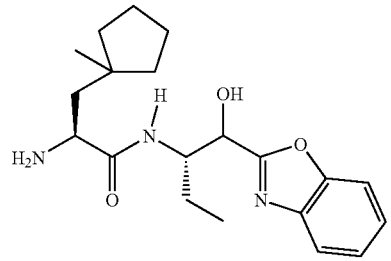

Step 1

1-Methylcyclopentanol (20 g, 0.2 mol) was added to hydrobromic acid (40 mL) at room temperature. After stirring for 1 h, the solution was extracted with hexane and the hexane was washed with brine and dried with magnesium sulfate. After concentration of the organic layer, 20.5 g of 1-methylcyclopentylbromide was obtained.

Step 2

Tributyltin hydride (37.8 g, 130 mmol) was added at reflux to a 500 ml of flask charged with benzene (200 mL) was added Z-dehydro-Ala-OH (15 g, 64 mmol), 1-methylcyclopentanylbromide (20.5 g) and AIBN (1.9 g). After 2 h, the solvent was removed and the residue was purified by column chromatograph to yield 7.9 g of 2-benzyloxycarbonylamino-3-(1-methylcyclopentyl)propionic acid methyl ester.

Step 3

2-Benzyloxycarbonylamino-3-(1-methylcyclopentyl)-propionic acid methyl ester (7.6 g, 23.8 mmol) was dissolved in a mixture of acetonitrile (82 mL) and 0.2 M aqueous NaHCO$_3$ (158 mL) and Alcalase 2.4 L (1.1 mL) was added and the reaction mixture wa stirred vigorously for 8 h. The reaction mixture was then evaporated at 30° C. to remove acetonitrile, and the aqueous residue was washed with ether. The ethereal layer was concentrated to yield 1.9 g of (R)-2-benzyloxycarbonylamino-3-(1-methylcyclopentyl)-propionic acid methyl ester. The aqueous phase was filtered with Celite, the pH was adjusted to 3 with 6 N HCl, and the solution was extracted with ethylacetate. The ethyl acetate layer was dried and evaporated to yield 1.4 g of (S)-2-benzyloxycarbonylamino-3-(1-methyl-cyclopentyl)-propionic acid. MS: 304.2 (M−1), 306.0 (M+1), 327.9 (M+Na).

$^1$HNMR (DMSO-d$_6$): 12.3 (COOH, br, 1H), 7.53(d, NH, 1H), 7.4–7.3 (m, 5H), 5.02 (s, 2H), 4.1–3.9 (m, 1H), 1.8–1.2 (m, 10H), 0.92 (s, 3H).

Step 4

To a stirred mixture of (S)-2-benzyloxycarbonylamino-3-(1-methylcyclopentyl)-propionic acid (560 mg, 1.84 mmol), 2-amino-1-benzoxazol-2-ylbutan-1-ol (378 mg, 1.84 mmol), and HOBt (338 mg, 2.2 mmol) in MeCl$_2$ (10 mL) were added EDC (533 mg, 2.76 mmol) and N-methylmorpholine (373 mg) at room temperature. After stirring for 14 h, the reaction mixture was extracted with ethyl acetate. The organic layer was washed with saturated NaHCO$_3$, brine, dried with MgSO$_4$ and concentrated. Purification with column chromatograph yielded 600 mg of [1-[1 (S)-(benzoxazol-2-ylhydroxymethyl)propyl-carbamoyl]-2(S)-(1-methylcyclopentyl)ethyl]-carbamic acid benzyl ester.

MS: 492.2(M−1), 494.4(M+1), 516.3(M+Na).

Step 5

Pd/C (5%) (60 mg) was added to a solution of of [1-[1-(benzoxazol-2-ylhydroxymethyl)propylcarbamoyl]-2-(1-methylcyclopentyl)ethyl]-carbamic acid benzyl ester (600 mg) in EtOH (30 mL) and the reaction mixture was stirred under hydrogen atmosphere (50 psi) for 2 h. The catalyst was removed by filtration and the filtrate was concentrated to yield 430 mg of the title compound. MS: 358.2 (M−1). 360.1 (M+1), 382.0(M+Na).

Example 1

Synthesis of (S)-N-[(S)-1-(benzoxazol-2-ylcarbonyl)-propyl]-3-cyclohexyl-2-(1,1-dioxobenzo[d]isothiazol-3-ylamino)propionamide

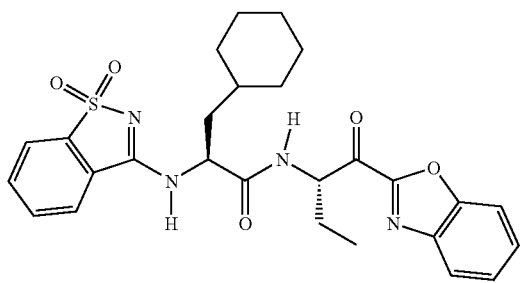

Step 1

L-Cyclohexylalanine hydrochloride (414 mg, 2 mmol) was dissolved in a mixture of 1N aq. NaOH solution (6 mL) and 1,4-dioxane (6 mL). 3-Chloro-benzo[d]isothiazole 1,1-dioxide (402 mg, 2 mmol), prepared as described in Davis, F. A. et al. *J. Org. Chem.* 1990, 55, 1254–1261, was added and the reaction mixture was stirred at room temperature for 30 min. The reaction mixture was acidified with 1N aq. HCl and extracted with ethyl acetate. The combined organic layers were washed with brine, dried with MgSO$_4$ and evaporated under vacuum. The crude (S)-3-cyclohexyl-2-(1,1-dioxo-benzo[d]isothiazol-3-ylamino)-propionic acid (620 mg, 1.84 mmol) was used without further purification.

Step 2

(S)-3-Cyclohexyl-2-(1,1-dioxo-benzo[d]isothiazol-3-ylamino)-propionic acid (150 mg, 0.45 mmol) was combined with EDC (250 mg, 1.3 mmol), HOBt (250 mg, 1.6 mmol), and (2S)-2-amino-1-benzoxazol-2-ylbutan-1-ol (250 mg, 1.2 mmol). Dichloromethane (4 mL) was added and then 4-methylmorpholine (0.5 mL). The reaction mixture was stirred at ambient temperature for 2 h. After dilution with ethyl acetate (150 mL), the solution was washed with 1N aqueous HCl, water, saturated aqueous NaHCO$_3$ solution and brine, dried with MgSO$_4$ and evaporated under vacuum. The crude product was dissolved in dry dichloromethane (10 mL) and Dess-Martin Periodinane (500 mg, 1.2 mmol) was added. After stirring at ambient temperature for 1 h, the reaction mixture was diluted with ethyl acetate (150 mL) and treated with 0.26M Na$_2$S$_2$O$_3$ solution in saturated aqueous NaHCO$_3$. The organic phase was washed with saturated aqueous NaHCO$_3$ and brine, dried with MgSO$_4$ and evaporated. The product was purified by flash chromatography on silica gel (hexane/ethyl acetate 2:1) to yield the title compound (120 mg).

$^1$H NMR: (DMSO) δ 9.43 (d, J=7.6 Hz, 1H), 8.94 (d, J=6.0 Hz, 1H), 8.33–8.29 (m, 1H), 7.97–7.93 (m, 2H), 7.86 (d, J=8.0 Hz, 1H), 7.82–7.77 (m, 2H), 7.60 (t, J=8.0 Hz, 1H), 7.49 (t, J=8.0 Hz, 1H), 5.22–5.16 (m, 1H), 4.75–4.68 (m, 1H), 2.08–1.96 (m, 1H), 1.81–0.83 (m, 14H), 1.00 (t, J=7.6 Hz, 3H). MS: (M+H)$^+$ 523.

Following the procedure as described above but substituting L-cyclohexylalanine hydrochloride with L-leucine gave 2-(1,1-dioxobenzo[d]isothiazol-3-ylamino)-4-methyl-pentanoic acid [1-(benzoxazol-2-ylcarbonyl)propyl]amide.

$^1$H NMR: (DMSO) δ 8.56 (d, J=6.4 Hz, 1H), 8.41 (d, J=8.8 Hz, 1H), 8.03–7.93 (m, 3H), 7.87–7.74 (m, 3H), 7.61 (t, J=8.0 Hz, 1H), 7.51 (t, J=8.0 Hz, 1H), 4.86–4.79 (m, 1H), 3.98–3.90 (m, 1H), 1.90–1.79 (m, 1H), 1.67–1.52 (m, 2H), 1.42–1.25 (m, 2H), 0.86–0.79 (m, 6H), 0.74 (d, J=6.4 Hz, 3H). MS: (M+H)$^+$ 483.

Example 2

Synthesis of (S)-4-methyl-2-(3-oxo-3H-isoindol-1-ylamino)-pentanoic acid(S)-[1-(benzoxazol-2-ylcarbonyl)propyl]amide

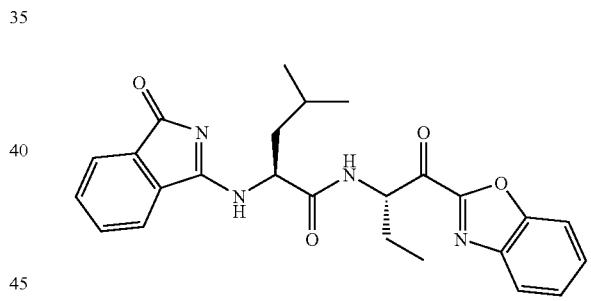

Step 1

Boc-Leu-OH (350 mg, 1.40 mmol) was combined with EDC (500 mg, 2.6 mmol), HOBt (250 mg, 1.6 mmol), and (2S)-2-amino-1-benzoxazol-2-yl-butan-1-ol hydrochloride (300 mg, 1.24 mmol). Dichloromethane (10 mL) was added and then 4-methylmorpholine (1 mL). The reaction mixture was stirred at ambient temperature for 2 h. After dilution with ethyl acetate (150 mL), the solution was washed with 1N aqueous HCl, water, saturated aqueous NaHCO$_3$ solution and brine, dried with MgSO$_4$ and evaporated under vacuum. The crude product was dissolved in 4N HCl/dioxane solution and stirred for 2 h. Evaporation to dryness gave (S)-2-amino-4-methyl-pentanoic acid(S)-[1-(benzoxazol-2-yl-hydroxy-methyl)-propyl]-amide hydrochloride (450 mg) as brownish oil.

Step 2

(S)-[1-(Benzoxazol-2-yl-hydroxy-methyl)-propyl]-amide hydrochloride (90 mg, 0.254 mmol), 3-iminoisoindolinone (100 mg, 0.684 mmol), and N,N-diisopropylethyl-amine (0.2 mL) were dissolved in THF (10 mL) and heated at reflux for 5 h. After dilution with ethyl acetate (150 mL), the solution was washed with saturated aqueous NaHCO₃ solution and brine, dried with MgSO₄ and evaporated under vacuum. The crude product was dissolved in dry dichloromethane (10 mL) and Dess-Martin Periodinane (400 mg, 0.96 mmol) was added. After stirring at ambient temperature for 1 h, the reaction mixture was diluted with ethyl acetate (150 mL) and treated with 0.26 M Na₂S₂O₃ solution in saturated aqueous NaHCO₃. The organic phase was washed with saturated aqueous NaHCO₃ and brine, dried with MgSO₄ and evaporated. The product was purified by flash chromatography on silica gel (hexane/ethyl acetate 2:1) to yield the title compound (20 mg; 0.045 mmol) as a 1:1 mixture of isomers.

¹H NMR: (DMSO) δ 11.03/11.01 (s, 1H), 8.19/8.14 (d, J=7.2 Hz, 1H), 7.94–7.45 (m, 8H), 5.20–5.14 (m, 1H), 4.35–4.30 (m, 1H), 2.08–1.96 (m, 1H), 1.86–1.40 (m, 4H), 1.00–0.78 (m, 9H). MS: (M+H)⁺ 447.

Example 3

Synthesis of ({1 (S)-[1 (S)-(benzoxazol-2-ylcarbonyl)propylcarbamoyl]-3-methylbutylamino}-morpholin-4-ylmethylene)carbamic acid ethyl ester

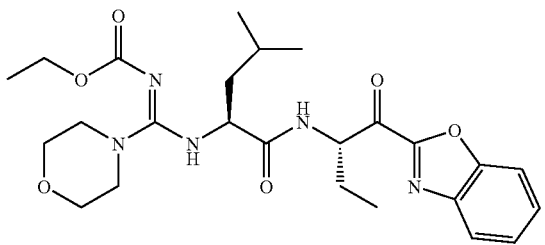

Step 1

Ethyl isothiocyanatoformate (5 g, 38.2 mmol) was dissolved in THF (50 mL) and cooled to 0° C. Morpholine (3.99 mL, 45.8 mmol) was added dropwise over 2 min. The reaction mixture was stirred for 3 h. The solvent was evaporated to give (morpholin-4-yl-carbothioyl)carbamic acid ethyl ester (8.3 g, 38 mmol) as a white solid.

Step 2

(Morpholine-4-carbothioyl)carbamic acid ethyl ester (55 mg, 0.25 mmol), 2-amino-4-methylpentanoic acid [1-(benzoxazol-2-ylhydroxymethyl)propyl]amide hydrochloride (90 mg, 0.25 mmol), and diisopropylethylamine (0.13 mL, 0.76 mmol) were dissolved in dichloromethane (5 mL). 2-Chloro-1-methylpyridinium iodide (84 mg, 0.33 mmol) was added and the reaction mixture was stirred at ambient temperature over night. After dilution with ethyl acetate (100 mL), the solution was washed with sat. aq. NaHCO₃, and brine, dried with MgSO₄ and evaporated under vacuum. The residue was dissolved in dichloromethane (10 mL) and Dess-Martin periodinane (400 mg) was added. The reaction mixture was stirred at ambient temperature for 1 h. After dilution with ethyl acetate (100 mL), the solution was washed with a 0.26 M solution of Na₂S₂O₃ in sat. aqu. NaHCO₃, then with sat. aq. NaHCO₃, and brine, dried with MgSO₄ and evaporated under vacuum. After purification by flash chromatography on silica gel, the title compound was obtained as yellowish glass (10 mg, 0.020 mmol). MS: (M+H)⁺ 502.

Proceeding as described in Example 5 above, but substituting (morpholin-4-yl-carbothioyl)carbamic acid ethyl ester with morpholine-4-carbothioic acid (2,2,2-trifluoroethyl)amide and 2-amino-4-methylpentanoic acid [1-(benzoxazol-2-ylhydroxymethyl)propyl]amide hydrochloride with 2-amino-3-cyclohexylpropionic acid [1-(benzoxazol-2-ylhydroxymethyl)propyl]amide hydrochloride (prepared by reacting L-cyclohexyalanine with 2RS-amino-1-benzoxazol-2-yl-1-butanol as described in Example 1, step 2 above) provided N-[1-(benzoxazol-2-yl-hydroxy-methyl)-propyl]-3-cyclohexyl-2-{[N-(2,2,2-trifluoroethyl)-morpholine-4-carboximidoyl]-amino}-propionamide, Mol. Wt.: 553.62. MS: 552.5 (M–1), 554.7 (M+1).

Example 4

Synthesis of N-[1-(benzoxazol-2-ylcarbonyl)-propyl]-3-phenylmethanesulfonyl-2(R)-{[N-(2,2,2-trifluoroethyl)-morpholin-4-ylcarboximidoyl]amino}propionamide

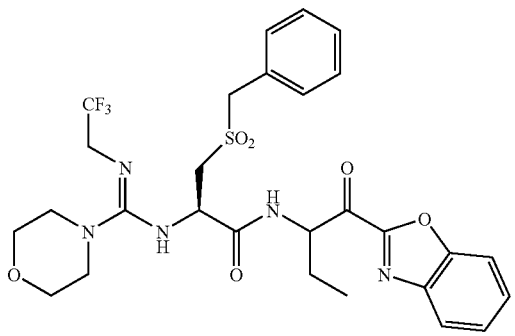

Step 1

To a solution of N-tert-butoxycarbonyl-S-benzylcysteine (7.75 g, 28 mmol, 1.0 equiv.) (prepared by reacting S-benzylcysteine with boc anhydride via a standard protocol) in methanol (250 mL) was added, with stirring, Oxone (19 g, 31 mmol, 1.1 equiv.) in H₂O (100 mL). The resulting suspension was stirred for 2 h at ambient temperature after which methanol was removed in vacuo. The aqueous layer was extracted with ethyl acetate to give 2-N-tert-butoxycarbonyl-3-phenylmethanesulfonylpropionic acid (7.85 g, 25.5 mmol) which was converted to {1-[1-(benzoxazol-2-ylhydroxymethyl)-propylcarbamoyl]-2-phenylmethanesulfonylethyl)-carbamic acid tert-butyl ester as described in Example 1, Step 2 above.

Step 2

1,1'-Thiocarbonyldiimidazole (0.980 g, 5.50 mmol, 1.2 equiv.) was dissolved in CH₂Cl₂ (200 mL), followed by addition of diisopropylethylamine (3.2 mL), and trifluoroethylamine hydrochloride (0.620 g, 4.58 mmol, 1.0 equiv.). The solution was stirred for 1 h at ambient temp, then 2-amino-N-[1-(benzoxazol-2-ylhydroxymethyl)-propyl]-3-phenylmethanesulfonylpropionamide was added in one portion. After stirring overnight, the reaction mixture was diluted with EtOAc (150 mL), washed with saturated bicarb, brine, dried over MgSO₄. Purification with flash chromatography (50% ETOAc/hexanes as eluent) afforded N-[1-(benzoxazol-2-ylhydroxymethyl)-propyl]-3-phenyl-methanesulfonyl-2-[3-(2,2,2-trifluoroethyl)thioureido]propionamide (0.720 g) as a mixture of diasteomers.

Step 3

Copper Sulfate-5H₂O (0.75 g) was added to flash silica gel (2.25 g) and the mixture placed in an oven and heated at 240° C. for 2 h, then cooled in a dessicator. In a dry microwave tube was placed THF (4 mL), N-[1-(benzoxazol-2-ylhydroxymethyl)-propyl]-3-phenylmethanesulfonyl-2-[3-(2,2,2-trifluoroethyl)thioureido]propionamide (0.20 g, 0.350 mmol, 1.0 equiv), morpholine (0.122 g, 1.40 mmol, 4.0 equiv), CuSO$_4$/SiO$_2$ (0.525 g, 1.5 equiv.), and Et$_3$N (0.035 g, 1.0 equiv.). The mixture was heated via microwave to 80° C. for 30 min. The suspension was filtered and the solid washed with 10% MeOH/CH$_2$Cl$_2$. The filtrate was concentrated and the resulting residue was purified by reverse phase chromatography to afford N-[1-(benzoxazol-2-yl-hydroxymethyl)-propyl]-3-phenylmethanesulfonyl-2-{[N-(2,2,2-trifluoroethyl)-morpholin-4-ylcarboximidoyl]-amino}propionamide (0.090 g) as a mixture of diastereomers.

Step 4

To N-[1-(benzoxazol-2-yl-hydroxymethyl)-propyl]-3-phenylmethanesulfonyl-2-{[N-(2,2,2-trifluoroethyl)-morpholin-4-ylcarboximidoyl]-amino}propionamide (40 mg, 0.064 mmol) in CH$_2$Cl$_2$ (0.5 mL) was added Dess-Martin Periodinane (110 mg, 0.256 mmol) and the solution stirred for 2 h at ambient temperature. The reaction mixture was quenched with 0.26 M Na$_2$S$_2$O$_4$ in sated NaHCO$_3$ and diluted with EtOAc. The organic layer was washed with water, brine, and dried over MgSO$_4$ and concentrated to give the title compound as a white solid. MS=624.5 (M+1).

Proceeding as described in Step 2 above, but substituting 2-amino-N-[1-(benzoxazol-2-ylhydroxymethyl)-propyl]-3-phenylmethanesulfonylpropionamide with morpholine, trifluoroethylamine, pyrrolidine, piperidine, 4-methylpiperidine, and 4-methylpiperazine, the following compounds were prepared.

Morpholine-4-carbothioic acid (2,2,2-trifluoroethyl) amide. Mol. Wt.: 228.24;

MS: 227.0 (M−1), 229.1 (M+1);

1,3-Bis-(2,2,2-trifluoroethyl)thiourea; MS: 239.5 (M−1), 240.9 (M+1);

Pyrrolidine-1-carbothioic acid (2,2,2-trifluoroethyl) amide; MS: 210.8 (M−1), 212.9 (M+1);

(2,2,2-Trifluoro-ethyl)-thiourea; MS: 156.8 (M−1), 158.7 (M+1);

Piperidine-1-carbothioic acid (2,2,2-trifluoroethyl)amide; MS: 225.1 (M−1), 227.0 (M+1);

4-Methyl-piperazine-1-carbothioic acid (2,2,2-trifluoroethyl)amide; MS: 239.9 (M−1), 242.2 (M+1); and 1,1-Dimethyl-3-(2,2,2-trifluoroethyl)thiourea; MS: 184.8 (M−1), 186.9 (M+1), respectively.

Example 5

Synthesis of N-[1-(benzoxazol-2-ylcarbonyl)propyl]-3-cyclohexyl-2(S)-[N-(2,2,2-trifluoroethyl) formimidoylamino]propionamide

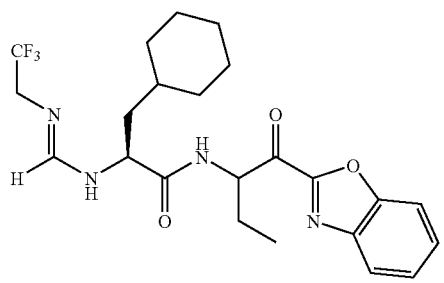

Step 1

To a solution of 100 uL of N-[1-(benzoxazol-2-ylhydroxymethyl)propyl]-3-cyclohexyl-2-[3-(2,2,2-trifluoroethyl)thioureido]propionamide (60 mg, 0.12 mmol) (prepared by reacting cyclohexylalanine with 2-(RS)-amino-1-benzoxazol-2-ylbutan-1-ol to give 2-amino-3-cyclohexylpropionic acid [1-(benzoxazol-2-ylhydroxymethyl)propyl]-amide hydrochloride which was then reacted with 1,1'-thiocarbonyldiimidazole and trifluoroethylamine as described Example 4, Step 2 above) was added 30% aqueous hydrogen peroxide solution (28 uL, 0.25 mmol) dropwise at room temperature. Conversion to product was observed by analytical HPLC in 30 min. Water (1 mL) was added, and the mixture was stored at 0° C. for 48 h. After thawing, the aqueous supernatant was decanted and the solid was further dried under reduced pressure to give N-[1-(benzoxazol-2-yl-hydroxymethyl)-propyl]-3-cyclohexyl-2-[N-(2,2,2-trifluoroethyl)-formimidoylamino]-propionamide (28 mg) which was then converted to the title compound using Dess-Martin Periodinane as described previously. MS: 467.4 (M+1); 465.1 (M−1).

Example 6

Synthesis of N-[1-(benzoxazol-2-ylcarbonyl)propyl]-3-cyclohexyl-2(S)-[(methanesulfonyliminophenylmethyl)amino]propionamide

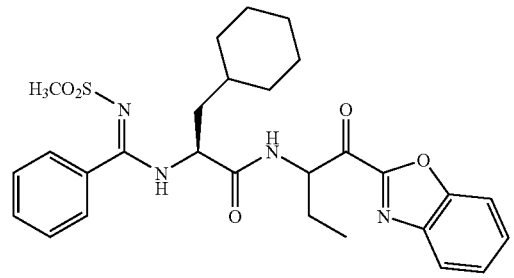

Step 1

A mixture of methanesulfonamide (4.75 g, 50 mmol)) and trimethyl orthobenzoate (18.2 g, 100 mmol) was heated at 120° C. for 4 h in the presence of a catalytic amount of p-toluenesulfonic acid (50 mg). After being cooled to room temperature, the reaction mixture was diluted with ethyl acetate (100 mL) and washed with a saturated sodium bicarbonate aqueous solution and then water. The organic phase was dried over MgSO$_4$, concentrated, and the resulting residue was treated with hexanes (100 mL) with stirring overnight. A white solid formed was filtered and washed with hexanes to yield a pure N-(methoxyphenylmethylene)methansulfonamide.

Step 2

To a mixture of N-(methoxy-phenyl-methylene)methansulfonamide (250 mg, 0.616 mmol) and 2-amino-3-cyclohexylpropionic acid [1-(benzoxazol-2-ylhydroxymethyl)-propyl]amide (255 mg, 0.616 mmol) in dry acetonitile (4 mL) at room temperature was added DBU (0.37 mL, 2.46 mmol), and the mixture was stirred at the same temperature overnight. After a removal of the solvent, the reaction mixture was partitioned between ethyl acetate and 1N-HCl solution, washed brine and then water. The organic extracts were dried, concentrated in vacuo, and purified by flash chromatography on silica gel (eluted with EtOAc/hexanes=3/1) to yield 250 mg of N-[1-(benzoxazol-2-yl-hydroxymethyl)propyl]-3-cyclohexyl-2-[(methanesulfonyliminophenylmethyl)amino]-propionamide.

Step 3

To a stirred solution of N-[1-(benzoxazol-2-yl-hydroxymethyl)propyl]-3-cyclohexyl-2-[(methanesulfonyliminophenylmethyl)amino]propionamide (250 mg, 0.463 mmol) in dry THF (10 mL) was added at room temperature Dess-Martin periodinane (265 mg, 0.626 mmol), and the mixture was stirred at the same temperature for 1 h. A 25% sodium thiosulfate solution (3 mL) and saturated sodium bicarbonate solution (3 mL) were added. The biphasic mixture was stirred for additional 30 min, diluted with ethyl acetate (30 mL), and washed with brine and then water. The organic extracts were were dried, concentrated in vacuo, and purified by flash chromatography on silica gel (eluted with 1:1 EtOAc/hexanes) to yield 188 mg (75%) of the title compound as a mixture of E/Z isomers in ca. 3.5:1 ratio. $^1$H NMR for a major isomer (400 MHz, CDCl$_3$): δ 7.97–7.40 (9H, m), 6.96(1H, d, J=8.0 Hz), 6.11(1H, d, J=7.6 Hz), 5.71(1H, m), 4.81(1H, m), 3.07(s, 3H), 2.35–0.80(m, 15H), 1.13(3H, t, J=7.2 Hz). MS: 539.3(MH$^+$).

Example 7

Synthesis of N-[1-(benzoxazol-2-ylcarbonyl)propyl]-2(R)-(1-cyclopentylamino-2-methanesulfonylvinylamino)-3-cyclopropylmethanesulfonyl-propionamide

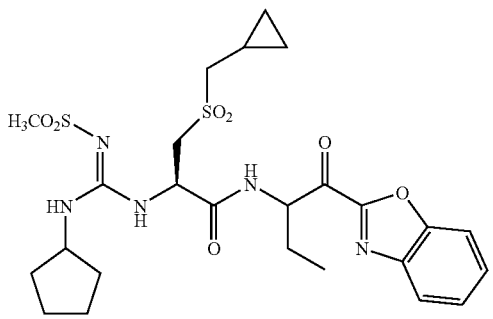

Step 1

To methylsulfonyl isothiocyanate (175 mg, 0.128 mmol, 1.0 equiv.) (prepared according to a literature procedure (*J. Org. Chem.* 1967, p 340) in benzene (1 mL) was added cyclopentyl amine (130 mg, 1.53 mmol 1.2 equiv.) and the mixture was heated to 80° C. in a microwave instrument. Upon cooling, 1-cyclopentyl-3-methylsulfonylthiourea precipitated as brown needles and was filtered (210 mg).

Step 2

To 1-cyclopentyl-3-methylsulfonylthiourea (200 mg, 0.89 mmol, 2.4 equiv.), 2-amino-N-[1-(benzoxazol-2-ylhydroxymethyl)-propyl]-3-cyclopropylmethanesulfonyl-propionamide (163 mg, 1.0 equiv.), N-methyl-2-chloropyridinium iodide (175 mg, 1.8 equiv.) in 4 mL dichloromethane was added DIPEA (142 mg, 2.8 equiv). The reaction mixture was stirred overnight at ambient temp. The reaction was diluted with ethyl acetate and extracted with saturated sodium bicarbonate, brine and dried over MgSO$_4$. Purification by column chromatography (EtOAC/hexanes) afforded N-[1-(benzoxazol-2-ylhydroxymethyl)propyl]-2-(1-cyclopentylamino-2-methanesulfonylvinylamino)-3-cyclopropyl-metanesulfonylpropionamide as a mixture of diastereomers (41 mg, M=584.3 M+1) which was oxidized to the title compound using Dess-Martin Periodane as previously described.

Example 9

Synthesis of N-[1-(benzoxazol-2-ylcarbonyl)-propyl]-3-cyclohexyl-2(S)-[(morpholin-4-ylcarboximidoyl)amino]propionamide

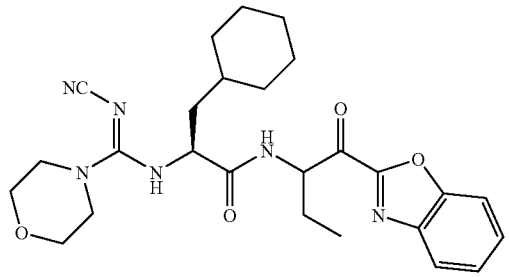

A solution of diphenyl cyanocarbonimidate (238 mg, 1.0 mmol), 2-amino-N-[1-(benzoxazol-2-ylhydroxymethyl)propyl]-3-cyclohexylpropionamide hydrochloride (495 mg, 1.0 mmol) and diisopropylethylamine (150 uL, 1.0 mmol) in isopropanol (3 mL) was stirred at room temperature for 18 h. Morpholine (1.65 mL, 20 mmol) was added and the reaction mixture was stirred for another 2 h. The solution was concentrated under reduced pressure, then partitioned between ethyl acetate and 1N HCl. The organic phase was washed with 1N HCl, then with brine, then dried over MgSO$_4$ and concentrated. The crude product was purified by silica gel chromatography (ethyl acetate) to give 93 mg of N-[1-(benzoxazol-2-yl-hydroxymethyl)propyl]-3-cyclohexyl-2-[(morpholin-4-yl-carboximidoyl)amino]propionamide which was then converted to the title compound using Dess-Martin Periodinane under the reaction conditions described above. MS: 497.4 (M+1); 495.4 (M–1).

Example 10

Synthesis of N-[1 (S)-(benzoxazol-2-ylhydroxymethyl)propyl]-3-cyclohexyl-2(S)-[(methanesulfonyliminomethyl)amino]propionamide

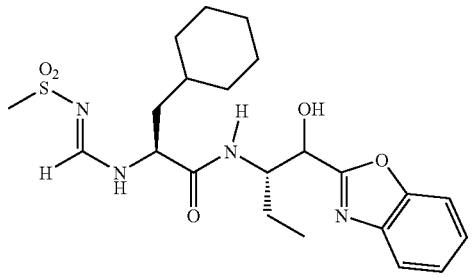

Step 1

A mixture of cyclohexylalanine methyl ester hydrochloride (1.33 g, 6 mmol) in acetonitrile (25 mL) was cooled to 0° C. was treated with N-methylmorpholine (0.66 mL). A solution of ethyl methanesulfonyl formimidate (1.06 g, 5 mmol) (prepared by the procedure described in Anglada, L., *Arzneim. Forsch.* 1997, 47, 431–434) in acetonitrile (2 mL) was added to the reaction mixture. After stirring for 1 hour and 40 minutes at room temperature, the acetonitrile was removed by rotary evaporation and the resulting residue was diluted with ice water. The product was extracted with ethyl acetate and the extracts were dried and evaporated at reduced pressure to give 3-cyclohexyl-2-(1-methanesulfonyliminoethylamino)propionic acid methyl ester (1.213 g).

Step 2

A solution of 3-cyclohexyl-2-(i-methanesulfonyliminoethylamino)propionic acid methyl ester (1.213 g) in methanol (70 mL) and water (30 mL) was cooled in an ice bath and then treated with aqueous potassium hydroxide (0.989 M, 10 mL). The reaction mixture was stored at 5° C. overnight. The pH of the reaction mixture was adjusted to 5.5 with 1N hydrochloric acid and a white precipitate was removed by filtration. The methanol was removed from the filtrate by rotary evaporation at room temperature. Water (20 mL) was added to the residue and the product was extracted with methylene chloride to give after drying and evaporation 3-cyclohexyl-2-(1-methanesulfonyliminoethylamino)-propionic acid (0.410 g).

Step 3

A mixture of ethyldimethylaminopropyl carbodiimide hydrochloride (0.198 g, 1.14 mmol), hydroybenzotriazole (0.114 g, 0.742 mmol), 3-cyclohexyl-2-(1-methanesulfonyliminoethylamino)-propionic acid (0.205 g, 0.742 mmol) and 2(S)-amino-1-benzoxazol-2-ylbutan-1-ol (0.153 g, 0.743 mmol) in methylene chloride (6 mL) was cooled in an ice bath and then N-methylmorpholine (0.155 g, 1.55 mmol) was added to the reaction mixture which was then stirred at room temperature for 40 min. The reaction mixture was diluted with ice water and dilute hydrochloric acid and the product extracted with ethyl acetate. The extracts were washed with aqueous sodium bicarbonate, then brine, then dried over magnesium sulfate and evaporated to give of N-[1(S)-(benzoxazol-2-ylhydroxymethyl)propyl]-3-cyclohexyl-2-[(methanesulfonyliminomethyl)-amino]propionamide (0.314 g). Exact mass 464.21. Found: M+H=465.3, M+Na=487.3, M−H=463.1.

N-[1(S)-(benzoxazol-2-ylhydroxymethyl)propyl]-3-cyclohexyl-2-(1-methanesulfonyliminoethylamino)-propionamide can be converted to N-[1 (S)-(benzoxazol-2-ylcarbonyl)-propyl]-3-cyclohexyl-2-(1-methanesulfonyliminoethylamino)-propionamide using Dess-Martin Periodinane as described above.

Example 12

Synthesis of ({1-[1 (S)-(benzoxazol-2-ylcarbonyl)-propylcarbamoyl]-2(R)-phenylmethanesulfonylethylamino}phenylmethylene)carbamic acid ethyl ester

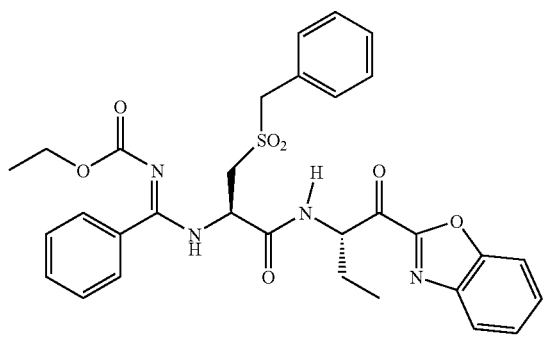

Thiobenzoyl-carbamic acid ethyl ester (1.209 mg, 1 mmol), 2-amino-N-[1(S)-(benzoxazol-2-yl-hydroxymethyl)-propyl]-3(R)-phenylmethanesulfonyl-propionamide hydrochloride (467 mg, 1 mmol), 2-chloro-1-methyl-pyridinium iodide (306 mg, 1.2 mmol) and DIPEA (0.52 mL, 3 mmol) were added to $CH_2Cl_2$ (10 mL) and the reaction mixture was stirred at room temperature overnight. Solvent was removed under reduced pressure and the crude product was oxidized with Dess-Martin Periodinane (3.508 mg, 1.2 mmol) in 10 mL $CH_2Cl_2$. LC-MS: 605 (M+1), 603 (M−1), 627(M+23)

BIOLOGICAL EXAMPLES

Example 1

Cathepsin B Assay

Solutions of test compounds in varying concentrations were prepared in 10 μL of dimethyl sulfoxide (DMSO) and then diluted into assay buffer (40 μL, comprising: N,N-bis (2-hydroxyethyl)-2-aminoethanesulfonic acid (BES), 50 mM (pH 6); polyoxyethylene-sorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at room temperature. Z-FR-AMC (20 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

Compounds of the invention were tested by the above-described assay and observed to exhibit cathepsin B inhibitory activity.

Example 2

Cathepsin K Assay

Solutions of test compounds in varying concentrations were prepared in 10 μL of dimethyl sulfoxide (DMSO) and then diluted into assay buffer (40 mL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at room temperature. Z-Phe-Arg-AMC (4 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

Compounds of the invention were tested by the above-described assay and observed to exhibit cathepsin K inhibitory activity.

Example 3

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at room temperature. Z-Phe-Arg-AMC (1 nMoles in 25 μL of assay buffer) was added to the assay solutions and hydrolysis was followed spectrophotometrically at (λ460 nm) for 5 minutes. Apparent inhibition constants (K_i) were calculated from the enzyme progress curves using standard mathematical models.

Compounds of the invention were tested by the above-described assay and observed to exhibit cathepsin L inhibitory activity.

Example 4

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); β-mercaptoethanol, 2.5 mM; and BSA, 0.00%. Human cathepsin S (0.05 pMoles in 25 μL of assay buffer) was added to the dilutions. The assay solutions were mixed for 5–10 seconds on a shaker plate, covered and incubated for 30 minutes at room temperature. Z-Val-Val-Arg-AMC (4 nMoles in 25 μL of assay buffer containing 10% DMSO) was added to the assay solutions and hydrolysis was followed spectrophotometrically (at λ460 nm) for 5 minutes. Apparent inhibition constants (K_i) were calculated from the enzyme progress curves using standard mathematical models.

Compounds of the invention were tested by the above-described assay and observed to exhibit cathepsin S inhibitory activity.

Example 5

Cathepsin F Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); DTT, 2.5 mM; and BSA, 0.01%. Human cathepsin F (0.1 pMoles in 25 μL of assay buffer) was added to the dilutions. The assay solutions were mixed for 5–10 seconds on a shaker plate, covered and incubated for 30 minutes at room temperature. Z-Phe-Arg-AMC (2 nMoles in 25 μL of assay buffer containing 10% DMSO) was added to the assay solutions and hydrolysis was followed spectrophotometrically (at λ460 nm) for 5 minutes. Apparent inhibition constants (K_i) were calculated from the enzyme progress curves using standard mathematical models.

Compounds of the invention were tested by the above-described assay and observed to exhibit cathepsin F inhibitory activity.

Example 1

Representative Pharmaceutical Formulations Containing a Compound of Formula (Ia)/(Ib)

| ORAL FORMULATION | |
|---|---|
| Compound of Formula (Ia)/(Ib) | 10–100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of Formula (Ia)/(Ib) | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of Formula (Ia)/(Ib) | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

We claim:

1. A compound of Formula (Ia) or (Ib):

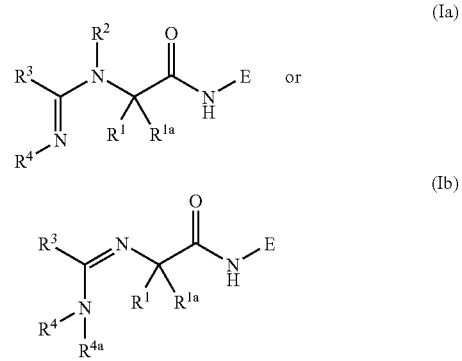

wherein:
E is:
(i) —C(R$^5$)(R$^6$)X$^1$ where X$^1$ is —CHO, —C(R$^7$)(R$^8$)CF$_3$, —C(R$^7$)(R$^8$)CF$_2$CF$_2$R$^9$, —C(R$^7$)(R$^8$)R$^{10}$, —CH=CHS(O)$_2$R$^{10}$, —C(R$^7$)(R$^8$)C(R$^7$)(R$^8$)OR$^{10}$, —C(R$^7$)(R$^8$)CH$_2$OR$^{10}$, —C(R$^7$)(R$^8$)C(R$^7$)(R$^8$)R$^{10}$, —C(R$^7$)(R$^8$)CH$_2$N(R$^{11}$)SO$_2$R$^{10}$, —C(R$^7$)(R$^8$)CF$_2$C(O)NR$^{10}$R$^{11}$, —C(R$^7$)(R$^8$)C(O)NR$^{10}$R$^{11}$, —C(R$^7$)(R$^8$)C(O)N(R$^{11}$), (CH$_2$)$_2$OR$^{11}$, or —C(R$^7$)(R$^8$)C(O)N(R$^{11}$)(CH$_2$)$_2$NHR$^{11}$;

where:
R$^5$ is hydrogen or (C$_{1-6}$)alkyl;
R$^6$ is hydrogen, (C$_{1-6}$)alkyl, cyano, —X$^2$NR$^{12}$R$^{12a}$, —X$^2$NR$^{12}$C(O)R$^{12a}$, —X$^2$NR$^{12}$C(O)OR$^{12a}$, —X$^2$NR$^{12}$C(O)NR$^{12a}$R$^{12b}$, —X$^2$NR$^{12}$C(N$^{12a}$)NR$^{12b}$R$^{12C}$, —X$^2$SR$^{13}$, X$^2$C(O)OR$^{12}$, —X$^2$C(O)R$^{13}$, —X$^2$OC(O)R$^{13}$, —X$^2$C(O)NR$^{12}$R$^{12a}$, —X$^2$S(O)$_2$NR$^{12}$R$^{12a}$, —X$^2$NR$^{12}$S(O)$_2$R$^{13}$, —X$^2$P(O)(OR$^{12}$)OR$^{12a}$, —X$^2$OP(O)(OR$^{12}$)OR$^{12a}$, —X$^2$S(O)R$^{14}$, —X$^2$S(O)$_2$R$^{14}$, R$^{15}$, —X$^2$OR$^{15}$, —X$^2$SR$^{15}$, —X$^2$S(O)R$^{15}$, —X$^2$S(O)$_2$R$^{15}$, —X$^2$C(O)R$^{15}$, —X$^2$C (O)OR$^{15}$, —X$^2$OC(O)R$^{15}$, —X$^2$NR$^{15}$R$^{12}$, —X$^2$NR$^{12}$C(O)R$^{15}$, —X$^2$NR$^{12}$C(O)OR$^{15}$, —X$^2$C(O)NR$^{15}$R$^{12}$, —X$^2$S(O)$_2$NR$^{15}$R$^{12}$, X$^2$NR$^{12}$S(O)$_2$R$^{15}$, —X$^2$NR$^{12}$C(O)NR$^{15}$R$^{12a}$ or —X$^2$NR$^{12}$C(NR$^{12a}$)NR$^{15}$R$^{12}$ where X$^2$ is (C$_{1-6}$)alkylene; R$^{12}$, R$^{12a}$, R$^{12b}$ and R$^{12c}$ at each occurrence independently is hydrogen or (C$_{1-6}$)alkyl; R$^{13}$ is hydrogen, (C$_{1-6}$)alkyl or halo-substituted(C$_{1-6}$alkyl, R$^{14}$ is (C$_{1-6}$)alkyl or halo-substituted(C$_{1-6}$)alkyl; and R$^{15}$ is (C$_{3-10}$)cycloalkyl(C$_{0-6}$)alkyl, hetero(C$_{3-10}$)cycloalkyl(C$_{0-3}$)alkyl, (C$_{6-10}$)aryl(C$_{0-6}$)alkyl, hetero(C$_{5-10}$)aryl(C$_{0-6}$)alkyl, (C$_{9-12}$)bicycloaryl(C$_{0-6}$) alkyl or hetero(C$_{8-12}$)bicycloaryl(C$_{0-6}$) alkyl; or R$^5$ and R$^6$ taken together with the carbon atom to which both R$^5$ and R$^6$ are attached form (C$_{3-8}$)cycloalkylene or hetero(C$_{3-8}$)cycloalkylene wherein said cycloalkylene and heterocycloalkylene may be substituted further with 1 to 2 radicals independently selected from (C$_{1-6}$) alkyl, cyano, halo, halo-substituted(C$_{1-4}$) alkyl, nitro, —X$^3$NR$^{16}$R$^{16a}$, X$^3$N$^{16}$C(O)R$^{16a}$, —X$^3$NR$^{16}$C(O)OR$^{16a}$, —X$^3$NR$^{16}$C(O)NR$^{16a}$R$^{16b}$, —X$^3$NR$^{16}$C(NR$^{16a}$)NR$^{16b}$R$^{16c}$, X$^3$OR$^{17}$, —X$^3$SR$^{17}$, —X$^3$C(O)OR$^{16}$, —X$^3$C(O)R$^{17}$, —X$^3$OC(O)R$^{17}$, —X$^3$C(O)NR$^{16}$R$^{16a}$, X$^3$S(O)$_2$NR$^{16}$R$^{16a}$, —X$^3$NR$^{16}$S(O)$_2$R$^{17}$, —X$^3$P(O)(OR$^{16}$)OR$^{16a}$, —X$^3$OP(O)(OR$^{16}$)OR$^{16a}$, X$^3$S(O)R$^{18}$ and —X$^3$S(O)$_2$R$^{18}$ where X$^3$ is a bond or (C$_{1-6}$) alkylene; R$^{16}$, R$^{16a}$, R$^{16b}$, and R$^{16c}$ at each occurrence independently is hydrogen or (C$_{1-6}$)alkyl; R$^{17}$ is hydrogen, (C$_{1-6}$)alkyl or halo-substituted(C$_{1-6}$)alkyl, and R$^{18}$ is (C$_{1-6}$) alkyl or halo-substituted(C$_{1-6}$)alkyl;

R$^7$ is hydrogen or (C$_{1-4}$)alkyl;

R$^8$ is hydroxy; or

R$^7$ and R$^8$ together form oxo;

R$^9$ is hydrogen, halo, (C$_{1-4}$)alkyl, (C$_{5-10}$)aryl(C$_{0-6}$)alkyl or hetero(C$_{5-10}$)aryl(C$_{0-6}$) alkyl; and R$^{10}$ is (C$_{1-4}$)alkyl, (C$_{6-10}$)aryl(C$_{0-6}$)alkyl, hetero(C$_{4-10}$)aryl(C$_{0-6}$)alkyl, (C$_{4-10}$)cycloalkyl(C$_{0-6}$)alkyl or hetero(C$_{4-10}$)cycloalkyl(C$_{0-6}$)alkyl; and R$^{11}$ is hydrogen or (C$_{1-6}$)alkyl; or (ii) a group of formula (a):

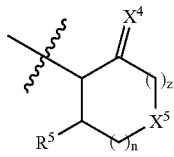

(a)

where:

n is 0, 1, or 2;

z is 0 or 1;

X$^4$ is selected from NR$^{19}$, S, or O where R$^{19}$ is hydrogen or (C$_{1-6}$)alkyl; and X$^5$ is —O—, —S—, —SO$_2$—, or —NR$^{20}$— where R$^{20}$ is selected from hydrogen, (C$_{1-6}$)alkyl, X$^6$C(O)OR$^{22}$, —X$^6$C(O)NR$^{22}$R$^{22a}$, —X$^6$S(O)$_2$NR$^{22}$R$^{22a}$, —X$^6$C(O)R$^{23}$, —X$^6$S(O)$_2$R$^{24}$, —R$^{25}$, —X$^6$C(O)OR$^{25}$, —X$^6$C(O)NR$^{22}$R$^{25}$, —X$^6$S(O)$_2$NR$^{22}$R$^{25}$, —X$^6$C(O)R$^{25}$ and —X$^6$S(O)$_2$R$^{25}$ in which X$^6$ is a bond or (C$_{1-6}$)alkylene; R$^{22}$ and R$^{22a}$ at each occurrence independently is hydrogen or (C$_{1-6}$)alkyl; R$^{23}$ is hydrogen, (C$_{1-6}$) alkyl or halo-substituted(C$_{1-6}$)alkyl, R$^{24}$ is (C$_{1-6}$)alkyl or halo-substituted(C$_{1-6}$)alkyl, and R$^{25}$ is (C$_{3-10}$)cycloalkyl(C$_{0-6}$) alkyl, hetero(C$_{3-10}$)cycloalkyl(C$_{0-3}$) alkyl, (C$_{6-10}$)aryl(C$_{0-6}$)alkyl, hetero(C$_{5-10}$)aryl(C$_{0-6}$) alkyl, (C$^{9-12}$)bicycloaryl(C$_{0-6}$)alkyl or hetero(C$_{8-12}$)bicycloaryl(C$_{0-6}$)alkyl provided that when R$^5$ is hydrogen, then both X$^4$ and X$^5$ are not —O—;

R$^5$ as defined above;

and furthermore within E any cycloalkyl, heterocycloalkyl, aryl or heteroaryl may be substituted with R$^X$ selected from —R$^{26}$, —X$^7$OR$^{26}$, —X$^7$SR$^{26}$, —X$^7$S(O)R$^{26}$, —X$^7$S(O)$_2$R$^{26}$, —X$^7$C(O)R$^{26}$, —X$^7$C(O)OR$^{26}$, —X$^7$OC(O)R$^{26}$, —X$^7$NR$^{26}$R$^{27}$, —X$^7$NR$^{27}$C(O)R$^{26}$, —X$^7$NR$^{27}$C(O)OR$^{26}$, X$^7$C(O)NR$^{26}$R$^{27}$, —X$^7$S(O)$_2$NR$^{26}$R$^{27}$, —X$^7$NR$^{27}$S(O)$_2$R$^{26}$, —X$^7$NR$^{27}$C(O)NR$^{26}$R$^{27a}$ and —X$^7$NR$^{27}$C(NR$^{27a}$)NR$^{26}$R$^{27b}$ and wherein E and R$^X$ may be substituted further with 1 to 5 radicals independently selected from (C$_{1-6}$)alkyl, cyano, halo, halo-substituted(C$_{1-4}$)alkyl, nitro, —X$^8$NR$^{28}$R$^{28a}$, —X$^8$NR$^{28}$C(O)R$^{28a}$, —X$^8$NR$^{28}$C(O)OR$^{28a}$, —X$^8$NR$^{28}$C(O)NR$^{28a}$R$^{28b}$, X$^8$NR$^{28}$C(NR$^{28a}$)NR$^{28b}$R$^{28c}$, —X$^8$OR$^{29}$, —X$^8$SR$^{29}$, —X$^8$C(O)OR$^{28}$, —X$^8$C(O)R$^{29}$, —X$^8$OC(O)R$^{29}$, —X$^8$C(O)NR$^{28}$R$^{28a}$, —X$^8$S(O)$_2$NR$^{28}$R$^{28a}$, —X$^8$NR$^{28}$S(O)$_2$R$^{29}$, —X$^8$P(O)(OR$^{28}$)OR$^{28a}$, —X$^8$OP(O)(OR$^{28}$)OR$^{28a}$,—X$^8$S(O)R$^{30}$ and —X$^8$S(O)$_2$R$^{30}$ wherein X$^7$ and X$^8$ are independently a bond or (C$_{1-6}$)alkylene; R$^{26}$ is (C$_{3-10}$)cycloalkyl(C$_{0-6}$)alkyl, hetero(C$_{3-10}$)cycloalkyl(C$_{0-3}$) alkyl, (C$_{6-10}$)aryl(C$_{0-6}$)alkyl, hetero(C$_{5-10}$)aryl(C$_{0-6}$) alkyl, (C$_{9-12}$)bicycloaryl(C$_{0-6}$alkyl or hetero(C$_{8-12}$)bicycloaryl(C$_{0-6}$)alkyl, R$^{27}$, R$^{27a}$, R$^{27b}$, R$^{28}$, R$^{28a}$, R$^{28b}$ and R$^{28c}$ at each occurrence independently is hydrogen or (C$_{1-6}$)alkyl, R$^{29}$ is hydrogen, (C$_{1-6}$)alkyl or halo-substituted(C$_{1-6}$)alkyl, and R$^{30}$ is (C$_{1-6}$)alkyl or halo-substituted(C$_{1-6}$)alkyl;

R$^1$ is (C$_{1-10}$)alkyl or —C(R$^{31}$)(R$^{32}$)X$^9$ wherein R$^{31}$ and R$^{32}$ are independently hydrogen or (C$_{1-6}$)alkyl and X$^9$ is selected from —X$^{10}$NR$^{33}$R$^{33a}$, —X$^{10}$NR$^{33}$C(O)R$^{33a}$, —X$^{10}$NR$^{33}$C(O)OR$^{33a}$, X$^{10}$NR$^{33}$C(O)NR$^{33a}$R$^{33b}$, —X$^{10}$NR$^{33}$C(NR$^{33a}$)NR$^{33b}$R$^{33c}$, —X$^{10}$OR$^{33}$, —X$^{10}$SR$^{33}$, —X$^{10}$C(O)OR$^{33}$, —X$^{10}$C(O)R$^{33}$, —X$^{10}$OC(O)R$^{33}$, —X$^{10}$C(O)NR$^{33}$R$^{33a}$, —X$^{10}$S(O)$_2$NR$^{33}$R$^{33a}$, —X$^{10}$NR$^{33}$S(O)$_2$R$^{33a}$, X$^{10}$P(O)(OR$^{33}$)OR$^{33a}$, —X$^{10}$OP(O)(OR$^{33}$)OR$^{33a}$, —X$^{10}$C(O)R$^{34}$, —X$^{10}$NR$^{33}$C(O)R$^{34}$, X$^{10}$S(O)R$^{34}$, —X$^{10}$S(O)$_2$R$^{34}$, —R$^{35}$, —X$^{10}$OR$^{35}$, —X$^{10}$SR$^{35}$, —X$^{10}$S(O)R$^{35}$, —X$^{10}$S(O)$_2$R$^{35}$, —X$^{10}$C(O)R$^{35}$, —X$^{10}$C(O)OR$^{35}$, —X$^{10}$OC(O)R$^{35}$, —X$^{10}$NR$^{33}$R$^{35}$, —X$^{10}$NR$^{33}$C(O)R$^{35}$, —X$^{10}$NR$^{33}$C(O)OR$^{35}$, —X$^{10}$C(O)NR$^{33}$R$^{35}$, —X$^{10}$S(O)$_2$NR$^{33}$R$^{35}$, —X$^{10}$NR$^{33}$S(O)$_2$R$^{35}$, —X$^{10}$NR$^{33}$C(O)NR$^{33a}$R$^{35}$ and —X$^{10}$NR$^{33}$C(NR$^{33a}$)NR$^{33b}$R$^{35}$ wherein X$^{10}$ is a bond or (C$_{1-6}$)alkylene; R$^{33}$, R$^{33a}$, R$^{33b}$, and R$^{33c}$ at each occurrence independently is hydrogen, (C$_{1-6}$)alkyl or halo-substituted(C$_{1-6}$)alkyl; R$^{34}$ is (C$_{1-6}$)alkyl or halo-substituted(C$_{1-6}$)alkyl; and R$^{35}$ is (C$_{3-10}$)cycloalkyl(C$_{0-6}$)alkyl, hetero(C$_{3-10}$)cycloalkyl(C$_{0-3}$)alkyl, (C$_{6-10}$)aryl(C$_{0-6}$)alkyl, hetero(C$_{5-10}$)aryl(C$_{0-6}$)alkyl, (C$_{9-10}$)bicycloaryl(C$_{0-6}$)alkyl or hetero(C$_{8-10}$)bicycloaryl(C$_{0-6}$)alkyl;

wherein within R$^1$ any alicyclic or aromatic ring system is unsubstituted or substituted further by 1 to 5 radicals independently selected from (C$_{1-6}$)alkyl, (C$_{1-6}$)alkylidene, cyano, halo, halo-substituted(C$_{1-4}$)alkyl, nitro, —X$^{11}$NR$^{36}$R$^{36a}$, —X$^{11}$NR$^{36}$C(O)R$^{36a}$, —X$^{11}$NR$^{36c}$(O)OR$^{36a}$, —X$^{11}$NR$^{36}$C(O)NR$^{36a}$R$^{36b}$, —X$^{11}$NR$^{36}$C(NR$^{36a}$)NR$^{36b}$R$^{36c}$, —X$^{11}$OR$^{36}$, X$^{11}$SR$^{36}$, —X$^{11}$C(O)OR$^{36}$, —X$^{11}$C(O)R$^{36}$, —X$^{11}$C(O)NR$^{36}$R$^{36a}$, X$^{11}$S(O)$_2$NR$^{36}$R$^{36a}$, —X$^{11}$NR$^{36}$S(O)$_2$R$^{36a}$, —X$^{11}$P(O)(OR$^{36}$)OR$^{36a}$, —X$^{11}$OP(O)(OR$^{36}$)OR$^{36a}$, X$^{11}$NR$^{36}$C(O)R$^{37}$, —X$^{11}$S(O)R$^{37}$, —X$^{11}$C(O)R$^{37}$ and —X$^{11}$S(O)$_2$R$^{37}$ and/or 1 radical selected from —R$^{38}$, —$X^{12}OR^{38}$, —$X^{12}SR^{38}$, —$X^{12}S(O)R^{38}$, —$X^{12}S(O)_2R^{38}$, —$X^{12}C(O)R^{38}$, —$X^{12}C(O)OR^{38}$, —$X^{12}OC(O)R^{38}$, —$X^{12}NR^{36}R^{38}$, —$X^{12}NR^{36}C(O)R^{38}$, —$X^{12}NR^{36}C(O)OR^{38}$, —$X^{12}C(O)NR^{36}R^{38}$, $X^{12}S(O)_2NR^{36}R^{38}$, —$X^{12}NR^{36}S(O)_2R^{38}$, —$X^{12}NR^{36}C(O)NR^{36a}R^{38}$ and —$X^{12}NR^{36}C(N^{36a})NR^{36b}R^{38}$; and within $R^1$ any aliphatic moiety is unsubstituted or substituted further by 1 to 5 radicals independently selected from cyano, halo, nitro, —$NR^{39}R^{39a}$, $N^{39}C(O)R^{39a}$, —$NR^{39}C(O)OR^{39a}$, —$NR^{39}C(O)NR^{39a}R^{39b}$, —$NR^{39}C(NR^{39a})NR^{39b}R^{39c}$, —$OR^{39}$, —$SR^{39}$, —$C(O)OR^{39}$, —$C(O)R^{39}$, —$OC(O)R^{39}$, —$C(O)NR^{39}R^{39a}$, —$S(O)_2NR^{39}R^{39a}$, —$NR^{39}S(O)_2R^{39a}$, —$P(O)(OR^{39})OR^{39a}$, —$OP(O)(OR^{39})OR^{39a}$, —$NR^{39}C(O)R^{40}$, —$S(O)R^{40}$ and —$S(O)_2R^{40}$; wherein $X^{11}$ and $X^{12}$ are independently a bond or $(C_{1-6})$alkylene; $R^{36}$, $R^{36a}$, $R^{36b}$, $R^{36c}$, $R^{39}$, $R^{39a}$, $R^{36b}$ and $R^{39c}$ at each occurrence independently is hydrogen, $(C_{1-6})$alkyl or halo-substituted$(C_{1-6})$alkyl; $R^{37}$ and $R^{40}$ are independently $(C_{1-6})$alkyl or halo-substituted$(C_{1-6})$alkyl; and $R^{38}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-10})$bicycloaryl$(C_{0-6})$alkyl or hetero$(C_{6-10})$bicycloaryl$(C_{0-6})$alkyl, provided that only one $(C_{9-10})$bicycloaryl$(C_{0-6})$alkyl or hetero$(C_{8-10})$bicycloaryl$(C_{0-6})$alkyl ring structure is present within $R^1$;

$R^{1a}$ is hydrogen or $(C_{1-6})$alkyl; or $R^1$ and $R^{1a}$ together with the carbon atoms to which they are attached form $(C_{3-8})$cycloalkylene or hetero$(C_{3-10})$cycloalkylene ring wherein said cycloalkylene ring is optionally substituted with one or two substitutents independently selected from $(C_{1-6})$alkyl, $(C_{1-6})$alkoxy, hydroxy, halo, hydroxyalkyl, or keto and said heterocycloalkylene ring is optionally substituted with one or two substitutents independently selected from $(C_{1-6})$alkyl, $(C_{1-4})$alkoxy, hydroxyalkyl, alkoxyalkyl, aminoalkyl, acyl, $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl wherein said aryl, heteroaryl, and heterocycloalkyl are optionally substituted with one, two, or three substitutents independently selected from $(C_{1-4})$alkyl, $(C_{1-6})$alkoxy, nitro, amino, halo, hydroxy, alkylthio, halo-substituted alkyl, halo-substituted alkoxy, acyl, —$OC(O)R^{39}$, —$C(O)NR^{39}R^{39a}$, —$S(O)_2NR^{39}R^{39a}$, —$S(O)_2R^{38}$ or —$S(O)_2R^4$ where $R^{38}$, $R^{39}$, $R^{39a}$, and $R^4$ are as defined above;

$R^2$ is hydrogen, hydroxy, or $(C_{1-6})$alkyl;

$R^3$ is hydrogen, $(C_{1-6})$alkyl, $(C_{1-6})$alkoxy, aryloxy, $(C_{3-8})$cycloalkyl, $(C_{3-8})$cycloalkyloxy, aryl, benzyl, tetrahydronaphthyl, indenyl, indanyl, $(C_{1-6})$alkylsulfonyl$(C_{1-6})$alkyl, $(C_{3-8})$cycloalkylsulfonyl$(C_{1-6})$alkyl, arylsulfonyl$(C_{1-6})$alkyl, heterocyclic ring selected from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzisoxazolyl, quinolinyl, tetrahydroquinolinyl, isoquinolinyl, tetrahydroisoquinolinyl, quinazolinyl, tetrahydroquinazolinyl, benzoxazolyl or quinoxalinyl, —OR where R is a heterocyclic moiety selected from those herein described in this paragraph, or amino; wherein $R^3$ is optionally substituted by one, two, or three $R^a$;

each $R^a$ is independently $(C_{1-6})$alkyl, $(C_{3-8})$cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, $(C_{1-6})$alkoxy, $(C_{1-6})$haloalkoxy, $(C_{1-6})$alkanoyl, $(C_{1-6})$alkanoyloxy, aryloxy, benzyloxy, $(C_{1-6})$alkoxycarbonyl, aryloxycarbonyl, aroyloxy, carbamoyl wherein the nitrogen atom may be independently mono or di-substituted by $(C_{1-6})$alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each $R^a$ is independently $(C_{1-6})$alkanoylamino, aroylamino, $(C_{1-6})$alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by $(C_{1-6})$alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each $R^a$ is independently $(C_{1-6})$alkoxycarbonylamino, aryloxycarbonylamino, $(C_{1-6})$alkylcarbamoyloxy, arylcarbamoyloxy, $(C_{1-6})$alkylsulfonylamino, arylsulfonylamino, aminosulfonyl, $(C_{1-6})$alkylaminosulfonyl, di-$(C_{1-6})$alkylaminosulfonyl, arylaminosulfonyl, amino wherein the nitrogen atom may be independently mono or di-substituted by $(C_{1-6})$alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyridinyl, pyrazinyl, indolyl, benzofuranyl, benzothienyl, benzimidazolyl, benzthiazolyl, quinolinyl, isoquinolinyl, quinazolinyl or quinoxalinyl, or each $R^a$ is independently halogen, hydroxy, $(C_{1-6})$alkoxy, $(C_{1-6})$haloalkyl, $(C_{1-6})$haloalkoxy, oxo, carboxy, cyano, nitro, carboxamide, amidino or guanidino, $R^a$ is may be further optionally substituted by one, two, or three $R^b$;

each $R^b$ is independently $(C_{1-6})$alkyl optionally partially or fully halogenated wherein one or more carbon atoms are optionally replaced by O, N, S(O), S(O)$_2$ or S and wherein said alkyl is optionally independently substituted with 1–2 oxo groups, —$NH_2$, or one or more $C_{1-4}$ alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, or quinoxalinyl; or each $R^b$ is independently $(C_{1-6})$cycloalkyl, aryl, aryloxy, benzyloxy, halogen, hydroxy, $(C_{1-6})$alkyl, $(C_{1-6})$alkoxy, $(C_{1-6})$haloalkyl, $(C_{1-6})$haloalkoxy, aminosulfonyl, $(C_{1-6})$alkylaminosulfonyl, di-$(C_{1-6})$alkylaminosulfonyl, arylaminosulfonyl, oxo, carboxy, cyano, nitro, mono-$C_{1-5}$alkylamino, di-$(C_{1-5})$alkylamino, carboxamide, amidino or guanidino;

R$^4$ is hydrogen, hydroxy, nitrile, or a (C$_{1-6}$)alkyl optionally partially or fully halogenated wherein one or more C atoms are optionally replaced by O, NH, S(O), S(O)$_2$ or S and wherein said alkyl chain is optionally independently substituted with 1–2 oxo groups, —NH$_2$, one or more C$_{1-4}$ alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl; or R$^3$ and R$^4$ together with the atoms to which they are attached form a heterocycloalkyl ring or a heterocyclic ring fused to an aryl or heteroaryl ring provided that the heterocycloalkyl rings contain at least an —SO$_2$— group, wherein said heterocycloalkyl rings may be optionally substituted on the aromatic and/or non-aromatic portion of the rings with one, two, or three R$^c$;

each R$^c$ and R$^{4a}$ is independently:

hydrogen, (C$_{1-6}$)alkyl optionally interrupted by one or two N, O, S, S(O), or S(O)$_2$ and optionally substituted by 1–2 oxo, amino, hydroxy, halogen, C$_1$ alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

halo, alkoxy, alkylthio, hydroxy, carboxy, aryl, aryloxy, aroyl, heteroaryl, (C$_{1-6}$)alkanoyl, —C(O)OR$^d$ where (R$^d$ is hydrogen, (C$_{1-6}$)alkyl, (C$_{1-6}$)alkoxyalkyl, (C$_{1-6}$)haloalkyl, (C$_{3-7}$)cycloalkyl, (C$_{3-7}$)cycloalkyl(C$_{1-6}$)alkyl, heteroaryl, heteroaryl(C$_{1-6}$)alkyl, aryl, or aryl (C$_{1-6}$)alkyl), (C$_{1-6}$)alkylsulfonyl, aryloxycarbonyl, benzyloxycarbonyl, (C$_{1-6}$)alkanoylamino, aroylamino, C$_{1-5}$ alkylthio, arylthio, (C$_{1-6}$)alkylsulfonylamino, arylsulfonylamino, (C$_{1-6}$)alkylamino-sulfonyl, arylaminosulfonyl, (C$_{3-6}$)cycloalkyl and benzyloxy wherein each of the aforementioned group is optionally substituted with halogen, hydroxy, (C$_{1-6}$)alkyl, (C$_{1-6}$)alkoxy, (C$_{1-6}$)haloalkyl, (C$_{1-6}$)haloalkoxy, oxo, carboxy, nitrile, nitro or NH$_2$C(O)—; or a pharmaceutically acceptable salts thereof provided that there are no more than 5 ring systems in a compound of Formula (Ia) or (Ib).

2. The compound of claim 1 wherein:

R$^3$ is (C$_{1-6}$)alkyl, (C$_{1-6}$)alkoxy, aryloxy, (C$_{3-8}$)cycloalkyl, (C$_{3-8}$)cycloalkyloxy, aryl, benzyl, tetrahydronaphthyl, indenyl, indanyl, (C$_{1-6}$)alkylsulfonyl(C$_{1-6}$)alkyl, (C$_{3-8}$)cycloalkylsulfonyl(C$_{1-6}$)alkyl, arylsulfonyl(C$_{1-6}$)alkyl, heterocyclic ring selected from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzisoxazolyl, quinolinyl, tetrahydroquinolinyl, isoquinolinyl, tetrahydroisoquinolinyl, quinazolinyl, tetrahydroquinazolinyl, benzoxazolyl or quinoxalinyl, —OR where R is a heterocyclic moiety selected from those herein described in this paragraph, or amino; wherein R$^3$ is optionally substituted by one, two, or three R$^a$;

each R$^a$ is independently (C$_{1-6}$)alkyl, (C$_{3-8}$)cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, (C$_{1-6}$)alkoxy, (C$_{1-6}$)haloalkoxy, (C$_{1-6}$)alkanoyl, (C$_{1-6}$)alkanoyloxy, aryloxy, benzyloxy, (C$_{1-6}$)alkoxycarbonyl, aryloxycarbonyl, aroyloxy, carbamoyl wherein the nitrogen atom may be independently mono or di-substituted by (C$_{1-4}$)alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each R$^a$ is independently (C$_{1-6}$)alkanoylamino, aroylamino, (C$_{1-6}$)alkylthio wherein the sulfur atom may be oxidized to a sulfoxide or sulfone, arylthio wherein the sulfur atom may be oxidized to a sulfoxide or sulfone, ureid'o wherein either nitrogen atom may be independently substituted by (C$_{1-6}$)alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or each R$^a$ is independently (C$_{1-6}$)alkoxycarbonylamino, aryloxycarbonylamino, (C$_{1-6}$)alkylcarbamoyloxy, arylcarbamoyloxy, (C$_{1-6}$)alkylsulfonylamino, arylsulfonylamino, aminosulfonyl, (C$_{1-6}$)alkylaminosulfonyl, di-(C$_{1-6}$)alkylaminosulfonyl, arylaminosulfonyl, amino wherein the nitrogen atom may be independently mono or di-substituted by (C$_{1-6}$)alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyridinyl, pyrazinyl, indolyl, benzofuranyl, benzothienyl, benzimidazolyl, benzthiazolyl, quinolinyl, isoquinolinyl, quinazolinyl or quinoxalinyl, or each R$^a$ is independently halogen, hydroxy, (C$_{1-6}$)alkoxy, (C$_{1-6}$)haloalkyl, (C$_{1-6}$)haloalkoxy, oxo, carboxy, cyano, nitro, carboxamide, amidino or guanidino, R$^a$ is may be further optionally substituted by one, two, or three R$^b$;

each R$^b$ is independently (C$_{1-6}$)alkyl optionally partially or fully halogenated wherein one or more carbon atoms are optionally replaced by O, N, S(O), S(O)$_2$ or S and wherein said alkyl is optionally independently substituted with 1–2 oxo groups, —NH$_2$, or one or more C$_{1-4}$ alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, or quinoxalinyl; or each R$^b$ is independently (C$_{3-6}$)cycloalkyl, aryl; aryloxy, benzyloxy, halogen, hydroxy, (C$_{1-6}$)alkyl, (C$_{1-6}$)alkoxy, (C$_{1-6}$)haloalkyl, (C$_{1-6}$)haloalkoxy, aminosulfonyl, (C$_{1-6}$)alkylaminosulfonyl, di-(C$_{1-6}$)alkylaminosulfonyl, arylaminosulfonyl, oxo, carboxy, cyano, nitro, mono-C$_{1-5}$)alkylamino, di-(C$_{1-5}$)alkylamino, carboxamide, amidino or guanidino; or R³ and R⁴ in (Ia) or (Ib) together with the atoms to which they are attached form a heterocycloalkyl ring or a heterocycloalkyl ring fused to an aryl or heteroaryl ring provided the heterocyclic rings contain at least an —SO₂— group, wherein said heterocycloalkyl rings are optionally substituted on the aromatic and/or non-aromatic portion of the rings with one, two, or three $R^c$;

each $R^c$ and $R^{4a}$ is hydrogen, $(C_{1-6})$alkyl optionally interrupted by one or two N, O, S, S(O), or S(O)₂ and optionally substituted by 1–2 oxo, amino, hydroxy, halogen, $C_{1-6}$)alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

halo, alkoxy, alkylthio, hydroxy, carboxy, aryl, aryloxy, aroyl, furanyl, thienyl, pyrrolyl, imidazolyl, pyridinyl, pyrimidinyl, $(C_{1-6})$alkanoyl, —C(O)OR$^d$ where (R$^d$ is hydrogen, $(C_{1-6})$alkyl, $(C_{1-6})$alkoxyalkyl, $(C_{1-6})$haloalkyl, $(C_{3-7})$-cycloalkyl, $(C_{3-7})$-cycloalkyl$(C_{1-6})$alkyl, heteroaryl, heteroaryl$(C_{1-4})$alkyl, aryl, or aryl$(C_{1-6})$alkyl), $(C_{1-6})$-alkylsulfonyl, aryloxycarbonyl, benzyloxycarbonyl, $(C_{1-6})$alkanoylamino, aroylamino, $C_{1-5}$ alkylthio, arylthio, $(C_{1-6})$alkylsulfonylamino, arylsulfonylamino, $(C_{1-6})$alkylamino-sulfonyl, arylaminosulfonyl, $(C_{3-6})$cycloalkyl and benzyloxy wherein each of the aforementioned group is optionally substituted with halogen, hydroxy, $(C_{1-6})$alkyl, $(C_{1-6})$alkoxy, $(C_{1-6})$-haloalkyl, $(C_{1-6})$haloalkoxy, oxo, carboxy, nitrile, nitro, or NH₂C(O)—.

3. The compound of claim 2 wherein E is —CHR⁶C(O)R¹⁰ where R⁶ is saturated alkyl, and R¹⁰ is hetero$(C_{4-10})$aryl optionally substituted with $(C_{3-10})$cycloalkyl, $(C_{6-10})$aryl [optionally substituted with —NR²⁸R²⁸ᵃ, —OR²⁹, or halo substituted $(C_{1-4})$ saturated alkyl], hetero$(C_{5-10})$aryl, $(C_{1-6})$ saturated alkyl, halo-substituted $(C_{1-4})$ saturated alkyl, or —X⁸OR²⁹ where X⁸ is $(C_{1-6})$ saturated alkylene, R²⁸ and R²⁸ᵃ are independently hydrogen or $(C_{1-6})$ saturated alkyl, R²⁹ is hydrogen, $(C_{1-6})$ saturated alkyl, or halo-substituted $(C_{1-6})$ saturated alkyl.

4. The compound of claim 3 wherein R¹ is —CH₂X⁹ wherein X⁹ is selected from —X¹⁰SR³³, —X¹⁰C(O)NR³³R³³ᵃ, —X¹⁰S(O)₂R³⁴, —X¹⁰COR³⁴, —X¹⁰OR³³, —R³⁵, —X¹⁰SR³⁵, —X¹⁰S(O)2R³⁵, —X¹⁰C(O)R³⁵, or —X¹⁰C(O)NR³³R³⁵ wherein X¹⁰ is a bond or $(C_{1-6})$alkylene; R³³ and R³³ᵃ at each occurrence independently is hydrogen, $(C_{1-6})$alkyl or halo-substituted$(C_{1-6})$alkyl; R³⁴ is $(C_{1-6})$alkyl or halo-substituted$(C_{1-6})$alkyl; and R³⁵ is $(C_{3-10})$ cycloalkyl$(C_{0-6})$alkyl, hetero$(C_{3-10})$cycloalkyl$(C_{0-3})$alkyl, $(C_{6-10})$aryl$(C_{0-6}$alkyl, hetero$(C_{5-10})$aryl$(C_{0-6})$alkyl, $(C_{9-10})$bicycloaryl$(C_{0-6})$alkyl or hetero$(C_{8-10})$bicycloaryl$(C_{0-6})$-alkyl wherein within R¹ any alicyclic or aromatic ring is optionally substituted with one, two, or three radicals independently selected from $(C_{1-6})$ saturated alkyl, benzyl, cyano, halo, halo-substituted($C_{1-4}$) saturated alkyl, —OR³⁶, or —R³⁸ where R³⁶ is $(C_{1-6})$ saturated alkyl or halo-substituted $(C_{1-6})$ saturated alkyl and R³⁸ is $(C_{6-10})$aryl and within R¹ any aliphatic moiety is unsubstituted or substituted further by 1 to 2 radicals independently selected from halo; and R¹ᵃ is hydrogen.

5. The compound of claim 3 wherein R¹ is 2-cyclohexylethyl, cyclohexylmethyl, cyclopentylmethyl, 2-cyclopentylethyl, tert-butylmethyl, 1-methylcyclopropylmethyl, 1-methylcyclohexylmethyl, 1-methylcyclopentylmethyl, 1,3-dimethylcyclopentylmethyl, morpholin-4-ylmethyl, 2,2-dimethyl-3-phenylpropyl, 1-benzylcyclopropylmethyl, 2-(1,1-difluoromethoxy)phenylmethanesulfonylmethyl, 2-methylpropylsulfonylmethyl, phenylmethanesulfonylmethyl, pyridin-2-ylmethanesulfonylmethyl, pyridin-4-yl-methanesulfonylmethyl, cyclopropylmethanesulfonylmethyl, pyridin-3-ylmethane-sulfonylmethyl, 2,6-difluorophenylmethanesulfonylmethyl, 2,2-difluoro-3-phenylpropyl, 2,2-dichloropropyl, 2,2-dichloro-3-phenylpropyl, 2-pyridin-2-ylsulfonylethyl, 2-phenylsulfonylethyl, 5-bromothien-2-ylmethyl, pyridin-4-ylmethyl, 2,2-dichloroethyl, 2,2,2-trichloroethyl, 1,4-dimethylcyclopentylmethyl, morpholin-4-ylmethyl, isopropylmethanesulfonylmethyl, 2-chlorobenzyl, or 4-fluorobenzyl and $^{1a}$ is hydrogen.

6. The compound of claim 4 wherein R³ is $(C_{1-5})$alkyl, $(C_{3-6})$cycloalkyl, phenyl, benzyl, naphthyl, $(C_{1-3})$alkylsulfonyl$(C_{1-3})$alkyl, $(C_{3-6})$cycloalkylsulfonyl$(C_{1-3})$alkyl, arylsulfonyl$(C_{1-3})$alkyl, pyrrolidinyl, piperidinyl, morpholinyl, thiomorpholinyl, piperazinyl, furanyl, thienyl, oxazolyl, thiazolyl, imidazolyl, pyridinyl, isoxazolyl, pyrimidinyl, pyrazinyl, pyridazinyl, indolyl, quinolinyl, benzofuranyl, benzothienyl, benzimidazolyl, benzthiazolyl, benzoxazolyl or amino; wherein R³ is optionally substituted by one, two, or three substituents independently selected from $R^a$;

each $R^a$ is independently $(C_{1-3})$alkyl, cyclopropyl, cyclopentyl, cyclohexyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, benzthiazolyl, benzoxazolyl, $(C_{1-3})$alkoxy, $(C_{1-3})$alkanoyl, $(C_{1-3})$alkanoyloxy, aryloxy, benzyloxy, $(C_{1-3})$alkoxycarbonyl, aryloxycarbonyl, aroyloxy, carbamoyl wherein the nitrogen atom may be independently mono or di-substituted by $(C_{1-3})$alkyl, aryl, pyrrolidinyl, piperidinyl, morpholinyl, thiomorpholinyl, piperazinyl, thienyl, oxazolyl, thiazolyl, imidazolyl, pyridinyl, pyrimidinyl, benzimidazolyl or benzthiazolyl, or each $R^a$ is independently $(C_{1-3})$alkanoylamino, aroylamino, $(C_{1-3})$alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by $(C_{1-3})$alkyl, aryl, pyrrolidinyl, piperidinyl, morpholinyl, thiomorpholinyl or piperazinyl, or each $R^a$ is independently $(C_{1-3})$alkoxycarbonylamino, aryloxycarbonylamino, $(C_{1-3})$alkylcarbamoyloxy, arylcarbamoyloxy, $(C_{1-3})$alkylsulfonylamino, arylsulfonylamino, $(C_{1-3})$alkylamino-sulfonyl, arylaminosulfonyl, amino wherein the nitrogen atom may be independently mono or di-substituted by $(C_{1-3})$alkyl, aryl, pyrrolidinyl, piperidinyl, morpholinyl, thiomorpholinyl or piperazinyl, or each $R^a$ is independently halogen, hydroxy, oxo, carboxy, cyano, nitro, carboxamide, amidino, or guanidino, $R^a$ may be further optionally substituted by one, two or three $R^b$; each $R^b$ is independently $(C_{1-3})$alkyl, aryl, $(C_{1-3})$alkoxy, $(C_{1-3})$haloalkyl, $(C_{1-3})$haloalkoxy, aryloxy, benzyloxy, halogen, hydroxy, oxo, carboxy, cyano, nitro, carboxamide, amidino or guanidino;

R² and R⁴ are hydrogen; and $R^{4a}$ is —C(O)OR$^d$ where (R$^d$ is hydrogen, $(C_{1-6})$alkyl, $(C_{1-6})$alkoxy$(C_{1-6})$alkyl, $(C_{1-6})$haloalkyl, $(C_{3-7})$cycloalkyl, $(C_{3-7})$cycloalkyl$(C_{1-6})$alkyl, heteroaryl, heteroaryl$(C_{1-6})$alkyl, awl, or aryl$(C_{1-6})$alkyl).

7. The compound of claim 4 wherein $R^2$ and $R^{4a}$ are hydrogen;
$R^3$ is $(C_{1-6})$ saturated alkyl, phenyl, pyrrolidinyl, piperidinyl, morpholinyl, thiomorpholinyl, piperazinyl, furanyl, thienyl, pyridinyl, or amino; wherein $R^3$ is optionally substituted by one, two or three $R^a$ where each $R^a$ is independently halo or $(C_{1-6})$ saturated alkyl; and
$R^4$ is hydrogen, $(C_{1-6})$ saturated alkyl, or halogenated alkyl.

8. The compound of claim 4 wherein $R^2$ and $R^{4a}$ are hydrogen and $R^3$ and $R^4$ together with the atoms to which they are attached form a 5 or 6 membered heterocycloalkyl ring containing at least an —$SO_2$— group or a 5 or 6 membered heterocycloalkyl ring containing at least an —$SO_2$— group and is fused to a phenyl, thienyl, pyrrolyl, or pyridinyl ring optionally independently substituted by one or two $R^c$.

9. The compound of claim 1 wherein:
$R^{1a}$, $R^2$, $R^3$ and $R^{4a}$ are hydrogen;
$R^1$ is —$CH_2X^9$ wherein $X^9$ is selected from —$X^{10}SR^{33}$, —$X^{10}C(O)NR^{33}R^{33a}$, —$X^{10}S(O)_2R^{34}$, —$X^{10}COR^{34}$, —$X^{10}OR^{33}$, —$R^{35}$, —$X^{10}SR^{35}$, —$X^{10}S(O)^2R^{35}$, —$X^{10}C(O)R^{35}$, or —$X^{10}C(O)NR^{33}R^{35}$ wherein $X^{10}$ is a bond or $(C_{1-6})$alkylene; $R^{33}$ and $R^{33a}$ at each occurrence independently is hydrogen, $(C_{1-6})$alkyl or halo-substituted$(C_{1-6})$alkyl; $R^{34}$ is $(C_{1-6})$alkyl or halo-substituted$(C_{1-6})$alkyl; and $R^{35}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-10})$bicycloaryl$(C_{0-6})$alkyl or hetero$(C_{8-10})$bicycloaryl$(C_{0-6})$-alkyl wherein within $R^1$ any alicyclic or aromatic ring is optionally substituted with one, two, or three radicals independently selected from $(C_{1-6})$ saturated alkyl, benzyl, cyano, halo, halo-substituted$(C_{1-6})$ saturated alkyl, —$OR^{36}$, or —$R^{38}$ where $R^{36}$ is $(C_{1-6})$ saturated alkyl or halo-substituted$(C_{1-6})$ saturated alkyl and $R^{38}$ is $(C_{6-10})$aryl and within $R^1$ any aliphatic moiety is unsubstituted or substituted further by 1 to 2 radicals independently selected from halo;
E is —$CHR^6C(O)R^{10}$ where $R^6$ is saturated alkyl, and $R^{10}$ is hetero$(C_{4-10})$aryl optionally substituted with $(C_{3-10})$ cycloalkyl, $(C_{6-10})$aryl [optionally substituted with —$NR^{28}R^{28a}$, —$OR^{29}$, or halo substituted $(C_{1-4})$ saturated alkyl], hetero$(C_{5-10})$aryl, $(C_{1-6})$ saturated alkyl, halo-substituted $(C_14$ saturated alkyl, or —$X^8OR^{29}$ where $X^8$ is $(C_{1-6})$ saturated alkylene, $R^{28}$ and $R^{28a}$ are independently hydrogen or $(C_{1-6})$ saturated alkyl, $R^{29}$ is hydrogen, $(C_{1-6})$ saturated alkyl, or halo-substituted $(C_{1-6})$ saturated alkyl; and
$R^4$ is —$SO_2R$ where R is pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl, or quinoxalinyl, —$SO_2$-saturated alkyl, $(C_{1-6})$ saturated alkyl substituted with a heteroaryl ring defined immediately above or pyrrolidinyl, piperidinyl, morpholinyl, thiomorpholinyl, piperazinyl, or indolinyl, —$SO_2NRR'$ where R and R' are independently hydrogen or $(C_{1-6})$ saturated alkyl wherein each of the aforementioned group is optionally substituted with halogen, hydroxy, $(C_{1-6})$ saturated alkyl, $(C_{1-6})$ saturated alkoxy, $(C_{1-6})$ saturated haloalkyl, $(C_{1-6})$ saturated haloalkoxy, oxo, carboxy, nitrile, nitro or —$CONH_2$—.

10. The compound of claim 1 wherein:
$R^{1a}$, $R^2$ and $R^4$ are hydrogen;

$R^1$ is —$CH_2X^9$ wherein $X^9$ is selected from —$X^{10}SR^{33}$, —$X^{10}C(O)NR^{33}R^{33a}$—$X^{10}S(O)_2R^{34}$, —$X^{10}COR^{34}$, —$X^{10}OR^{33}$, —$R^{35}$, —$X^{10}SR^{35}$, —$X^{10}S(O)^2R^{35}$, —$X^{10}C(O)R^{35}$, or —$X^{10}C(O)NR^{33}R^{35}$ wherein $X^{10}$ is a bond or $(C_{1-6})$alkylene; $R^{33}$ and $R^{33a}$ at each occurrence independently is hydrogen, $(C_{1-6})$alkyl or halo-substituted$(C_{1-6})$alkyl; $R^{34}$ is $(C_{1-6})$alkyl or halo-substituted$(C_{1-6})$alkyl; and $R^{35}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-10})$bicycloaryl$(C_{0-6})$alkyl or hetero$(C_{8-10})$bicycloaryl$(C_{0-6})$-alkyl wherein within $R^1$ any alicyclic or aromatic ring is optionally substituted with one, two, or three radicals independently selected from $(C_{1-6})$ saturated alkyl, benzyl, cyano, halo, halo-substituted$(C_{1-4})$ saturated alkyl, —$OR^{36}$, or —$R^{38}$ where $R^{36}$ is $(C_{1-6})$ saturated alkyl or halo-substituted$(C_{1-6})$ saturated alkyl and $R^{38}$ is $(C_{1-6})$aryl and within $R^1$ any aliphatic moiety is unsubstituted or substituted further by 1 to 2 radicals independently selected from halo;
E is —$CHR^6C(O)R^{10}$where $R^6$ is saturated alkyl, and $R^{10}$ is hetero$(C_{4-10})$aryl optionally substituted with $(C_{3-10})$ cycloalkyl, $(C_{6-10})$aryl [optionally substituted with —$NR^{28}R^{28a}$, —$OR^{29}$, or halo substituted $(C_{1-4})$ saturated alkyl], hetero$(C_{5-10})$aryl, $(C_{1-6})$ saturated alkyl, halo-substituted $(C_{1-4})$ saturated alkyl, or —$X^8OR^{29}$ where $X^8$ is $(C_{1-6})$ saturated alkylene, $R^{28}$ and $R^{28a}$ are independently hydrogen or $(C_{1-6})$ saturated alkyl, $R^{29}$ is hydrogen, $(C_{1-6})$ saturated alkyl, or halo-substituted $(C_{1-6})$ saturated alkyl;
$R^3$ is hydrogen, $(C_{1-6})$ saturated alkyl, phenyl, pyrrolidinyl, piperidinyl, morpholinyl, thiomorpholinyl, piperazinyl, furanyl, thienyl, pyridinyl, or amino; wherein $R^3$ is optionally substituted by one, two or three $R^a$ where $R^a$ is halo or $(C_{1,6})$ saturated alkyl; and
$R^{4a}$ is heteroaryl, $(C_{1-6})$ saturated alkylsulfonyl, or $(C_{1-6})$ halo-substituted saturated alkylsulfonyl.

11. A compound of Formula (Ia) or (Ib):

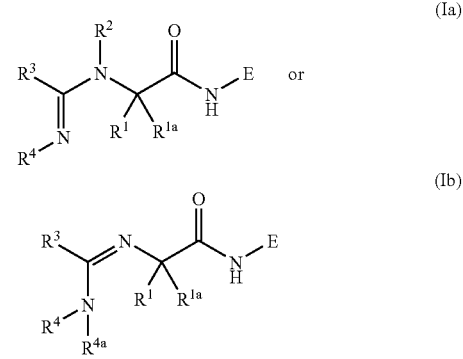

wherein:
$R^{1a}$, $R^2$ and $R^{4a}$ are hydrogen;
E is —$CHR^6C(O)R^{10}$ where $R^6$ is ethyl, propyl, or butyl, and $R^{10}$ is hetero$(C_{4-10})$aryl optionally substituted with $(C_{3-10})$aryl, $(C_{6-10})$aryl, hetero$(C_{5-10})$aryl, $(C_{1-6})$alkyl, halo, halo-substituted $(C_{1-4})$alkyl, $NR^{28}R^{28a}$, —$OR^{29}$, or —$COOR^{28}$, —$COR^{29}$ where $R^{28}$ and $R^{28a}$ are independently hydrogen or —$(C_{1-6})$alkyl, $R^{29}$ is hydrogen, —$(C^{1-6})$alkyl, or halo-substituted —$(C_{1-6})$alkyl;
$R^1$ is 2,2-dichloroethyl, 2,2,2-trichloroethyl, isopropylmethanesulfonylmethyl, 2,2-difluoro-3-phenylpropyl, 2,2-dichloro-3-phenylpropyl, 2-cyclohexylethyl, cyclohexylmethyl, cyclopentylmethyl, 2-cyclopentylethyl, tert-butylmethyl, 1-methylcyclopropylmethyl, 1-methylcyclohexylmethyl, 1-methylcyclopentylmethyl, 1,3-dimethylcyclopentylmethyl, morpholin-4-ylmethyl, 2,2-dimethyl-3-phenylpropyl, 1-benzylcyclopropylmethyl, 2-(1,1-difluoromethoxy)phenylmethanesulfonylmethyl, 2-methylpropylsulfonylmethyl, phenylmethanesulfonylmethyl, pyridin-2-ylmethanesulfonyl-methyl, pyridin-4-yl-methanesulfonylmethyl, cyclopropylmethanesulfonylmethyl, pyridin-3-ylmethane-sulfonylmethyl, 2,6-difluorophenylmethanesulfonylmethyl, 2,2-dichloropropyl, 2-pyridin-2-ylsulfonylethyl, 2-phenylsulfonylethyl, 5-bromothien-2-ylmethyl, pyridin-4-ylmethyl, 2-chlorobenzyl, or 4-fluorobenzyl;

$R^3$ is hydrogen, $(C_{1-6})$ saturated alkyl, phenyl, pyrrolidinyl, piperidinyl, morpholinyl, thiomorpholinyl, piperazinyl, furanyl, thienyl, pyridinyl, or amino; wherein $R^3$ is optionally substituted by one, two or three $R^a$ where each $R^a$ is independently halo or $(C_{1-6})$ saturated alkyl; and $R^4$ is hydrogen, $(C_{1-6})$ saturated alkyl, halo-substituted saturated alkyl, or $(C_{1-6})$ saturated alkylsulfonyl.

12. A compound of Formula (Ia) or (Ib):

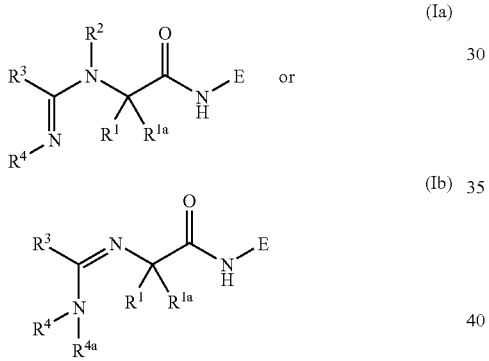

wherein:

$R^{1a}$, $R^2$ and $R^{4a}$ are hydrogen;

E is —CHR$^6$C(O)R$^{10}$ where R$^6$ ethyl and R$^{10}$ is benzoxazol-2-yl, oxazolo[4,5-b]pyridin-2-yl, 2-pyridin-3-yl-[1,3,4]-oxadiazol-5-yl, 2-pyridin-4-yl-[1,3,4]-oxadiazol-5-yl, 2-ethyl-[1,3,4]-oxadiazol-5-yl, 2-isopropyl-[1,3,4]-oxadiazol-5-yl, 2-tert-butyl-[1,3,4]-oxadiazol-5-yl, 2-phenyl-[1,3,4]-oxadiazol-5-yl, 2-methoxymethyl-[1,3,4]-oxadiazol-5-yl, 2-furan-2-yl-[1,3,4]-oxadiazol-5-yl, 2-thien-2-yl-[1,3,4]-oxadiazol-5-yl, 2-(4-methoxyphenyl)-[1,3,4]-oxadiazol-5-yl, 2-(2-methoxyphenyl)-[1,3,4]-oxadiazol-5-yl, 2-(3-methoxyphenyl)-[1,3,4]-oxadiazol-5-yl, 2-(2-trifluoromethoxyphenyl)-[1,3,4]-oxadiazol-5-yl, 2-(3-trifluoromethoxyphenyl)-[1,3,4]-oxadiazol-5-yl, 2-(4-trifluoromethoxyphenyl)-[1,3,4]-oxadiazol-5-yl, 2-(4-dimethylaminophenyl)-[1,3,4]-oxadiazol-5-yl, pyradizin-3-yl, pyrimidin-2-yl, 3-phenyl-[1,2,4]-oxadiazol-5-yl, 3-ethyl-[1,2,4]-oxadiazol-5-yl, 3-cyclopropyl-[1,2,4]-oxadiazol-5-yl, 3-thien-3-yl-[1,2,4]-oxadiazol-5-yl, 3-pyridin-4-yl-[1,2,4]-oxadiazol-5-yl, 5-ethyl-[1,2,4]-oxadiazol-3-yl, 5-phenyl-[1,2,4-oxadiazol-3-yl, 5-thien-3-yl-[1,2,4]-oxadiazol-3-yl, 5-trifluoromethyl-[1,2,4]-oxadiazol-3-yl, 5-pyridin-4-yl-[1,2,4]-oxadiazol-3-yl, or 5-phenyloxazol-2-yl;

2,2-dichloroethyl, 2,2,2-trichloroethyl, isopropylmethanesulfonylmethyl, 2,2-difluoro-3-phenylpropyl, 2,2-dichloro-3-phenylpropyl, 2-cyclohexylethyl, cyclohexylmethyl, cyclopentylmethyl, 2-cyclopentylethyl, tert-butylmethyl, 1-methylcyclopropylmethyl, 1-methylcyclohexylmethyl, 1-methylcyclopentylmethyl, 1,3-dimethylcyclopentylmethyl, morpholin-4-ylmethyl, 2,2-dimethyl-3-phenylpropyl, 1-benzylcyclopropylmethyl, 2-(1,1-difluoromethoxy)phenylmethanesulfonylmethyl, 2-methylpropylsulfonylmethyl, phenylmethanesulfonylmethyl, pyridin-2-ylmethanesulfonyl-methyl, pyridin-4-yl-methanesulfonylmethyl, cyclopropylmethanesulfonylmethyl, pyridin-3-ylmethane-sulfonylmethyl, 2,6-difluorophenylmethanesulfonylmethyl, 2,2-dichloropropyl, 2-pyridin-2-ylsulfonylethyl, 2-phenylsulfonylethyl, 5-bromothien-2-ylmethyl, pyridin-4-ylmethyl, 2-chlorobenzyl, or 4-fluorobenzyl;

$R^3$ is methyl, trifluoromethyl, 2,2,2-trifluoroethylamino, amino, N,N-dimethylamino, morpholin-4-yl, pyrrolidin-1-yl, piperidin-1-yl, 4-methylpiperazin-1-yl, thien-2-yl, thien-3-yl, furan-2-yl, furan-3-yl, pyridin-2-yl, pyridin-3-yl, pyridin-4-yl, pyrimidin-5-yl, pyrimidin-4-yl, oxazol-4-yl, oxazol-5-yl, thiazol-4-yl, thiazol-5-yl, quinolin-6-yl, indol-5-yl, 2-methylimidazol-4-yl, phenyl, or 4-fluorophenyl; and $R^4$ is hydrogen, 2,2,2-trifluoroethyl, methyl, or methylsulfonyl.

13. The compound of claim 11 wherein $R^4$ is 2,2,2-trifluoroethyl.

14. The compound of claim 12 wherein $R^4$ is 2,2,2-trifluoroethyl.

15. The compound of claim 1 wherein:

$R^{1a}$, $R^2$ and $R^{4a}$ are hydrogen;

E is —CHR$^6$C(O)R$^{10}$ where R$^6$ is saturated alkyl, and R$^{10}$ is hetero$(C_{4-10})$aryl optionally substituted with $(C_{3-10})$cycloalkyl, $(C_{6-10})$aryl [optionally substituted with —NR$^{28}$R$^{28a}$, —OR$^{29}$, or halo substituted $(C_{1-4})$ saturated alkyl], hetero$(C_{5-10})$aryl, $(C_{1-6})$ saturated alkyl, halo-substituted $(C_{1-4})$ saturated alkyl, or —X$^8$OR$^{29}$ where X$^8$ is $(C_{1-6})$ saturated alkylene, R$^{28}$ and R$^{28a}$ are independently hydrogen or $(C_{1-6})$ saturated alkyl, R$^{29}$ is hydrogen, $(C_{1-6})$ saturated alkyl, or halo-substituted $(C_{1-6})$ saturated alkyl;

R$^1$ is —CH$_2$X$^9$ wherein X$^9$ is selected from —X$^{10}$SR$^{33}$, —X$^{10}$C(O)NR$^{33}$R$^{33a}$, X$^{10}$S(O)$_2$R$^{34}$, —X$^{10}$COR$^{34}$, —X$^{10}$OR$^{33}$, —R$^{35}$, —X$^{10}$SR$^{35}$, —X$^{10}$S(O)$_2$R$^{35}$, —X$^{10}$C(O)R$^{35}$, or —X$^{10}$C(O)NR$^{33}$R$^{35}$ wherein X$^{10}$ is a bond or $(C_{1-6})$alkylene; R$^{33}$ and R$^{33a}$ at each occurrence independently is hydrogen, $(C_{1-6})$alkyl or halo-substituted$(C_{1-6})$alkyl; R$^{34}$ is $(C_{1-6})$alkyl or halo-substituted$(C_{1-6})$alkyl; and R$^{35}$ is $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-10})$bicycloaryl$(C_{0-6})$alkyl or hetero$(C_{8-10})$bicycloaryl$(C_{0-6})$-alkyl wherein within R$^1$ any alicyclic or aromatic ring is optionally substituted with one, two, or three radicals independently selected from $(C_{1-6})$ saturated alkyl, benzyl, cyano, halo, halo-substituted$(C_{1-4})$ saturated alkyl, —OR$^{36}$, or —R$^{38}$ where R$^{36}$ is $(C_{1-6})$ saturated alkyl or halo-substituted$(C_{1-6})$ saturated alkyl and R$^{38}$ is $(C_{6-10})$aryl and within R$^1$ any aliphatic moiety is unsubstituted or substituted further by 1 to 2 radicals independently selected from halo; and $R^3$ and $R^4$ together with the atoms to which they are attached form a group selected from:
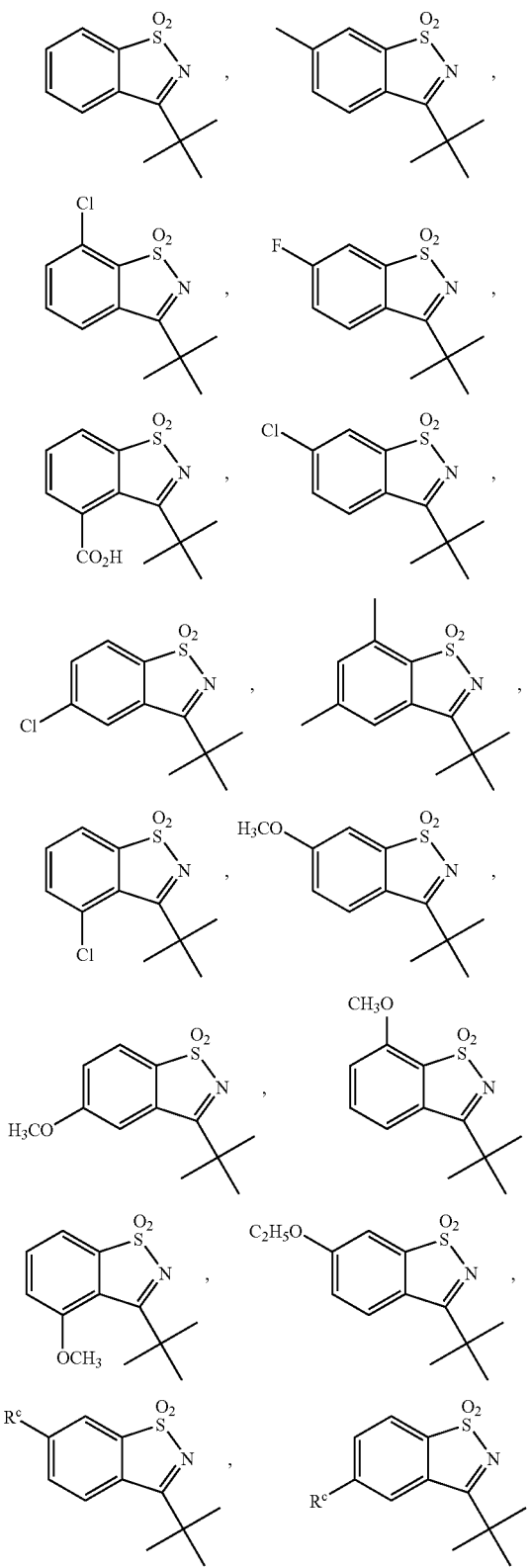
-continued
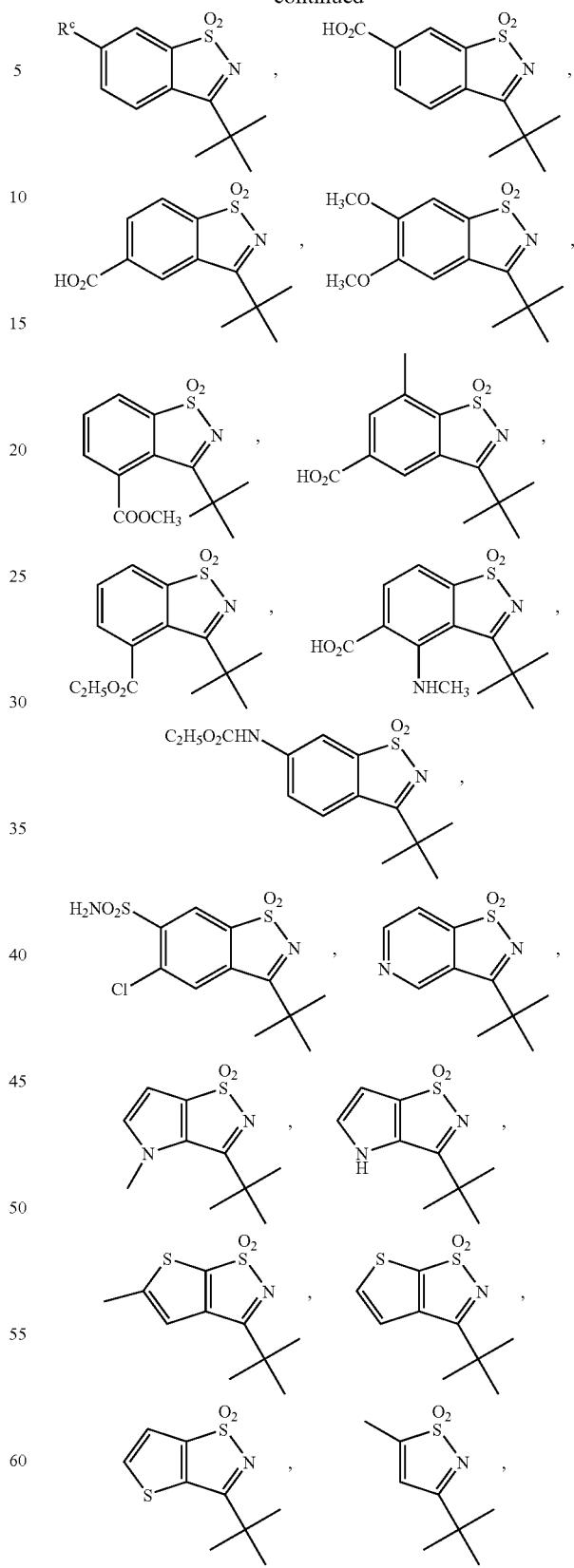

-continued
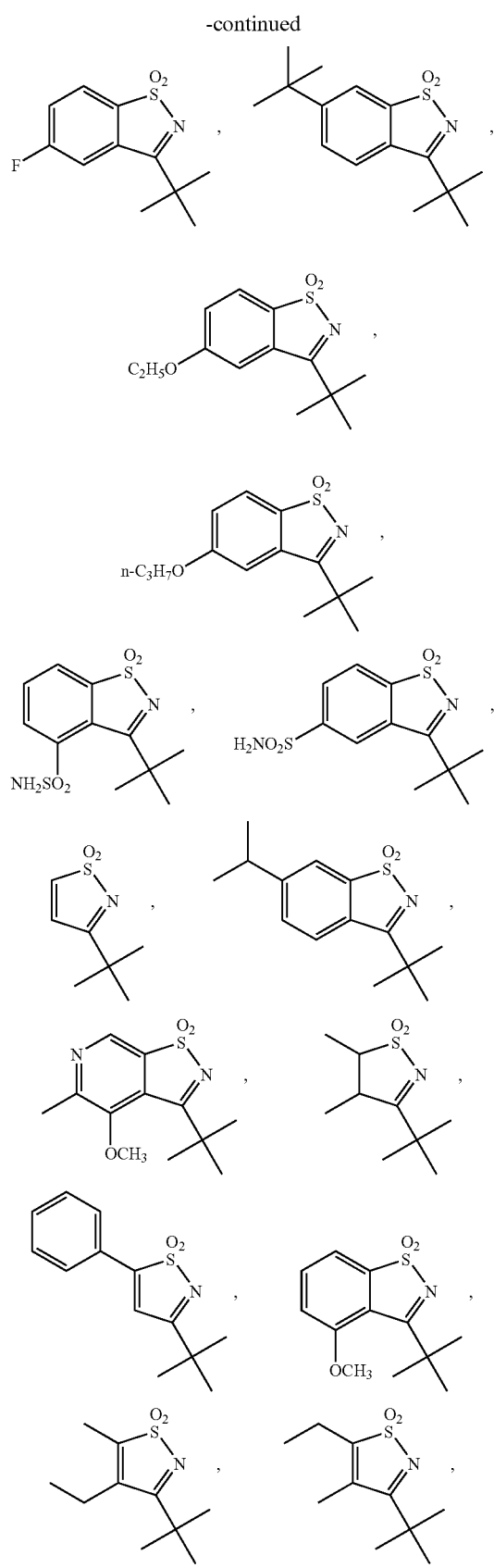
-continued
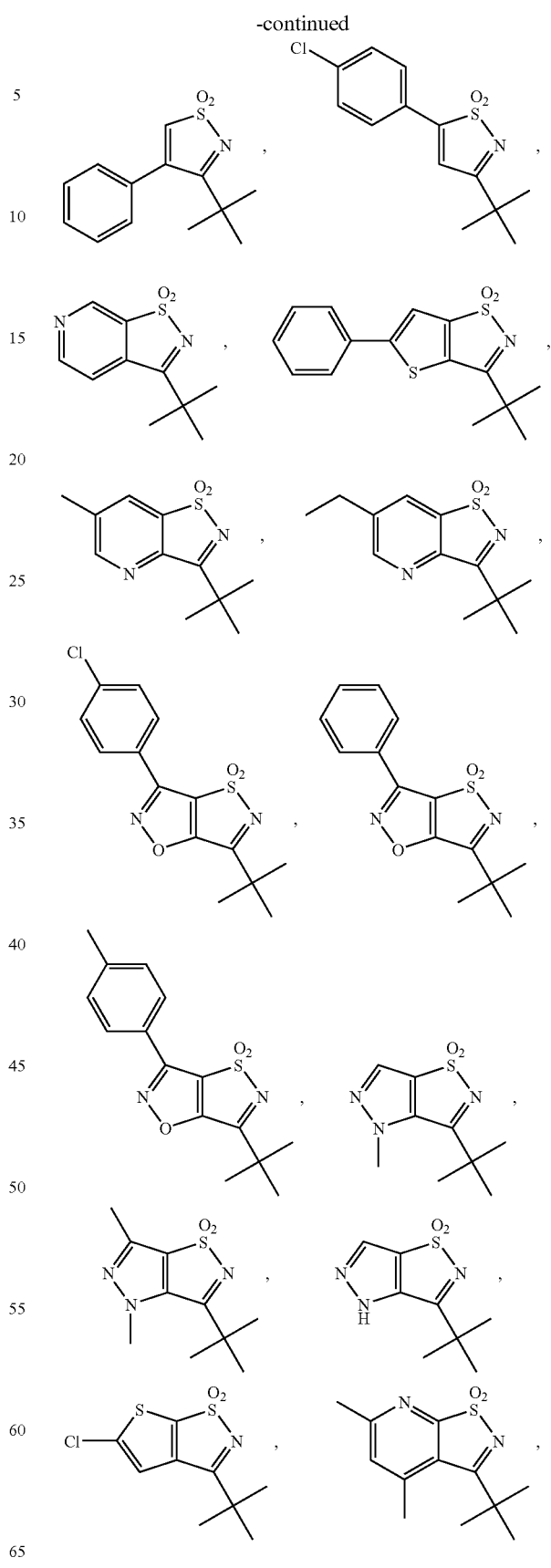

-continued

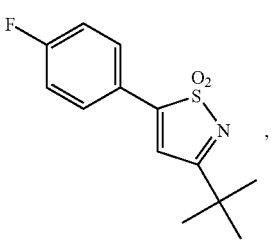

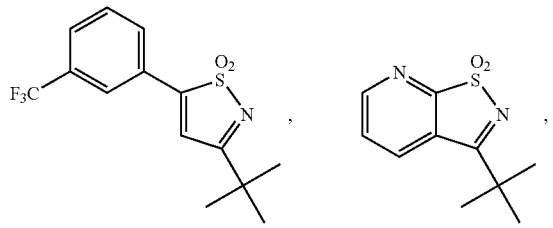

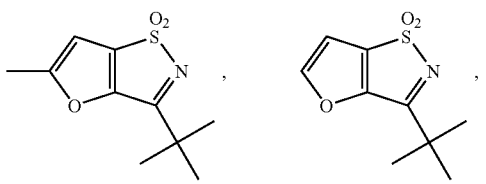

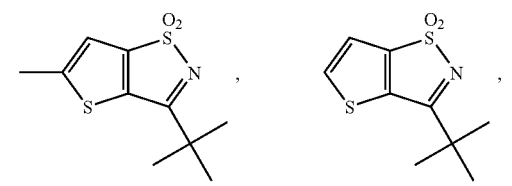

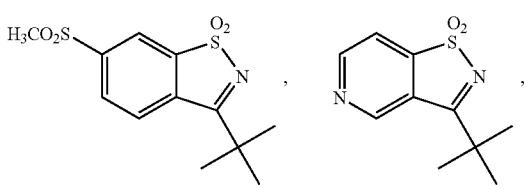

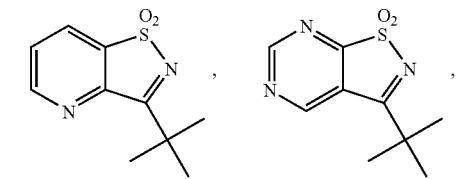

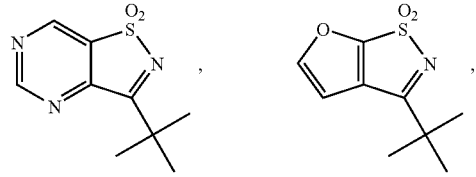

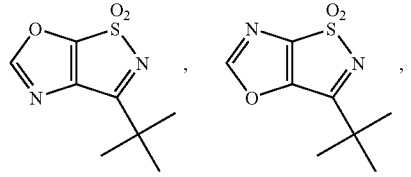

-continued

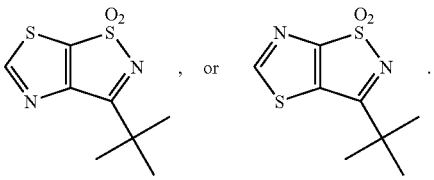, or where $R^c$ is amino, methylsulfonylamino, ethylsulfonylamino, methylamino, dimethylamino, acetylamino, methoxy, ethoxy, methylaminocarbonyl, aminocarbonyl, diethylaminocarbonyl, dimethylaminocarbonyl, methylaminocarbonyl, ureido, or ethoxycarbonylamino.

16. The compound of claim 15 wherein $R^1$ is 2,2-dichloroethyl, 2,2,2-trichloroethyl, isopropylmethanesulfonylmethyl, 2,2-difluoro-3-phenylpropyl, 2,2-dichloro-3-phenylpropyl, 2-cyclohexylethyl, cyclohexylmethyl, cyclopentylmethyl, 2-cyclopentylethyl, tert-butylmethyl, 1-methylcyclopropylmethyl, 1-methylcyclohexylmethyl, 1-methylcyclopentylmethyl, 1,3-dimethylcyclopentylmethyl, morpholin-4-ylmethyl, 2,2-dimethyl-3-phenylpropyl, 1-benzylcyclopropylmethyl, 2-(1,1-difluoromethoxy)phenylmethanesulfonylmethyl, 2-methylpropylsulfonylmethyl, phenylmethanesulfonylmethyl, pyridin-2-ylmethanesulfonyl-methyl, pyridin-4-yl-methanesulfonylmethyl, cyclopropylmethanesulfonylmethyl, pyridin-3-ylmethane-sulfonylmethyl, 2,6-difluorophenylmethanesulfonylmethyl, 2,2-dichloropropyl, 2-pyridin-2-ylsulfonylethyl, 2-phenylsulfonylethyl, 5-bromothien-2-ylmethyl, pyridin-4-ylmethyl, 2-chlorobenzyl, or 4-fluorobenzyl.

17. The compound of claim 16 wherein $R^6$ ethyl and $R^{10}$ is benzoxazol-2-yl, oxazolo[4,5-b]pyridin-2-yl, 2-pyridin-3-yl-[1,3,4]-oxadiazol-5-yl, 2-pyridin-4-yl-[1,3,4]-oxadiazol-5-yl, 2-ethyl-[1,3,4]-oxadiazol-5-yl, 2-isopropyl-[1,3,4]-oxadiazol-5-yl, 2-tert-butyl-[1,3,4]-oxadiazol-5-yl, 2-phenyl-[1,3,4]-oxadiazol-5-yl, 2-methoxymethyl-[1,3,4]-oxadiazol-5-yl, 2-furan-2-yl-[1,3,4]-oxadiazol-5-yl, 2-thien-2-yl-[1,3,4]-oxadiazol-5-yl, 2-(4-methoxyphenyl)-[1,3,4]-oxadiazol-5-yl, 2-(2-methoxyphenyl)-[1,3,4]-oxadiazol-5-yl, 2-(3-methoxyphenyl)-[1,3,4]-oxadiazol-5-yl, 2-(2-trifluoromethoxyphenyl)-[1,3,4]-oxadiazol-5-yl, 2-(3-trifluoromethoxyphenyl)-[1,3,4]-oxadiazol-5-yl, 2-(4-trifluoromethoxyphenyl)-[1,3,4]-oxadiazol-5-yl, 2-(4-dimethylaminophenyl)-[1,3,4]-oxadiazol-5-yl, pyradizin-3-yl, pyrimidin-2-yl, 3-phenyl-[1,2,4]-oxadiazol-5-yl, 3-ethyl-[1,2,4]-oxadiazol-5-yl, 3-cyclopropyl-[1,2,4]-oxadiazol-5-yl, 3-thien-3-yl-[1,2,4]-oxadiazol-5-yl, 3-pyridin-4-yl-[1,2,4]-oxadiazol-5-yl, 3-pyridin-2-yl-[1,2,4]-oxadiazol-5-yl, 5-ethyl-[1,2,4]-oxadiazol-3-yl, 5-phenyl-[1,2,4]-oxadiazol-3-yl, 5-thien-3-yl-[1,2,4]-oxadiazol-3-yl, 5-trifluoromethyl-[1,2,4]-oxadiazol-3-yl, 5-pyridin-4-yl-[1,2,4]-oxadiazol-3-yl, or 5-phenyloxazol-2-yl.

18. A pharmaceutical composition pharmaceutical composition comprising a therapeutically effective amount of a compound of claim 1, individual isomer or mixture of isomers thereof, or a pharmaceutically acceptable salt thereof, in admixture with one or more suitable excipients.

19. A pharmaceutical composition pharmaceutical composition comprising a therapeutically effective amount of a compound of claim 11, individual isomer or mixture of isomers thereof, or a pharmaceutically acceptable salt thereof, in admixture with one or more suitable excipients.

20. A pharmaceutical composition pharmaceutical composition comprising a therapeutically effective amount of a compound of claim 12, individual isomer or mixture of isomers thereof, or a pharmaceutically acceptable salt thereof, in admixture with one or more suitable excipients.

21. A pharmaceutical composition pharmaceutical composition comprising a therapeutically effective amount of a compound of claim 13, individual isomer or mixture of isomers thereot or a pharmaceutically acceptable salt thereof in admixture with one or more suitable excipients.

22. A pharmaceutical composition pharmaceutical composition comprising a therapeutically effective amount of a compound of claim 14, individual isomer or mixture of isomers thereof, or a pharmaceutically acceptable salt thereof, in admixture with one or more suitable excipients.

23. A method for treating a disease in an animal mediated by cysteine proteases, in particular cathepsin K, S, or F, which method comprises administering to the animal a pharmaceutical composition pharmaceutical composition comprising a therapeutically effective amount of a compound of claim 1, individual isomer or mixture of isomers thereof, or a pharmaceutically acceptable salt thereof, in admixture with one or more suitable excipients.

24. A method for treating a disease in an animal mediated by Cathepsin S which method comprises administering to the animal a pharmaceutical composition pharmaceutical composition comprising a therapeutically effective amount of a compound of claim 11, individual isomer or mixture of isomers thereof, or a pharmaceutically acceptable salt thereof, in admixture with one or more suitable excipients.

25. A method for treating a disease in an animal mediated by Cathepsin S which method comprises administering to the animal a pharmaceutical composition pharmaceutical composition comprising a therapeutically effective amount of a compound of claim 12, individual isomer or mixture of isomers thereof, or a pharmaceutically acceptable salt thereof, in admixture with one or more suitable excipients.

26. The method of claim 23 wherein the disease is psoriasis.

27. The method of claim 25 wherein the disease is psoriasis.

* * * * *